(12) United States Patent
Olsson et al.

(10) Patent No.: US 9,080,992 B2
(45) Date of Patent: Jul. 14, 2015

(54) ADJUSTABLE VARIABLE RESOLUTION INSPECTION SYSTEMS AND METHODS

(71) Applicants: Mark S. Olsson, La Jolla, CA (US); Scott Powell, San Diego, CA (US); Roger Shaffer, San Diego, CA (US); Stephanie Bench, Carlsbad, CA (US); Ray Merewhether, La Jolla, CA (US); David Cox, San Diego, CA (US); Eric Chapman, Santee, CA (US)

(72) Inventors: Mark S. Olsson, La Jolla, CA (US); Scott Powell, San Diego, CA (US); Roger Shaffer, San Diego, CA (US); Stephanie Bench, Carlsbad, CA (US); Ray Merewhether, La Jolla, CA (US); David Cox, San Diego, CA (US); Eric Chapman, Santee, CA (US)

(73) Assignee: SEESCAN, INC., San Diego, CA (US)

( * ) Notice: Subject to any disclaimer, the term of this patent is extended or adjusted under 35 U.S.C. 154(b) by 284 days.

(21) Appl. No.: 13/754,767

(22) Filed: Jan. 30, 2013

(65) Prior Publication Data

US 2014/0063229 A1 Mar. 6, 2014

Related U.S. Application Data

(60) Provisional application No. 61/592,524, filed on Jan. 30, 2012.

(51) Int. Cl.
*G01N 21/954* (2006.01)
*H04N 5/225* (2006.01)
*H04N 5/335* (2011.01)
*G03B 37/00* (2006.01)
*H04N 5/345* (2011.01)
*H04N 5/232* (2006.01)

(52) U.S. Cl.
CPC ........... *G01N 21/954* (2013.01); *H04N 5/2252* (2013.01); *H04N 5/2259* (2013.01); *H04N 5/232* (2013.01); *H04N 5/345* (2013.01); *G03B 37/005* (2013.01); *H04N 2005/2255* (2013.01)

(58) Field of Classification Search
CPC .................. H04N 2005/2255; H04N 5/23235; H04N 5/23232; H04N 5/3415; H04N 5/343; H04N 7/188; H04N 5/2259; G06T 7/0024; G01N 21/954; G03B 37/005
USPC ........... 348/82, 83, 84, 208.16, 211.14, 218.1
See application file for complete search history.

(56) References Cited

U.S. PATENT DOCUMENTS

| | | | |
|---|---|---|---|
| 6,204,879 B1 * | 3/2001 | Koseki et al. | 348/230.1 |
| 8,395,661 B1 * | 3/2013 | Olsson et al. | 348/86 |
| 8,547,428 B1 * | 10/2013 | Olsson et al. | 348/84 |
| 8,587,648 B2 * | 11/2013 | Olsson et al. | 348/85 |
| 2004/0141067 A1 * | 7/2004 | Nakayama et al. | 348/222.1 |
| 2004/0218099 A1 * | 11/2004 | Washington | 348/571 |
| 2005/0275725 A1 * | 12/2005 | Olsson et al. | 348/207.99 |
| 2007/0296827 A1 * | 12/2007 | Kubota et al. | 348/222.1 |
| 2011/0085022 A1 * | 4/2011 | Wang | 348/36 |
| 2014/0313316 A1 * | 10/2014 | Olsson et al. | 348/84 |

FOREIGN PATENT DOCUMENTS

| | | | |
|---|---|---|---|
| JP | 2007288761 A | * | 11/2007 |
| JP | 2011217345 A | * | 10/2011 |

* cited by examiner

*Primary Examiner* — John Villecco
(74) *Attorney, Agent, or Firm* — Steven C. Tietsworth, Esq.

(57) ABSTRACT

Camera heads configured to provide digitally articulated images or video, at adjustable resolutions and/or offsets and orientations, to a camera control unit (CCU) or other electronic computing system for display, storage, and/or transmission to other systems are disclosed.

35 Claims, 41 Drawing Sheets

Example Sensor Pixel Array

*Example Sensor Pixel Array*

*Example Analog Video Frame*

Example Sensor Pixel Array Sub-Divided Into Four Tiles

Example Multi-Sensor Array Sub-Divided Into Nine Tiles

Example of 4X Zoom / Pan Video Using One or Multiple Imagers

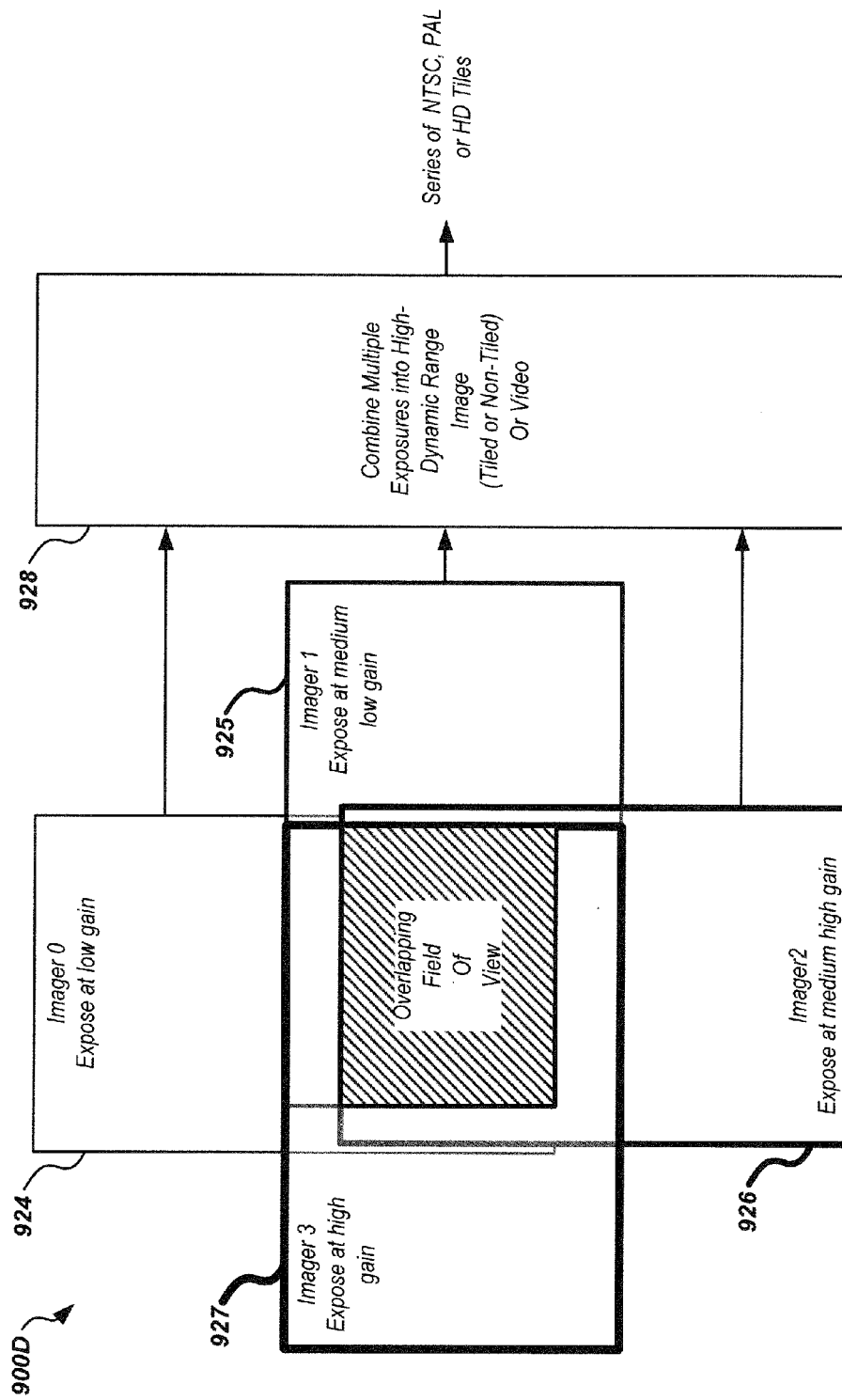

Example Tiled Video Operation Embodiment

Example Embodiment of High-
Resolution Still Mode Operation

Example Embodiment of Intermediate-
Resolution Still Mode Operation

Example Embodiment of High-Resolution, Low Frame Rate Video Mode Operation

Example Details of an Embodiment of Tile Generation and Processing For High Resolution Video Example Details of an Embodiment of Selected Tiling Processing Example Embodiment of Process to Provide a
Variable Resolution Display in an Inspection System Example Embodiment of Process to Provide
a Visual Display in an Inspection System Example Embodiment of Process to Provide a Variable Resolution Display in an Inspection System Based on a CCU Control Signal Example Image Sensor Pixel Array Embodiment
(20 x 16 array with 320 pixels)

Example Image Sensor Array Embodiment with 4 Image Sensors

3113
Viewing Port Position 3
(Transition to Image Sensor 2
Within Overlap Area))

3114
Viewing Port Position 4 (Mostly
or Entirely Within Sensor 1
Coverage Area)

3115
Viewing Port Position 5
(Within Overlap Area)

3116
Viewing Port Position 6 (Mostly or
Entirely Within Sensor 2 Coverage Area)

ADJUSTABLE VARIABLE RESOLUTION INSPECTION SYSTEMS AND METHODS

CROSS-REFERENCE TO RELATED APPLICATIONS

This application claims priority under 35 U.S.C. §119(e) to U.S. Provisional Patent Application Ser. No. 61/592,524, entitled ADJUSTABLE VARIABLE RESOLUTION INSPECTION SYSTEMS AND METHODS, filed on Jan. 30, 2012, the content of which is incorporated by reference herein in its entirety for all purposes.

FIELD

This disclosure relates generally to devices, systems, & methods for inspecting pipes or other cavities using images and video, which may be combined with sensor data, audio signals, location, orientation, and/or positioning information, and/or other data or information. More specifically, but not exclusively, the disclosure relates to a camera head with one or more electronic imaging elements, including electronic image sensors and associated optics, configured to provide electronically generated images or video, at adjustable resolutions and/or offsets, translations, zooms, and/or orientations, to a camera control unit (CCU) or other electronic computing system or device for display, storage, and/or re-transmission.

BACKGROUND

Pipe inspection systems for examining the interior of pipes, conduits, and other cavities or voids are known in the art. In order to correctly diagnose a defect within the interior of pipes, conduits, and other voids, a video camera linked to a push cable is generally employed. In a typical configuration, a rugged camera head connected to a push cable is sent through a pipe, and the camera head transmits video signals in an analog signaling format and at a fixed resolution along a transmission medium to view the scene on a remote monitoring system. These systems generally do not provide the capability of generating and sending variable resolution images, tiled images, zoomed or stitched images, HDR images, or other adjusted images to a camera control unit (CCU) or other electronic computing system or display device, nor do they provide variable orientation and/or resolution images based on conditions associated with the camera head or based on user inputs.

Accordingly, there is a need in the art to address the above-described as well as other problems.

SUMMARY

The present disclosure relates generally to pipe inspection systems, apparatus, and methods that may be used for imaging of pipes, conduits, and/or other cavities or spaces using zooming, tiling, translations, rotations, high dynamic range (HDR) image processing, and other imaging operations. Components of a self-leveling pipe inspection system may include camera heads, output signal transmission media, camera control units (CCUs), displays, audio transducers, position, orientation, location, and/or others sensors, as well as related components. Although the camera heads, CCUs, and other devices disclosure herein are presented in the context of a pipe inspection system, the teachings herein can similarly be applied to other camera and imaging applications in the art.

In one aspect, the present disclosure relates to a method of providing a variable-resolution visual display, such as in an inspection system such as a buried pipe or conduit visual inspection system. The method may include, for example, capturing a first image, covering a first field of view, in an electronic imaging element, including an image sensor and associated optics, of a camera head. The camera head may include one imaging element or a plurality of imaging elements. In embodiments with a plurality of imaging elements, fields of view of ones of the imaging elements may overlap, and/or the optical axes of the imaging elements may be non-parallel, such as by being divergent. The method may include converting the first image to a first analog signal. The method may further include providing the first analog signal to an electronic computing system, such as a camera control unit (CCU), portable computer, tablet, or other device. The method may include sensing a condition associated with the camera head. The method may further include generating, responsive to the sensing, ones of a plurality of tiled images corresponding to tiled subsets of the first field of view. The method may include converting the plurality of tiled images to a second analog signal. The method may further include providing the second analog signal to the CCU. In embodiments with multiple imaging elements, the first image and tiled images may be generated based on pixel data provided from multiple image sensors.

In another aspect, the disclosure relates to apparatus & systems for implementing the above-described method or other methods disclosed herein, in whole or in part.

In another aspect, the disclosure relates to means for implementing the above-described method or other methods described herein, in whole or in part.

In another aspect, the disclosure relates to computer readable media including instructions for causing a processor to implement the above-described method or other methods described herein, in whole or in part.

Various additional features, aspects, and embodiment and implementation details are further described below in conjunction with the appended Drawings.

BRIEF DESCRIPTION OF THE DRAWINGS

The present disclosure may be more fully appreciated in connection with the following detailed description taken in conjunction with the accompanying drawings, wherein:

FIG. 9D illustrates details of how imagers with overlapping FOV may have different exposures and may be combined to produce a single High Dynamic Range (HDR) image or video stream;

DETAILED DESCRIPTION OF EMBODIMENTS

Overview

Figure 1A:
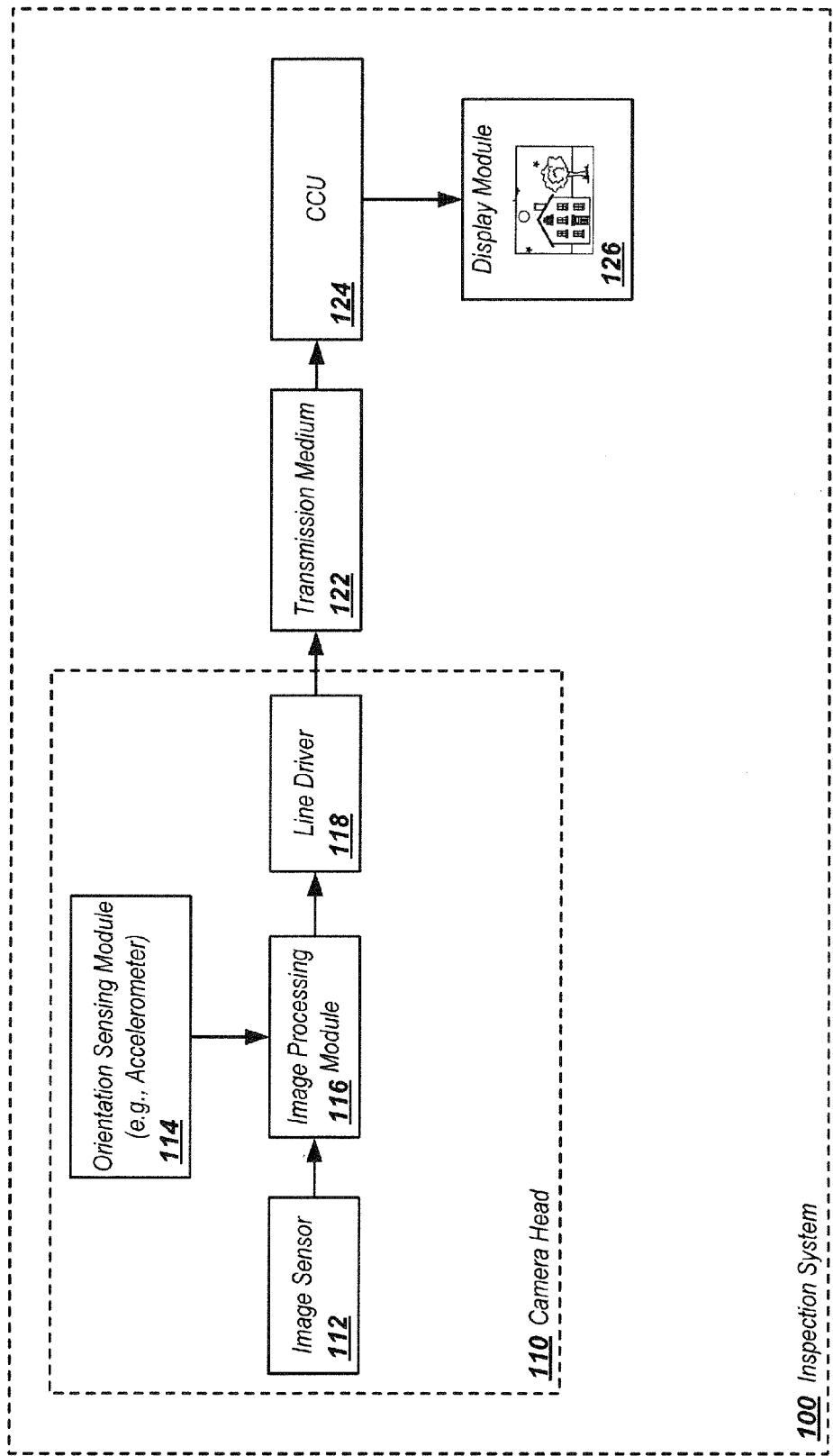
FIG. 1A is a block diagram illustrating details of an embodiment of a pipe inspection system.

The present disclosure relates generally to pipe inspection systems, apparatus, and methods that may be used for imaging of pipes, conduits, and/or other cavities or spaces using zooming, tiling, translations, rotations, high dynamic range (HDR) image processing, and stitching of images from a single image sensor or multiple image sensors, and/or other imaging operations based on images generated in one or more image sensors. Components of a self-leveling pipe inspection system may include camera heads, output signal transmission media, camera control units (CCUs) or other coupled electronic computing systems, displays, audio transducers, position, orientation, location, and/or others sensors, as well as related components.

In an exemplary embodiment, a pipe inspection system camera head may include elements or components for providing a digital image, such as an imaging element or elements including an electronic image sensor or sensor array using CCD, CMOS, or other image or video sensing and capture technologies and associated optics, along with an orientation and/or position sensing module for providing orientation and/or position data associated with the position and/or orientation of the image sensor, which may be relative to a reference orientation such as that due to gravity (e.g., up/down relative to the earth's surface or a normal upright orientation). Output images or video from the camera head or CCU may be based on images captured by multiple image sensors, such as a video stream including images captured from a first image sensor before a transition of a viewport through an overlap area, and another image sensor during or subsequent to the transition. The images may be registered between the image sensors using light markers or targets, such as laser dots or grating generated targets projected in an area being viewed by the camera head.

Output images and/or video data from the image sensor may be provided, along with the orientation/position data and/or other data or information, such as audio information, other sensor data, and the like, to an image processing module or modules including one or more processing elements, which may then provide an output video signal that is adjusted in the camera head for a desired orientation, such as an upright orientation relative to gravity.

The output video signal may then be provided to a camera control unit (CCU) or other system or device that includes display and/or storage capability. A visual display corresponding to the output video signal may then be provided, such as by rendering the output video signal on a display device of the CCU or other system such as an LCD display, and/or on other devices such as printer, and/or on another video or image output device. In addition, the image or video may also be stored for future display, output, transmission, processing, and/or analysis. Operator input at the CCU or other control device may be provided to the camera head to control digital articulation (i.e., translations, zooms, rotations, etc. of the output viewport and corresponding images or video generated at the camera head) and/or the camera head may be articulated automatically, such as in response to sensor input from a position, orientation, or location sensor, such as an accelerometer, compass sensor, gravitations sensor, location or position sensor, or other sensors in or on the camera head.

For example, in one aspect, the present disclosure relates to a method of providing a variable-resolution visual display, such as in an inspection system such as a buried pipe or conduit visual inspection system. The method may include, for example, capturing a first image, covering a first field of view, in an electronic imaging element, including an image sensor and associated optics, of a camera head. The camera head may include one imaging element or a plurality of imaging elements. In embodiments with a plurality of imaging elements, fields of view of ones of the imaging elements may overlap, and/or the optical axes of the imaging elements may be non-parallel, such as by being outward divergent. The method may include converting the first image to a first analog signal. The method may further include providing the first analog signal to an electronic computing system, such as a camera control unit (CCU), portable computer, tablet, or other device. The method may include sensing a condition associated with the camera head. The method may further include generating, responsive to the sensing, ones of a plurality of tiled images corresponding to tiled subsets of the first field of view. The method may include converting the plurality of tiled images to a second analog signal. The method may further include providing the second analog signal to the CCU.

The method may include, for example, receiving the first analog signal, such as at the CCU or other communicatively coupled electronic computing system. The method may include further include providing a first visual output corresponding to the first analog signal on a display device, such as on an LCD or other display element integral with or coupled to the CCU or other device, at a first resolution. The method may further include receiving the second analog signal, such as at the CCU. The method may further include combining the plurality of tiled images of the second analog signal to provide a second visual output on the display device at a second resolution higher than the first resolution.

The method may include, for example, generating a second plurality of tiled images corresponding to tiled subsets of the first field of view. The method may further include converting the second plurality of tiled images to a third analog signal. The method may further include providing the third analog signal to the CCU or other device. The method may include combining the second plurality of tiled images of the third analog signal to provide a third visual output on the display device. The third visual output may be provided at a third resolution, which may be different than the first and the second resolutions.

The second visual output may, for example, be provided as a zoomed-in field of view relative to the first visual output. The first image and the second image may be provided as a sequence of images and/or as frames of a video signal. The first image and the aggregate of the tiled subsets may correspond to the same field of view. The aggregate of the tiled subsets may correspond to a narrower field of view than the first image. The aggregate of the tiled subsets may correspond to a wider field of view than the first image. The aggregate of the tiled subsets may correspond to a rotation and/or translation of the field of view of a previous image or images. The first image and the aggregate of the tiled subsets may, for example, fully or approximately correspond to the field covered by the full frame of the image sensor.

The plurality of tiled images may, for example, include four tiled images. Each of the four tiled images may correspond to approximately one quarter of the first field of view. The plurality of tiled images may include nine tiled images. Each of the nine tiled images may correspond to approximately one ninth of the first field of view.

The condition may, for example, correspond to a motion of the camera head. The motion may be a stop motion. The motion may be a speed threshold. The motion may be a start motion. The condition may be a rotation of the image sensor relative to a reference orientation, which may be provided by a sensor such as an accelerometer, a compass sensor, a gravitational sensor, a radio-positioning or GPS sensor, or other motion, position, or location sensors. The condition may relate to a motion of the camera head. The motion of the camera head may be sensed using an accelerometer, gyroscopic sensor, or compass sensor. The condition may relate to a motion of the camera head. The motion may be sensed using a cable counter sensor or other cable deployment or retraction sensor. The reference orientation may be an up-down gravitational orientation. The reference orientation may be a height or distance orientation within a pipe or conduit.

The method may, for example, include providing data associated with the plurality of tiled images. The data may relate to a position and/or size of the ones of the plurality of tiled images. The data associated with the plurality of tiles may be other sensor data captured in conjunction with the tiled images. The ones of the plurality of tiled images may be at a lower resolution than the first image. The first image and the ones of the plurality of tiled images may be provided fully or partially as a digital signal rather than an analog signal. Audio data or information may be provided in conjunction with the plurality of tiled images. The first image and the ones of a plurality of tiled images may be stored on a digital storage medium. The first image and the ones of a plurality of tiled images may be provided as a hard copy output. The data may relate to the transmission mode currently being used to transmit the tiled images. The transmission mode may be one of a single frame mode or a tiled mode. The data may relate to one or more sensing conditions associated with the image being transmitted. The data may relate to imager status information at the time of image capture. The data may relate to camera head status information at the time of image capture. A subset of the plurality of tiled images may be used to generate the zoomed-in field of view of the second visual output.

The method may include, for example, capturing a subsequent image in a second electronic imaging element of the camera head, and generating a third analog signal. The third analog signal may be based at least in part on the subsequent image. The third analog signal may be based entirely on the subsequent image. The third analog signal may be generated based on a combination of the subsequent image captured by the second image sensor and one or more pixels of a previous image captured by the image sensor. The subsequent image may be captured during or subsequent to a transition of a viewport or tile across an overlap area between the first image sensor and the second image sensor.

The method may include, for example, generating an output image sequence or video stream from two or more imaging elements in the camera head. The output image sequence or video stream may be switched from pixel data of a first imaging element of the two or more imaging elements to pixel data from a second imaging element of the plurality of imaging elements, such as during transition of a viewport through an overlap region of the field of view or coverage area of the imaging elements.

The method may include, for example, projecting, from the camera head, a light marker on an area being inspected. The light marker may be a laser dot or plurality of laser dots. The light marker may be a target graphic generated by a grating or other optical element. The target, such a laser dot or plurality of laser dots or other graphic, may be strobed in synchronization with a video frame rate associated with the imaging elements or a processing element of the camera head. The strobing may provide the target during only certain image captures or video frames. The method may further include registering images from a first image sensor of a plurality of image sensors with one or more other image sensors of the plurality of image sensor using the projected target. The registering images may be done with images generated during transition of the viewport through the overlap region.

The method may include, for example, capturing a subsequent plurality of images in the camera head at different exposures and generating, based on the subsequent plurality of images, a high dynamic range (HDR) image. The method may further include generating a plurality of HDR images and generating a video stream based on the plurality of HDR images. The method may further include projecting, from the camera head, a light marker or target on an area being inspected. The method may further include generating the HDR image based in part on registration of the images at different exposures using the projected light marker or target.

The method may include, for example, capturing a subsequent image in a second electronic image sensor of the camera head and generating a stereoscopic image pair or stereoscopic video stream based on the subsequent image and an additional image captured by the image sensor. The method may further include projecting, from the camera head, a light marker or target on an area being inspected. The method may further include generating the stereo pair based in part on registration of the subsequent image and additional image using the projected light marker or target.

The method may include, for example, capturing a subsequent image in a second electronic image sensor of the camera head and generating a stitched composite image or video stream based on the subsequent image and an additional image captured by the image sensor. The method may further include projecting, from the camera head, a light marker or target on an area being inspected. The method may further include generating the stitched composite image based in part on registration of the subsequent image and additional image using the projected light marker or target.

In another aspect, the disclosure relates to a camera head. The camera head may include, for example, a body, a sensor module configured to sense a condition associated with the body, and an electronic imaging element, including an image sensor and associated optics, disposed in the body. The image sensor may be configured to capture a first image covering a first field of view, and capture, responsive to the sensing, data to be used to derive ones of a plurality of tiled images corresponding to tiled subsets of the first field of view. The camera head may further include an electronics module. The electronics module may be configured to convert the first image to a first analog signal. The electronics module may be further configured to provide the first analog signal to a camera control unit (CCU). The electronics module may be configured to extract the plurality of tiled images. The electronics module may be further configured to convert the plurality of tiled images to a second analog signal. The electronics module may be further configured to provide the second analog signal to the CCU.

The camera head may, for example, include a second electronic imaging element disposed in the body. The imaging elements may be oriented such that a field of view of the imaging element may overlaps with a field of view of the second imaging element. The optical axis of the imaging element and the second imaging element may be disposed in a non-parallel orientation. The optical axes of the imaging element and the second imaging element may be divergent.

The camera head may, for example, include a plurality of additional imaging elements. The imaging element may be oriented along a camera head centerline, and additional imaging elements may be oriented with outward divergent optical axes relative to the imaging element. The optical axes of ones of the plurality of additional imaging elements may be non-parallel. The optical axes of ones of the plurality of additional imaging element may be divergent.

The camera head may, for example, include a lighting element to project a light marker on an area being viewed by the camera head. The lighting element may be a laser or other light emitting device. A grating or other optical element may be used to generate the target.

In another aspect, the disclosure relates to a camera head. The camera head may include, for example, a body and a plurality of electronic imaging elements, each including an image sensor and associated optics, disposed in the body. The camera head may further include a sensor module configured to sense a condition associated with the body. The camera head may further include an electronics module. The electronics module may include one or more processing elements to convert images from the image sensors of the plurality of imaging elements to output image sequences or video streams. The electronics module may be further configured to generate analog or digital video output based on the image sequences or video streams. The analog or digital video output may be provided to a CCU or other electronic computing system for display, storage, or transmission to other systems.

Ones of the plurality of imaging elements may, for example, be oriented such that a field of view of the imaging element overlaps with a field of view of others of the imaging elements. The optical axes of the imaging elements may be disposed in a non-parallel orientation. The optical axes of the imaging elements may be divergent. A first of the plurality of imaging elements may be oriented along a camera head centerline, and additional imaging elements may be oriented with outward divergent optical axes relative to the first imaging element. The camera head may further including lighting elements to project a light marker or target on an area being viewed.

The camera head may, for example, include a second electronic imaging element disposed in the body. The imaging elements may be oriented such that a field of view of the imaging element may overlaps with a field of view of the second imaging element. The optical axis of the imaging element and the second imaging element may be disposed in a non-parallel orientation. The optical axes of the imaging element and the second imaging element may be divergent.

The camera head may, for example, include a plurality of additional imaging elements. The imaging element may be oriented along a camera head centerline, and additional imaging elements may be oriented with outward divergent optical axes relative to the imaging element. The optical axes of ones of the plurality of additional imaging elements may be non-parallel. The optical axes of ones of the plurality of additional imaging element may be divergent.

The camera head may, for example, include a lighting element to project a light marker or target on an area being viewed by the camera head. The lighting element may be a laser or other light emitting device. A grating or other optical element may be used to generate the marker or target.

In another aspect, the disclosure relates to a Camera Control Unit (CCU) for controlling operation of a camera head, such as positioning, rotation, translation, deployment, withdrawal, zooming, panning, lighting from the camera head, and/or other control functions associated with operation of the camera head and/or inspection system. The CCU may include, for example, a body, an electronics module to receive and process analog and/or digital signals including image and/or video and/or audio data provided from the camera head, an electronics module configured to extract the image or video data from the analog signals or digital signals. The CCU may further include a processing module configured to interpret the analog signal being received, or a translated version of the analog signal, and format data contained therein for display, storage, and/or transmission, such as storage of the data on a memory of the CCU and/or display images, video, audio, and/or sensor data on the display or audio output device of the CCU, and/or send the images, video, audio, and/or sensor data from the CCU to another electronic computing system. The processing module may be further configured to receive data along with or in conjunction with the video signal and use the data to display, storage, and/or render a visual display associated with the images or video.

In another aspect, the disclosure relates to a pipe or conduit inspection system. The system may include, for example, a camera control unit (CCU), a camera head including a camera head body, a sensor module configured to sense a condition associated with the body, and an electronic imaging element, including an image sensor and associated optics, disposed in the body. The image sensor may be configured to capture a first image covering a first field of view, and capture, responsive to the sensing, data to be used to derive ones of a plurality of tiled images corresponding to tiled subsets of the first field of view. The system may further include an electronics module. The electronics module may be configured to convert the first image to a first analog signal, provide the first analog signal to a camera control unit (CCU), extract the plurality of tiled images, convert the plurality of tiled images to a second analog signal, and provide the second analog signal to the CCU. The system may further include a transmission media to carry the analog signals from the camera head to the CCU. The CCU may include a CCU body, an electronics module configured to receive and process analog signals including image or video data provided from the camera head, an electronics module configured to extract the image or video data from the analog signals, and a CCU processing module configured to interpret the analog signal being received, or a translated version of the analog signal, and format data contained therein for display, storage, and/or transmission. The camera head may further include a plurality of imaging elements and/or a lighting element for generating markers on an area being viewed.

In another aspect, the disclosure relates to a camera head. The camera head may include, for example, means for capturing a first image, covering a first field of view, in an electronic image sensor, means for converting the first image to a first analog signal, means for providing the first analog signal to a camera control unit (CCU), means for sensing a condition associated with the image sensor, means for generating, responsive to the sensing, ones of a plurality of tiled images corresponding to tiled subsets of the first field of view, means for converting the plurality of tiled images to a second analog signal, and means providing the second analog signal to the CCU. The camera head may further include additional imaging means and/or means for projecting a light target on an area being viewed.

In another aspect, the disclosure relates to a processor readable medium including instructions for causing a processor or computer to receive a first image, covering a first field of view, from an electronic image sensor, convert the first image to a first analog signal, provide the first analog signal to a camera control unit (CCU), receive a sensor signal associated with a sensed condition related to the image sensor, generate, responsive to the sensing, ones of a plurality of tiled images corresponding to tiled subsets of the first field of view, convert the plurality of tiled images to a second analog signal, and provide the second analog signal to the CCU.

In another aspect, the disclosure relates to a method of providing a visual display in an inspection system. The method may include, for example, providing a first image from an electronic image sensor of a camera head, at a first resolution, to a camera control unit (CCU), sensing a condition associated with the image sensor, generating, responsive to the sensing, a second image from the image sensor at a second resolution different from the first resolution, and providing the second image to the CCU.

The method may, for example, further include providing a first visual output corresponding to the first image on a display device, and providing a second visual output corresponding to the second image on the display device. The first image and the second image may be provided as frames of a video signal. The second resolution may be lower than the first resolution. The first image may correspond fully or approximately with the field covered by the full frame of the image sensor, and the second image may correspond with a subset of the field covered by the full frame. The subset may be a the of the full frame. The may be approximately one quarter of the full frame. The may be approximately one ninth of the full frame. The may be approximately centered within the field of view of the image sensor.

The method may further include, for example, receiving a the selection signal from the CCU. The tile position may be based at least in part on the tile selection signal. The selection signal may include a zoom-in signal. The selection signal may include a zoom-out signal. The selection signal may include a translation signal, such as a signal to translate the provided images or video in an X and/or Y direction on the display screen (i.e., where the Z-direction is in and out of the screen). The selection signal may include a rotation signal, such as a signal to rotate the orientation of the display about the center of the or another center point within the inspection area being imaged by the camera head.

The method may further include, for example, receiving a tile selection signal from the CCU, such as at the camera head. The tile size and/or tile position may be based at least in part on the tile selection signal. The condition may correspond to a motion of the image sensor. The motion may be a stop motion. The motion may be a speed threshold. The motion may be a start motion. The condition may be a rotation of the image sensor relative to a reference orientation. The reference orientation may be an up-down gravitational orientation.

The first image may, for example, correspond with approximately the full frame of the image sensor and the second image may correspond with a subset of the full frame. The subset of the full frame may be selected based at least in part on the motion of the image sensor. The method may further include providing data associated with the second image to the CCU. The second image may correspond to a tiled subset of the full frame and the data may correspond to a position and/or size of the tiled subset.

In another aspect, the disclosure relates to a camera head. The camera head may include, for example, a body, a sensor module configured to sense a condition associated with the body, and an electronic imaging element, including an image sensor and associated optics, disposed in the body. The imaging element may be configured to capture a first image covering a first field of view and capture, responsive to the sensing, a second image. The camera head may further include an electronics module configured to convert the first image to a first analog signal, provide the first analog signal to a camera control unit (CCU), and convert the second image to a second analog signal. The second analog signal may have a second resolution different from the first resolution. The second analog signal may be provided to the CCU.

The camera head may, for example, include a second electronic imaging element disposed in the body. The imaging elements may be oriented such that a field of view of the imaging element may overlaps with a field of view of the second imaging element. The optical axis of the imaging element and the second imaging element may be disposed in a non-parallel orientation. The optical axes of the imaging element and the second imaging element may be divergent.

The camera head may, for example, include a plurality of additional imaging elements. The imaging element may be oriented along a camera head centerline, and additional imaging elements may be oriented with outward divergent optical axes relative to the imaging element. The optical axes of ones of the plurality of additional imaging elements may be non-parallel. The optical axes of ones of the plurality of additional imaging element may be divergent.

The camera head may, for example, include a lighting element to project a light marker on an area being viewed by the camera head. The lighting element may be a laser or other light emitting device. A grating or other optical element may be used to generate the target.

In another aspect, the disclosure relates to a Camera Control Unit (CCU). The CCU may include, for example, a body, an electronics module to receive and process analog signals including image or video data provided from a camera head, an electronics module configured to extract the image or video data from the analog signals, and a processing module configured to interpret the analog signal being received, or a translated version of the analog signal, and format data contained therein for display, storage, and/or transmission. The processing module may be further configured to receive data in conjunction with the video signal and use the data to either display, store, or produce a visual display associated with the images.

In another aspect, the disclosure relates to a pipe inspection system. The pipe inspection system may include, for example, a camera control unit and a camera head. The camera head may include a body, a sensor module configured to sense a condition associated with the body, and an electronic image sensor disposed in the body. The image sensor may be configured to capture a first image covering a first field of view, and capture, responsive to the sensing, a second image. The system may further include an electronics module. The electronics module may be configured to convert the first image to a first analog signal, provide the first analog signal to a camera control unit (CCU), convert the second image to a second analog signal, the second analog signal having a second resolution different from the first resolution, and provide the second analog signal to the CCU. The system may further include a transmission media to carry the analog signals from the camera head to the CCU, such as a wired or wireless transmission media. The CCU may include a CCU body, an electronics module configured to receive and process analog signals including image or video data provided from the camera head, an electronics module configured to extract the image or video data from the analog signals, and a CCU processing module configured to interpret the analog signal being received, or a translated version of the analog signal, and format data contained therein for display, storage, and/or transmission. The camera head may further include a plurality of imaging elements and/or a lighting element for generating markers on an area being viewed.

In another aspect, the disclosure relates to a camera head. The camera head may include, for example, means for providing a first image from an electronic image sensor at a first resolution to a camera control unit (CCU), means for sensing a condition associated with the image sensor, means for generating, responsive to the sensing, a second image from the image sensor at a second resolution different from the first resolution, and means for providing the second image to the CCU. The camera head may further include additional imaging means and/or means for projecting a light marker on an area being viewed.

In another aspect, the disclosure relates to a machine readable medium including instructions for causing a processor or computer to receive a first image, at a first resolution, from an electronic image sensor, convert the first image to a first analog signal, provide the first analog signal to a camera control unit (CCU), receive a sensor signal associated with a sensed condition related to the image sensor, receive a second image, at a second resolution different from the first resolution, from the image sensor, convert the second image to a second analog signal, and provide the second analog signal to the CCU. The instructions may further include instructions to project a light marker on an area being viewed. The instructions may further include instructions for registering images from the electronic image sensor and a second electronic image sensor based in part on the light marker.

In another aspect, the disclosure relates to a method of providing a user-controlled variable-resolution visual display in an inspection system. The method may include, for example, capturing a first image, covering a first field of view, in an electronic image sensor of a camera head. The method may further include converting the first image to a first analog signal, and providing the first analog signal to a camera control unit (CCU) or other electronic computing system. The method may further include receiving a control from the CCU and generating, at least partially in responsive to the control signal, ones of a plurality of tiled images corresponding to tiled subsets of the first field of view. The method may further include converting the plurality of tiled images to a second analog signal. The method may further include providing the second analog signal to the CCU or other electronic computing system.

The method may further include, for example, receiving the first analog signal, such as at the CCU or other electronic computing system, providing a first visual output corresponding to the first analog signal on a display device at a first resolution, receiving the second analog signal, and combining the plurality of tiled images of the second analog signal to provide a second visual output on the display device at a second resolution higher than the first resolution. The control signal may be generated based on a user input received at the CCU. The control signal may be generated at the CCU. The CCU may generate the control signal responsive to a processing analysis of motion based on previously received images or data from the camera head. The analysis may include a determination of lack of motion in the previously received images.

In another aspect, the disclosure relates to a camera head. The camera head may include, for example, a body and an electronic imaging element, including an image sensor and associated optics, disposed in the body. The image sensor may be configured to capture a first image covering a first field of view and capture data for generating a second image responsive to a received control signal. The camera head may further include an electronics module. The electronics module may be configured to receive a control signal from a CCU, convert the first image to a first analog signal, provide the first analog signal to a camera control unit (CCU), convert the second image to a second analog signal, where the second analog signal has a second resolution different from the first resolution, and provide the second analog signal to the CCU.

The camera head may, for example, include a second electronic imaging element disposed in the body. The imaging elements may be oriented such that a field of view of the imaging element may overlaps with a field of view of the second imaging element. The optical axis of the imaging element and the second imaging element may be disposed in a non-parallel orientation. The optical axes of the imaging element and the second imaging element may be divergent.

The camera head may, for example, include a plurality of additional imaging elements. The imaging element may be oriented along a camera head centerline, and additional imaging elements may be oriented with outward divergent optical axes relative to the imaging element. The optical axes of ones of the plurality of additional imaging elements may be non-parallel. The optical axes of ones of the plurality of additional imaging element may be divergent.

The camera head may, for example, include a lighting element to project a light marker on an area being viewed by the camera head. The lighting element may be a laser or other light emitting device. A grating or other optical element may be used to generate the target.

In another aspect, the disclosure relates to a camera control unit (CCU). The CCU may include, for example, a body, an electronics module configured to receive and process analog signals including image or video data provided from a camera head, an electronics module configured to extract the image or video data from the analog signals, an analysis module configured to receive a plurality of images or video from a camera head and generate a control signal to be provided to the camera head, and a processing module configured to interpret the analog signal being received, or a translated version of the analog signal, and format data contained therein for display, storage, and/or transmission.

The processing module may, for example, be further configured to receive data in conjunction with the video signal, and use the data to display, store, and/or produce a visual display associated with the images or video. The analysis module may be configured to compare ones of a plurality of images or video previously received from the camera head for motion and generate, based at least in part on the analysis, the control signal based on the determined motion or lack of motion.

In another aspect, the disclosure relates to a pipe inspection system. The pipe inspection system may, for example, include a camera control unit (CCU) and a camera head. The camera head may include a body and an electronic image sensor disposed in the body. The image sensor may be configured to capture a first image covering a first field of view, and capture data for generating a second image responsive to a received control signal. The camera head may further include an electronics module. The camera head electronics module may be configured to receive the control signal from a CCU, convert the first image to a first analog signal, provide the first analog signal to a camera control unit (CCU), convert the second image to a second analog signal, the second analog signal having a second resolution different from the first resolution, and provide the second analog signal to the CCU. The system may further include a transmission media to carry the analog signals from the camera head to the CCU. The CCU may include a CCU body, a CCU electronics module to receive and process analog signals including image or video data provided from a camera head and extract the image or video data from the analog signals, a CCU motion analysis module configured to receive a plurality of images or video from a camera head and generate a control signal to be provided to the camera head associated with a desired motion, rotation, and/or translation, and a processing module configured to interpret the analog signal being received, or a translated version of the analog signal, and format data contained therein for display, storage, and/or transmission on or from the CCU.

In another aspect, the disclosure relates to a processor readable medium. The processor readable medium may, for example, include instructions for causing a process or computer to capture a first image, covering a first field of view, such as in an electronic image sensor of a camera head. The instructions may further include instructions to convert the first image to a first analog signal, provide the first analog signal to a camera control unit (CCU), receive a control signal from the CCU, generate, at least partially in responsive to the control signal, ones of a plurality of tiled images corresponding to tiled subsets of the first field of view, convert the plurality of tiled images to a second analog signal, and provide the second analog signal to the CCU.

Various additional aspects and details of self-leveling systems and methods that may be used in embodiments in conjunction with the disclosure herein are described in co-assigned U.S. patent application Ser. No. 10/858,628, filed Jun. 1, 2004, entitled SELF-LEVELING CAMERA, as well as co-assigned U.S. patent application Ser. No. 13/358,463, filed Jan. 22, 2012, entitled SELF-LEVELING INSPECTION SYSTEMS AND METHODS. The entire disclosure of each of these applications is incorporated by reference herein in its entirety.

Various additional features, aspects, and embodiment and implementation details are further described below in conjunction with the appended Drawings.

Example Embodiments

FIG. 1A illustrates one embodiment 100 of such an inspection system in accordance with various aspects. Inspection system 100 may include a camera head module 110 configured to mechanically house components such as an imaging element including an electronic image sensor 112 and associated optics (not shown in FIG. 1), an orientation and/or position sensing module 114, an image processing module 116, a line driver module 118, and/or other modules or components, such as power supplies, insulation elements, heating elements, defogging elements, lens elements, and the like (not shown). The camera head may be coupled to a push-cable or other mechanism for deploying or retracting the camera head from a pipe or other cavity. In some embodiments, such as those described subsequently herein with respect to FIG. 19, the camera head may further include a plurality of imaging elements and/or additional lighting elements, such as LEDs, lasers, and the like (not shown in FIG. 1).

The image sensor 112 may be, for example, a high resolution image sensor such as an OV9810 9-Megapixel 1080 HD Video Image Sensor, manufactured by the Omnivision®

Company, and/or a MT9P006 5-Megapixel HD Video Image Sensor, manufactured by the Aptina® Company, and/or other image sensors known or developed in the art. In one embodiment, the image sensor may have an element array of n×m pixels, where n×m may be 3488×2616. In one embodiment, the image sensor may have an element array of n×m pixels, where n×m may be 2592×1944. Various other pixel array configurations may also be used in different embodiments.

Orientation module 114 may include, for example, a sensing component such as an accelerometer, such as a three-axis accelerometer like the LSM303DLH, or nine-axis device, such as MPU-9150, manufactured by InvenSense®, and/or other position and/or orientation elements known or developed in the art, such as compass sensors, inertial navigation sensors, and the like. Image processing module 116 may comprise, for example, a programmable logic device such as a Field Programmable Gate Array (FPGA), such as the Actel Igloo AGL250V2-CSG196I, Spartan®-6 FPGA (45-150 size), one or more microcontrollers or microprocessors, digital signal processors (DSPs), ASICs, memory devices, and/or other electronic and processing components capable of being configured to receive, store, and process images such as described subsequently herein. Camera head 110 may further include one or more output circuits configured to provide image and/or video output, such as a line driver 118 as shown. Additional position or location modules may also be included in camera head 110, such as GPS modules or other radio-based location modules, optical location or positioning modules, and the like.

A transmission medium 122 may be used to connect the camera head 110 to a camera control module (CCU) 124, or other electronic computing system or device, to transfer output image or video signals or data. In an exemplary embodiment the transmission medium 122 may be a wired conductor configured to carry the output signal, however, in other embodiments the transmission medium may be a wireless medium, fiber optic medium, or other signal transmission medium. Camera control module 124 may include various components for controlling and monitoring camera operation and information, such as image or video resolution, lighting, zooming, panning, rotation, and/or related operations or functions.

A display module 126 may be coupled to and/or incorporated in control module 124 to render images and/or video provided from camera head 110. Control module 124 may include additional components such as memory for storing video and/or images and/or associated data or metadata, as well as components for providing other output such as digital video and/or image files, hard copy, or other data or information. The camera control module may further include one or more wired or wireless communication modules (not shown) for sending and/or receiving data from other devices or systems, such as cellular data communication modules, Wi-Fi or Wi-Max modules, ISM-band modules, Ethernet modules, USB or Firewire modules, or other communications modules, such as GPS.

Figure 3:
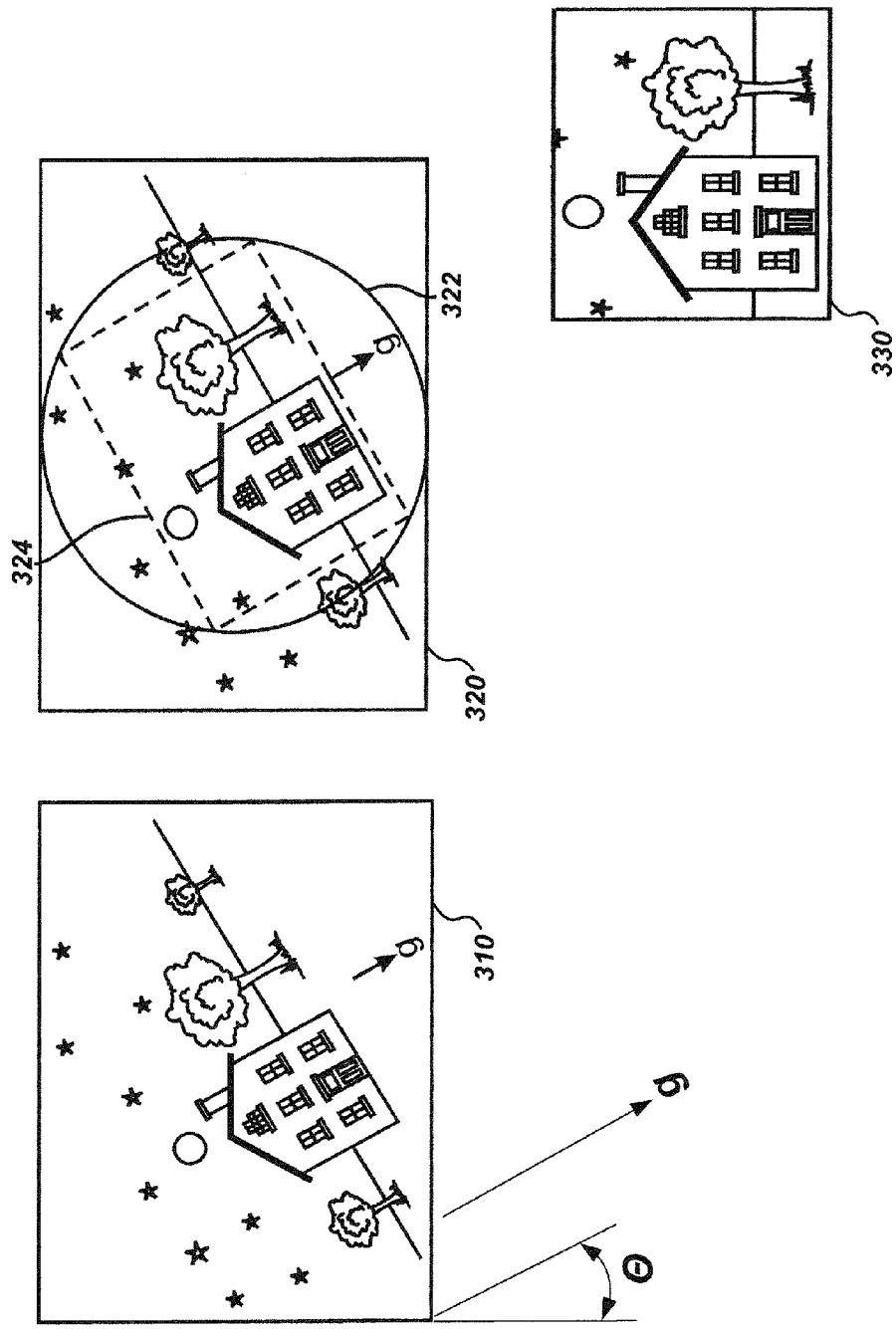
FIG. 3 illustrates details of an example image reorientation process consistent with aspects of the present invention.

In an exemplary embodiment, display module 126 is capable of rendering an orientation-adjusted output image or video corresponding to a non-adjusted or raw image or video data provided from the image sensor 112, such as on an LCD or other display element. For example, a source image, such as example source image 310 as shown in FIG. 3, may be generated and provided from image sensor 112. The source image may be rotated, at an angular orientation theta ($\Theta$) (as shown) relative to a reference orientation, which may correspond with a gravity-based vertical orientation (e.g., vertical or up-down with respect to the earth's gravitation force, g).

The orientation may be sensed by orientation module 114, such as by a three-axis accelerometer or other orientation sensor, which may provide output data or information to image processing module 116 where it may be used to generate orientation adjusted output.

It is noted that the various signal processing functions described herein may, in some embodiments, be implemented in CCUs or other electronic computing systems, however, as processing functionality improves and/or for size or other constraints, similar processing may alternately be implemented in camera heads, in whole or in part. Likewise, signal processing described herein with respect to camera heads may, in some embodiments, be similarly implemented in a CCU or other system or device communicatively coupled to the camera head.

Figure 1B:
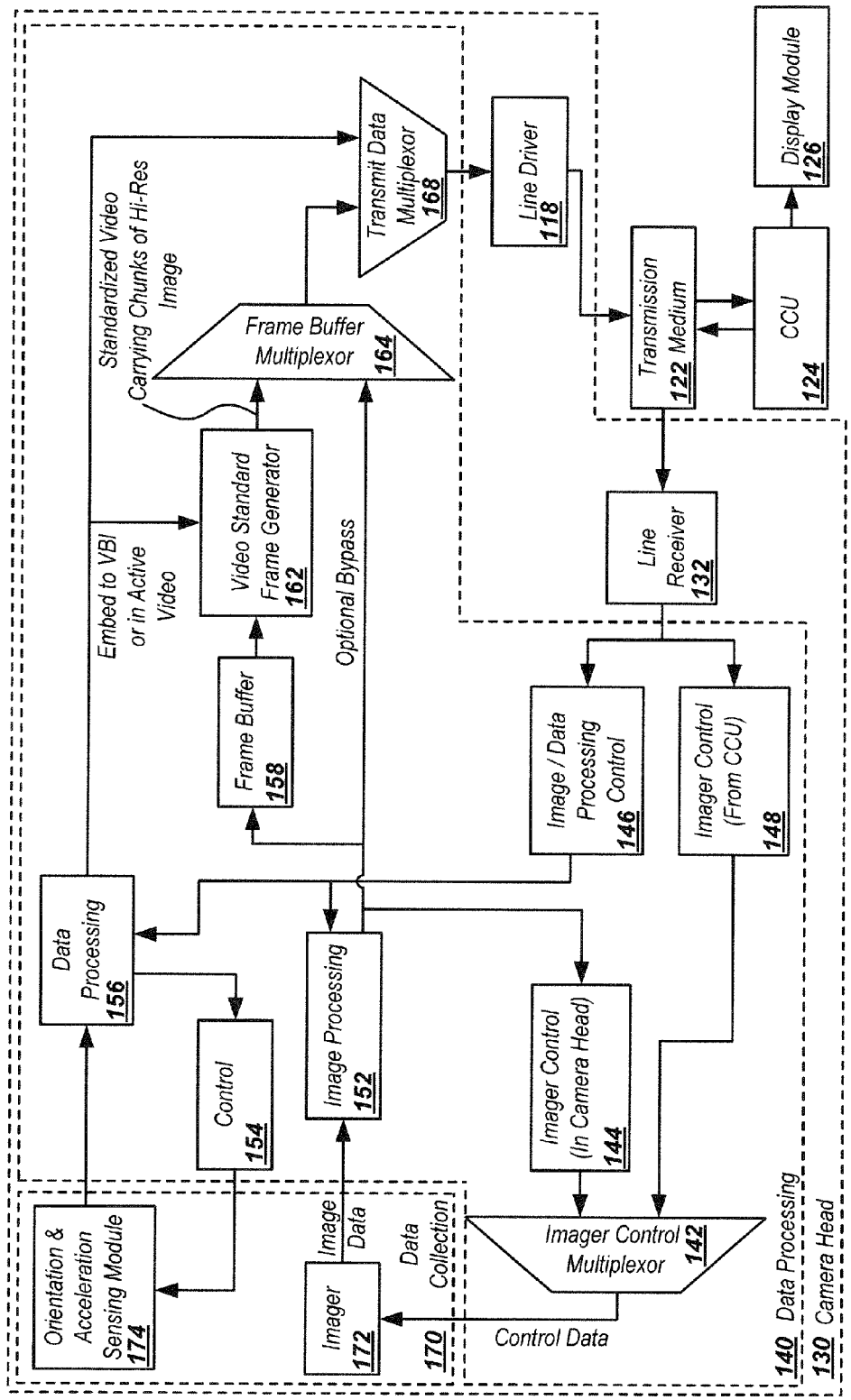
FIG. 1B is a block diagram illustrating details of an embodiment of image processing and control flow in a camera head of a pipe inspection system.

FIG. 1B is a block diagram illustrating additional details of an embodiment of example image processing and control modules in a camera head 130 of a pipe inspection system. These processing modules may be implemented using one or more processing element. Data collection module 170 (as shown in FIG. 1B) may include an image sensor 172 (or in embodiments with an image sensor array, multiple image sensors). In addition, data collection module may include an orientation and accelerations sensing module 174, which may include analog or digital sensors such as compass sensors, accelerometers, gravitational sensors, location or position sensors, and the like. Image data captured by and generated in the imager 172 may be provided to an image processing module 152. Data from sensor module 174 may be provided to a data processing module 156, which then may provide output to a control module 154 for control of the sensor module 174 (and/or other modules not shown in FIG. 1B).

Image processing module 152 may receive commands from the CCU 124, and/or processing module 152 may run autonomously in the Camera Head 130. Processed image data may be buffered in the Frame Buffer 158 for insertion in a video standard frame generator module 162 for standardized transmission, or can bypass the Frame Buffer to be transmitted as a more raw form of image data by multiplexor 164. Imager control may be autonomously determined at imager control multiplexor module 142 in the camera head by imager control module 144, and/or may be controlled by the CCU 124 via control input module 148, through the Transmission Media 122 and the Line Receiver 132.

Orientation and acceleration data from sensor module 174 may be processed and autonomously controlled in the camera head 130. Various aspects of the orientation/acceleration data processing functionality 146 may also be controlled by the CCU 124. Processed orientation/acceleration data from data processing module 156 may be embedded in the vertical or horizontal blanking interval of standardized video (NTSC, PAL, ITU-R BT.656 are some examples of video standards), or may can be opportunistically transmitted in a transmit data multiplexor 168 of image data and orientation/acceleration data to the line driver 118, or can be transmitted alone. The CCU 124 may send image information to be displayed to the display module 126.

Figure 1C:
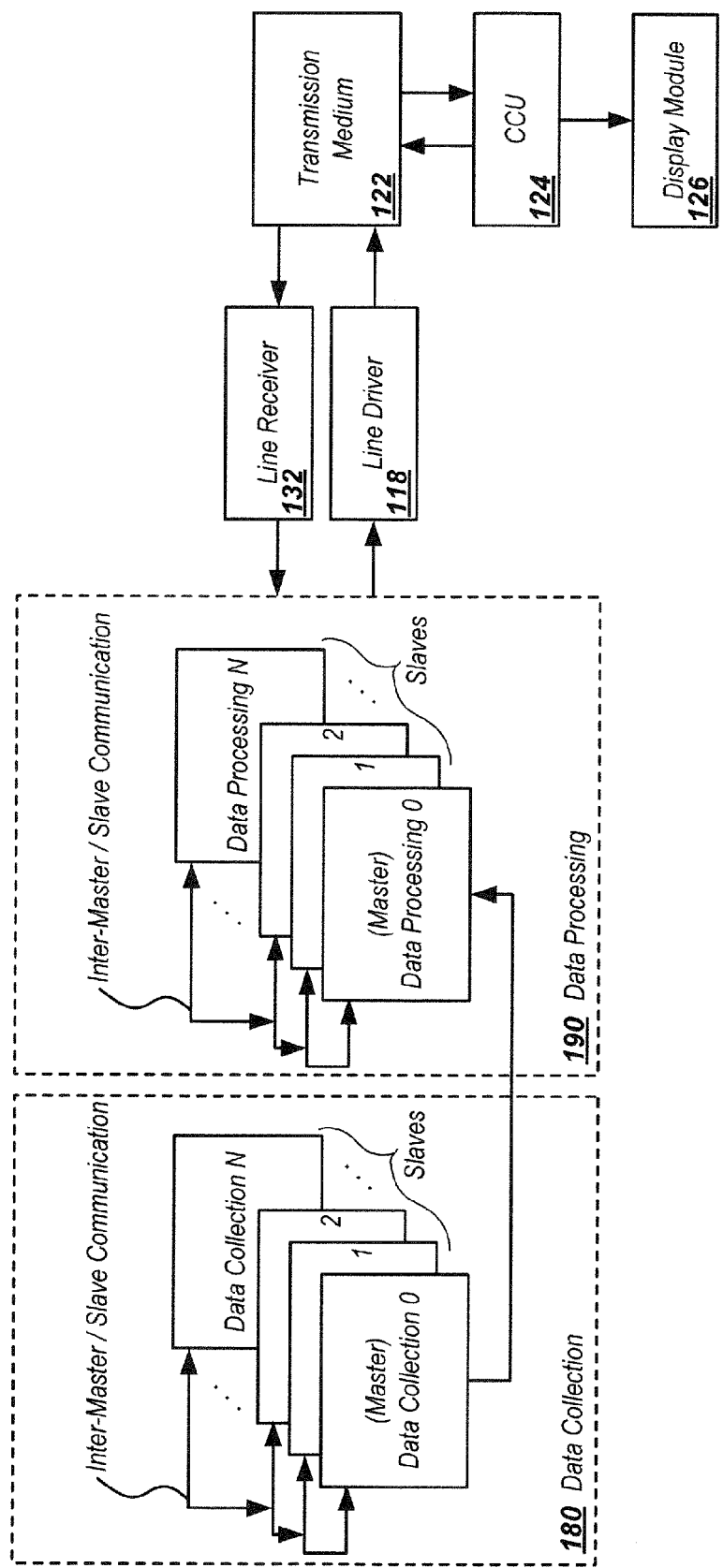
FIG. 1C is a block diagram illustrating details of multiple data sets from multiple image sensors which may be processed together in an embodiment of a single camera head.

FIG. 1C is a block diagram illustrating details of multiple data sets from multiple image sensors which may be processed together in an embodiment of a single camera head. For example, data collection element 180 may be made up of multiple instances of data collection modules 170, with one as a master and others as slaves. Data collection element 180 have a master-slave organization where data Collection 170 slaves 1, 2, 3, . . . , N may send data to the data collection 170 master to transmit to data processing element 190. Data processing element 190 may be composed of multiple data processing 140 blocks in a master-slave orientation. The Data processing 140 master may control the data processing 140 slaves and the data processing 140 slaves may transmit information to the data processing master for further processing before transmitting data to the line driver 118. The CCU 124 may control any of the data collection slaves or master through data processing element 190. The CCU 124 may control some or all of the data processing slaves or master through processes in data processing blocks 140.

Figure 2:
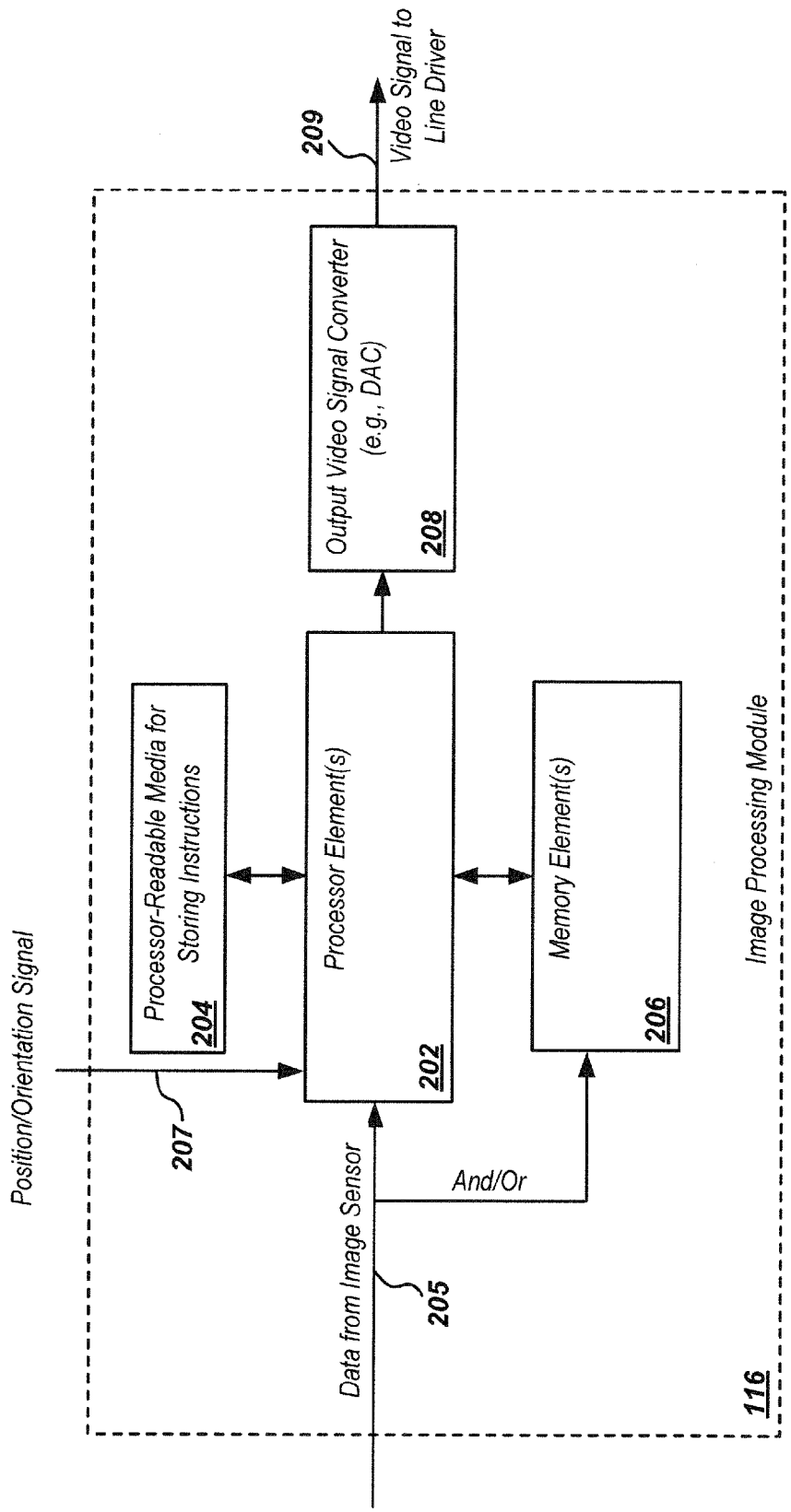
FIG. 2 illustrates details of an embodiment of a signal processing module for use in a camera head of a pipe inspection system such as shown in FIG. 1A.

FIG. 2 illustrates details of an embodiment of an image processing module such as image processing module 116 of FIGS. 1A-1C. Module 116 may include one or more processing elements 202, which may comprise microprocessors, microcontrollers, programmable logic devices, such as field programmable gate arrays (FPGAs), application specific integrated circuits (ASICs), and/or other programmable devices as are known or developed in the art, along with memory and peripheral components. In the case of a microprocessor or similar or equivalent device, storage media 204 may be incorporated within and/or coupled externally to processor element 202 so as to store and provide instructions to the processor element 202 to perform the various signal processing functions as described subsequently herein. In some cases, the instructions may be incorporated within or integral to the processor element(s) 202, such as by being implemented in logic in a device such as an FPGA.

In operation, the image processing module 116 may receive a source image or sequence of images from image sensor 112 (or, in embodiments with multiple image sensors, from two or more of the image sensors), such as via data connection 205, and store the source image, such as example source image 310 of FIG. 3, to a memory element 206, which may be, for example, a single memory array or multiple memory arrays. The data may be transferred directly to the memory element 206, such as through direct memory access (DMA) via connection 205 and/or may be received by processor element 202 and then stored in memory element 206.

Processor element 202 may then generate an output image or sequence of images, such as in the form of a sequence of images or a video signal, where the output image or video signal is orientation-adjusted relative to the source images. Examples of embodiments of processing so as to generate the orientation adjusted output image(s) are described subsequently herein.

Image processing module 116 may further include an output video signal converter module 208, which may be configured to generate, either alone or in conjunction with the processor element 202, the orientation-adjusted output image(s) or video signal. For example, in one implementation, converter 208 includes a digital-to-analog converter (DAC) configured to receive pixels corresponding to the orientation-adjusted output image(s) or video signal and convert them to an analog or digital video signal in a standard or proprietary video format. For example, in an exemplary embodiment, a digital-to-analog converter may encode binary digital data into an analog video signal, such as a composite, component, S-Video, or other analog video signal, which may be, for example, in the National Television Systems (NTSC), Phase Alternate Line (PAL) format, and/or other image or video formats known or developed in the art. In some embodiments, digital images or digital video signals may alternately be provided as an output.

The output may then be coupled to a line driver, such as line driver 118 as shown in FIGS. 1A-1C, which may then amplify and/or filter the video signal. This may be done to improve the quality of transmission of the output video signal over the transmission medium 122 to the camera control module 124 and/or display module 126. In an exemplary embodiment, transmission medium 122 is a conductor configured to carry video and/or data signals; however, in some embodiments it may be a fiber optic cable or other connection, such as a wireless connection.

After receipt of the output video signal at the CCU 124 (as shown in FIGS. 1A-1C), an output display corresponding to the orientation adjusted image or video may be provided. For example, the output may be provided by rendering the orientation adjusted video output signal on display device 126, and/or the image or video may be stored on a computer storage media, provided as hard copy, output or transmitted to another device or system, or otherwise used for analysis of the pipe, conduit, or other void or cavity being inspected. Orientation adjustment performed in and provided from the camera head, rather than in the CCU or other devices, may advantageously improve overall pipe inspection system performance, increase system flexibility, reduce CCU and display complexity, size, and/or cost, and provide other advantages.

FIG. 3 illustrates details of image processing as may be implemented, for example, by system 100 and image processing module 116 of camera head 110. Image 310 is an example source image, such as may be provided from image sensor 112. The source image may be rotated at an angle $\Theta$ relative to an orientation reference, such as a gravitational force vector g (directed downward or normal to the earth's surface). For example, if the image sensor/camera head 110 were to be rotated at angle $\Theta$ while positioned above the earth's surface, a rotated image, such as image 310 may result. While the rotation may be apparent in image 310, if such a rotation occurs while the inspection system is in a pipe, conduit or other void, the rotation may not be apparent. In this case, orientation information as may be provided from orientation module 114 may be used to generate an orientation adjusted output image(s) or video signal in the camera head.

Image 320 illustrates additional details of features associated with image 310. In particular, in an exemplary embodiment, a circular area 322 may be defined within the boundaries of source image 310. The circular area may be characterized by a circular definitional parameter, such as a radius, circumference or diameter. Within circular area 322, a sub-image area 324 may be defined. Sub-image area 324 may be a square or rectangular area, in which case a diagonal (not shown) will correspond with a line drawn along the diameter of the circular area 322, thereby allowing sub-image area 324 to fit within circular area 322 at any rotation angle. Although the example circular area 322 is shown within the boundaries of the source image 310 area, in some embodiments the circular area may optionally be larger than the image area shown, such as to provide a slightly wider angle of view in certain dimensions or to otherwise provide additional image detail or features.

Consequently, a sub-image may be generated or extracted from the source image in a square or rectangular configuration at any rotational angle. If theta is known, such as from orientation module 114, an example orientation adjusted sub-image 330 may be generated or extracted from the example source image 310.

For example, in one embodiment, the rectangular rotated sub-image area 324 may have a diagonal resolution that is less than the horizontal and vertical resolution of the image sensor; thus, the rectangular rotated sub-image area 324 may rotate within the source image to any angle within circular area 322 to give a display image area 330. For example, if a device used to capture image has an element sensor array of n×m, where n×m is 1000×1000, and a display device used to view the display image only needs 640×480 pixels, then a sub-image area 324 with a diagonal of 800 pixels may be rotated within the source image 320 to any angle, and the display image 330 (corresponding to sub-image 324) may be transmitted without resealing or cropping. Examples of methods for extracting the sub-image as an output from image processing module 116 are further described below with respect to FIG. 5.

Although the examples of FIG. 3 illustrate a sub-image area entirely within a circle within the image sensor, which may be used to provide the widest angle of imaging within the capabilities of the image sensor, in some embodiments other pixel areas within the image sensor may alternately be provided in an output image or video signal. For example, in some embodiments, a fraction of the image area, such as a half, third, quarter, etc., may be provided in the output video signal in an orientation adjusted fashion. These will generally be of a narrower angle that that shown in FIG. 3, although in some cases wider aspect ratios may be used for the output images or video signals.

Figure 4:
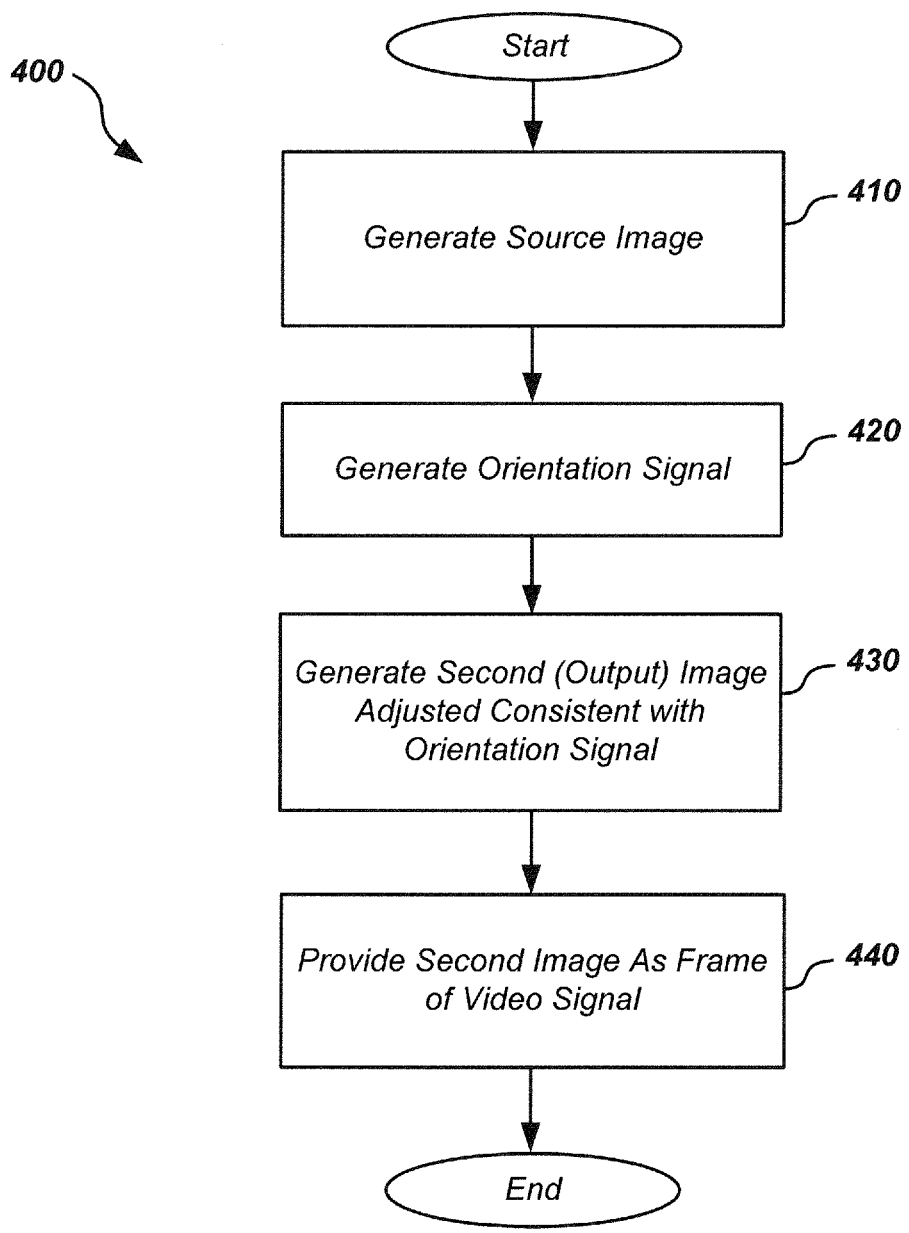
FIG. 4 illustrates details of an embodiment of a process for providing orientation adjusted images or video in a pipe inspection system such as shown in FIG. 1A.

FIG. 4 illustrates details of an embodiment of a process 400 for generating an orientation adjusted output image, sequence of images or video signal, such as example sub-image 330 shown in FIG. 3. At stage 410, a source image or images may be generated, such as described previously with respect to FIGS. 1A-1C. The source image(s) may be, for example, an image represented by a series of pixel values provided from a high definition image sensor, such as the OV9810 described previously. At stage 420, an orientation signal with orientation and/or positional data may be generated, such as from an accelerometer or other orientation or position sensing device. The orientation signal may be a gravitation orientation signal to provide an indication of offset of the imaging sensor from an up-down orientation. In some embodiments, an output sequence of images may be generated based on pixel data received from multiple image sensors, such as when a viewport is moved around a viewing area covered by multiple sensors and through overlap areas of multiple sensors. Examples of this are further described subsequently with respect to FIG. 30 through FIG. 31H.

The source image(s) and orientation signal may be provided to an image processing module, such as a stage 430, where a second or output image or images may be generated consistent with the orientation signal. Examples of various methods of generating the output signal are further described subsequently herein. At stage 440, the second or output image may be provided as an output signal, such as in the form of an image, series of images, or video signal. The video signal may be, for example, converted from a digital to an analog signal format, such as a composite video signal, component video signal, S-video signal, or other analog video signal. Data may be further embedded in the output video signal, such as in a blanking or synchronization interval in the analog video signal. The data may relate to orientation information, additional sensor information, audio data, position or motion data, position data associated with the second/output video frame sizing and/or orientation, or other data or information. In some implementations, the video output may be provided as an orientation-adjusted digital video signal.

Figure 5:
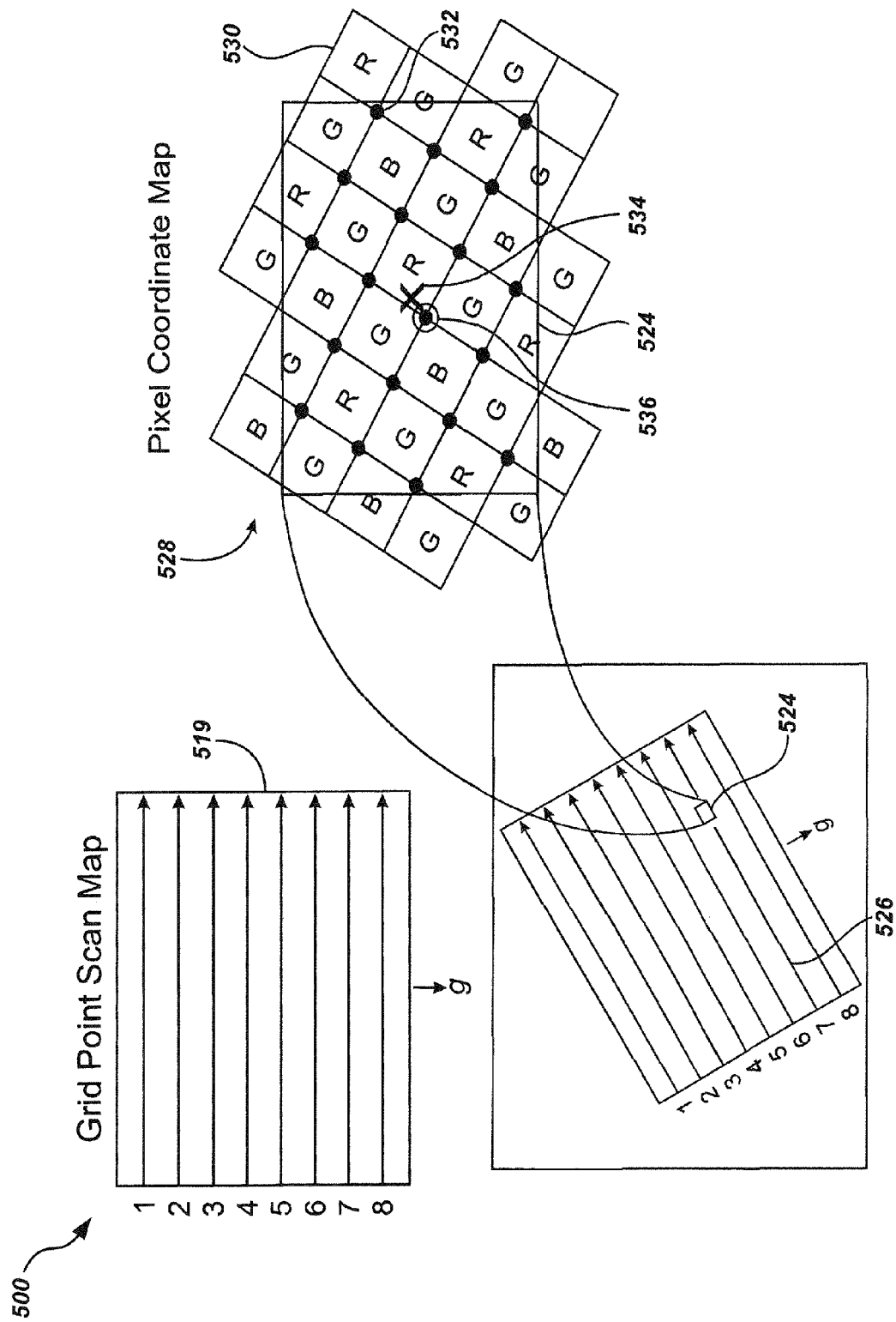
FIG. 5 illustrates details of one embodiment of signal processing to generate or extract an orientation adjusted image from a memory.

FIG. 5 illustrates details of an exemplary embodiment of image processing to generate a second or output image that is orientation adjusted relative to a first or source image. In one implementation, one or a plurality of pixel positions, such as pixel 524 (shown as representative of one of a plurality of pixels), may be determined to be used to scan a memory, such as a single memory set/memory array which may correspond with memory element 206 of FIG. 2

The basics of NTSC and PAL are similar in that a quadrature amplitude modulated (QAM) subcarrier carrying chrominance (I/Q) information is added to the luminance (Y) video signal to form a composite video baseband signal. For example, chrominance may be encoded using two 3.579545 MHz signals that are 90 degrees out of phase to each other, known as in-phase (I) and quadrature (Q). These two signals, I and Q, are amplitude modulated, and added together. The pixel positions for a composite output exist as points in time, and an instantaneous position of the continuously scanning beam. Luminance (Y) and chrominance (I/Q) may be encoded from a plurality of scan lines 526 to produce an output image (which may correspond with image 330 of FIG. 3).

In one implementation, a pixel coordinate map 528 may be used to illustrate the pixels from an image sensor, such as image sensor 112. The image sensor may include a Bayer filter to determine the color and intensity of virtual image pixel 524, which may be extracted from or determined by elements of the pixel coordinate map 528, such as by selecting values of one or more of the elements of coordinate map 528 and/or by generating the virtual image pixel as a function of one or more element values of the coordinate map. The Bayer filter is a pattern of individual filters, each of which are denoted with one letter selected from "R", "G", and "B" to indicate a red, a green, and a blue light transmission characteristic, respectively (see, for example, U.S. Pat. No. 3,971, 065 of Bayer, the content of which is incorporated by reference herein in its entirety). The precise geometry of the virtual image pixels 524 can be mapped onto a grid 530 of fully and partially covered RGB array of the image sensor, where the virtual pixels may be represented by color and intensity values, with the color and intensity of the virtual image pixels 524 depending on its positioning on the grid 530. A coordinate 532 may be indicated at the vertex of a 2×2 RGB pixel block (and/or by a single pixel or other pixel block configurations) falling within or in proximity to one of the virtual image pixels 524. In one implementation, pixels may be selected for the virtual image based on a nearest neighbor or other vicinity mapping from the coordinate map to the virtual image pixel. Alternately, or in addition, pixel blocks may be averaged to calculate a color and an intensity associated with each of the virtual image pixels 524.

A centroid 534 may be determined and used to indicate a geometric center of the virtual image pixels 524. A neighboring coordinate 536 may be determined based on a relative location to the vertex of the pixel block nearest to the centroid 534. This neighboring coordinate 536 may be used to serve as the color and the intensity input for the virtual image pixels 524. In this case, processing some or all of the image pixels within the area of virtual pixel 524 may improve signal to noise ratio in the output image, which may subsequently improve the image and/or video quality at the display device or on a stored image or video signal.

In one exemplary embodiment, it may be desirable to have the diagonal of the rotated image be as close to the limiting dimension of the image sensor as is mathematically possible. This may be done to generate an output video signal with the widest field or angle of coverage. As shown in FIG. 3, the diagonal may be selected to correspond to the diameter of the circular area 322, however, in some cases, a larger diagonal may be selected so as to provide slight cropping at the corners of the rotated image. For example, a diagonal size may be selected to be slightly larger than the diameter of circle 322. In some embodiments, the centroid may be offset in one or both directions from the center of the image sensor, such as to image details or features offset from the center.

Alternately, or in addition, the diagonal size may be further selected based on the orientation signal provided from the accelerometer or other orientation sensor. In this case, if the image is only slightly rotated, the diagonal size may be selected to be larger as there will be less image cropping at the edges (compared to, for example, 90 degree rotation). As such, the size of the subset of pixels (e.g., number of pixels in the subset) may be based at least in part on the orientation signal, with more pixels used in the case of orientations close to the vertical. For example, if the image sensor is oriented at or close to vertical (e.g., the image from the image sensor is only slightly rotated from a level orientation) the size of the subset of pixels used may be larger than if the image sensor is rotated at a greater angle, which will then allow for a greater angle of coverage on the output video signal. Conversely, at the extreme, with a rectangular image sensor, the smallest pixel subset size would be selected when the sensor is rotated in the range of 90 degrees or 270 degrees, which would provide a narrower angle of coverage.

In some implementations, for maximum usable field of view, the diagonal of the rotated sub-image (in the pixel space of the high resolution image the virtual pixels of the transmitted image may be larger and fewer in number) may be approximately equal to the smallest of (m,n) of the high resolution image. In some implementations it may be desirable to slightly crop the corners of the rotated sub-image so as to maximize the field of view of the image inside the pipe, conduit, or other cavity.

In some implementations, output image size may be determined in accordance with a relationship such as $\lceil \sqrt{(p^2+q^2)} \rceil < (m,n)$. In another implementation, output image size may be determined in accordance with the relationship $\lceil \sqrt{(p^2+q^2)} \rceil < (m,n)/2$ or $\lceil \sqrt{(p^2+q^2)} \rceil < (m,n)/5$ (where "⌈" and "⌉" indicate an "upper ceiling"). Other output sizes may be used in various other embodiments.

Processing in RGB color space is generally inefficient and consumes substantial memory resources. Thus, to reduce consumption of memory resources, RGB color space may be converted directly to NTSC color space for transmission as a composite video output signal, such as is illustrated with respect to FIGS. 1A-1C and FIG. 2. For example, RGB color space may be converted directly to YCbCr color space for digital image processing; however, 4:1:1, 4:2:0, or 4:2:2 YCbCr data may be converted to 4:4:4 YCbCr data before undergoing conversion to NTSC or PAL signal format (YIQ or YUV). The transformations between each color space as disclosed herein, may be carried out by methods known to one of skill in the art and routine modifications thereof, and/or according to procedures found in, for example, U.S. Pat. No. 7,015,962 of Acharya; U.S. Pat. No. 7,015,962 of Raffy et al.; and Jack, K. "Video Demystified", 2005, pp. 15-34 and 394-471, each of which is incorporated by reference herein.

In various embodiments, a color space transformation, such as YCbCr, YUV, or YIQ or chroma sub-sampling, such as 4:2:2, 4:2:0, or 4:1:1 may be used to produce an appropriate video output. These transformations and/or sub-sampling may be performed before or after the image (e.g., plurality of pixels) is stored in a memory such as memory element 206.

In another aspect, the disclosure relates to a camera head and associated display system device, such as a camera control unit (CCU) or other device configured to provide, display, and/or store variable and/or adjustable resolution images and videos during an inspection operation such as a buried pipe inspection. The various aspects described below may be implemented separately in some embodiments or may be combined with the level-adjustment and related embodiments described previously herein. In some embodiments, an output sequence of images may be generated based on pixel data received from multiple image sensors, such as when a viewport is moved around a viewing area covered by multiple sensors and through overlap areas of multiple sensors. Examples of this are further described subsequently with respect to FIG. 30 through FIG. 31H.

Figure 6:
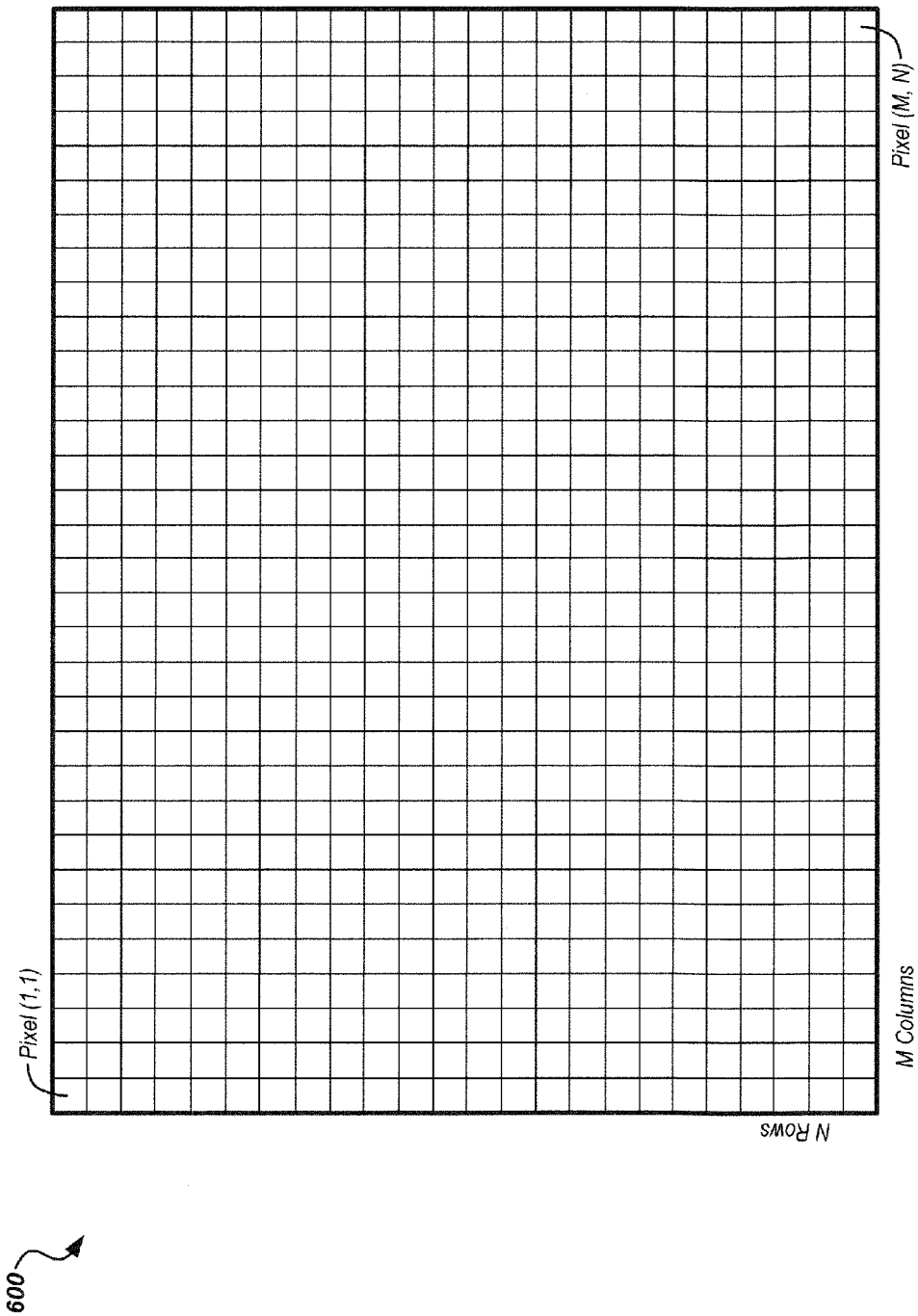
FIG. 6 illustrates details of an image sensor configuration that may be used to generate tiled image or video data.

Turning to FIG. 6, an example high resolution image sensor 600 is illustrated. Image sensor 600 may be a CMOS or CCD sensor or other image sensor type as known or developed in the art. Image sensor 600 includes multiple pixels (typically on the order of 5-20 million pixels or megapixels) configured in a N rows by M columns M and N may be equal in some sensor embodiments or may be different numbers depending on the sensor type, nominal aspect, ratio, etc. The pixels of sensor array 600 may correspond directly with output pixels or may be mapped, such as using a Bayer pattern or other sensor pixel mapping to corresponding output pixels. For purposes of explanation, it is assumed that the pixels as shown in example array 600 correspond directly with the same number of output pixels, however, this relationship may be varied through use of interpolation, color grids on top of the sensor elements, or other sensor processing techniques known or developed in the art.

Figure 7:
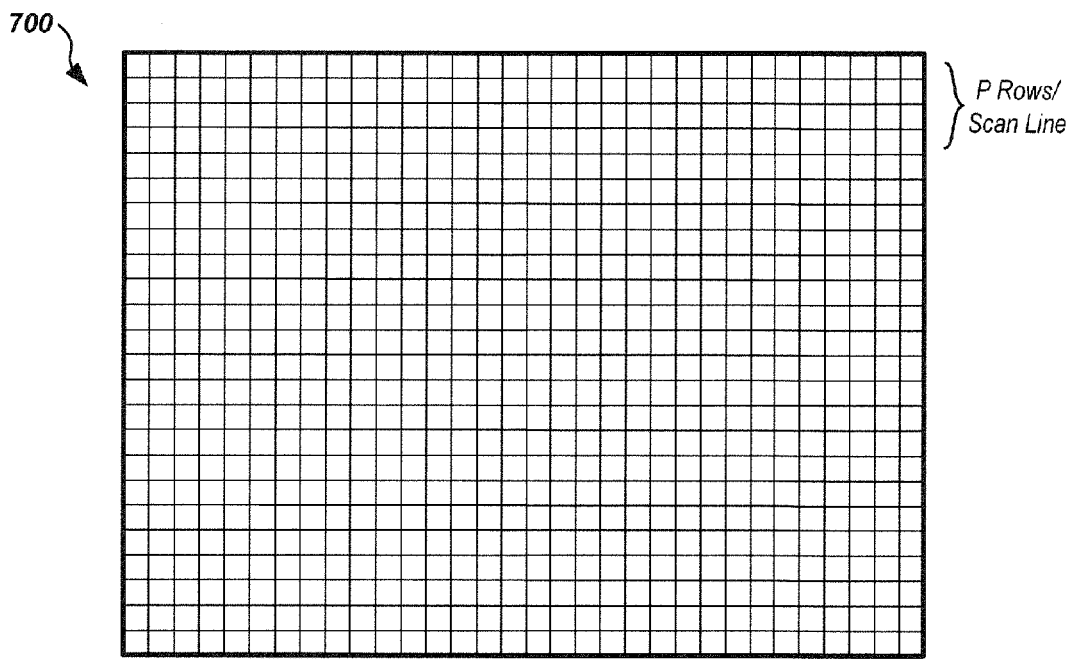
FIGS. 7 & 8 illustrate details of the image sensor of FIG. 6 and a corresponding scanned analog video frame.
Figure 8:
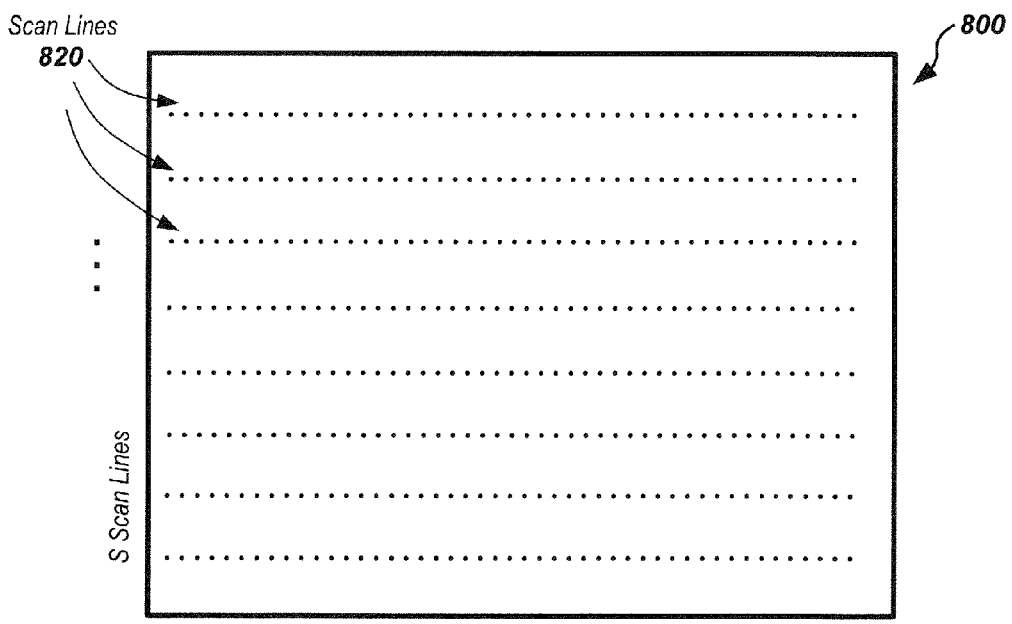

In operation, the sensor array pixels may be mapped to corresponding scan lines of an image or video frame. An example of this is shown in FIGS. 7 & 8, where FIG. 7 illustrates the sensor array 600 and corresponding pixels, while FIG. 8 illustrates a frame or sub-frame 800 of a scanned analog video frame corresponding with image data generated from the sensor. Frame 800 includes a plurality, S, of scan lines 820, which may be scan lines of standard video formats such as NTSC, PAL, SECAM, and the like. The scan lines may be interlaced or progressive, depending on the video format used. In some embodiments, the scanned lines may be digital equivalents of the analog video scan lines.

A subset of the image sensor pixels as shown in FIG. 7 as P rows per scan line may be converted to generate ones of the scan lines 820. For example, when the image sensor resolution is substantially larger than the corresponding resolution of the scanned video, as may be the case when converting megapixel sensor data to standardized frame resolutions such as 640×480, multiple rows, P, may be combined to generate each scan line. Other conversion methods between digital pixel values and corresponding analog lines of video may also be used in various embodiments.

Figure 9A:
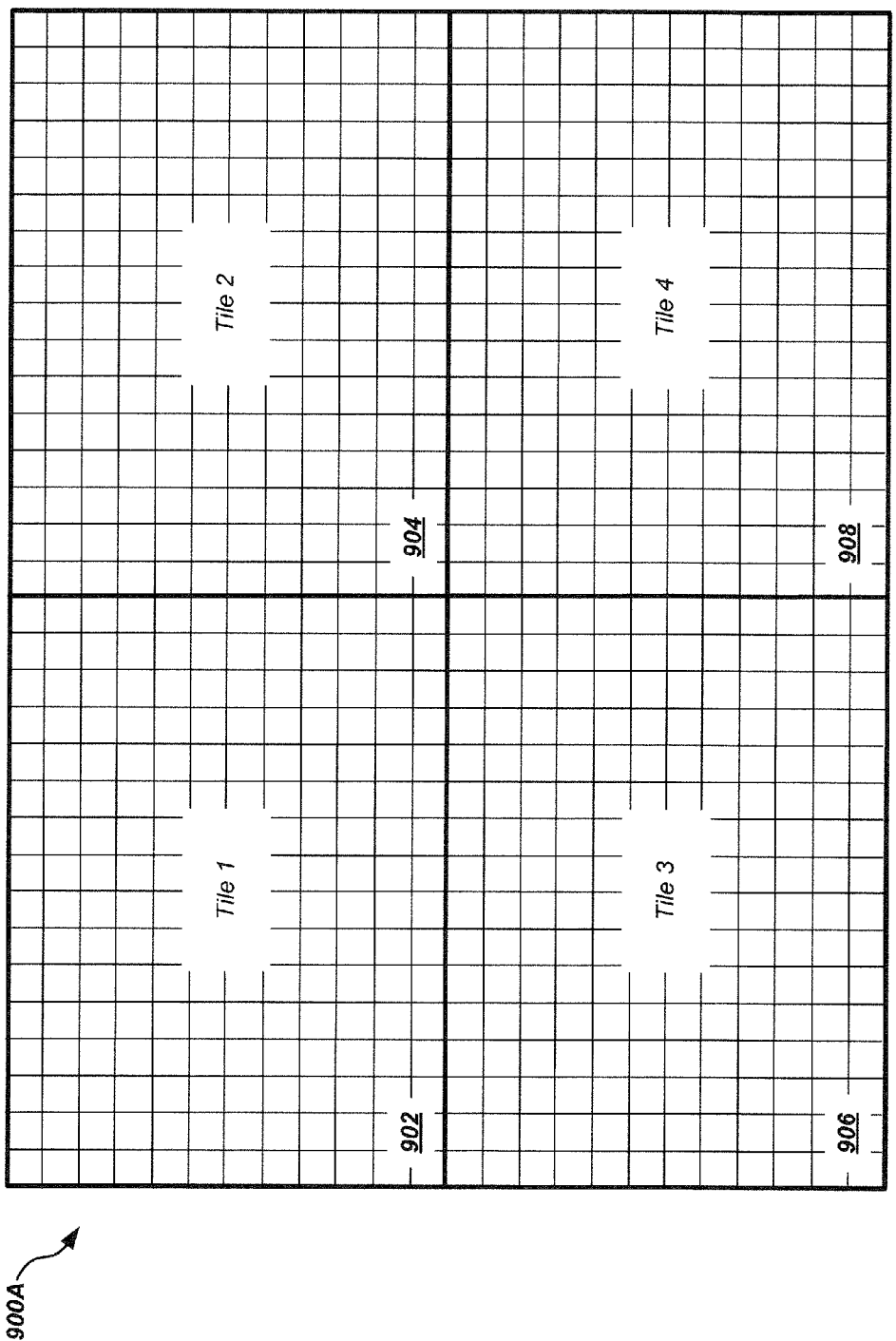
FIG. 9A illustrates details of example tiling of the pixels of the image sensor of FIG. 6.
Figure 9B:
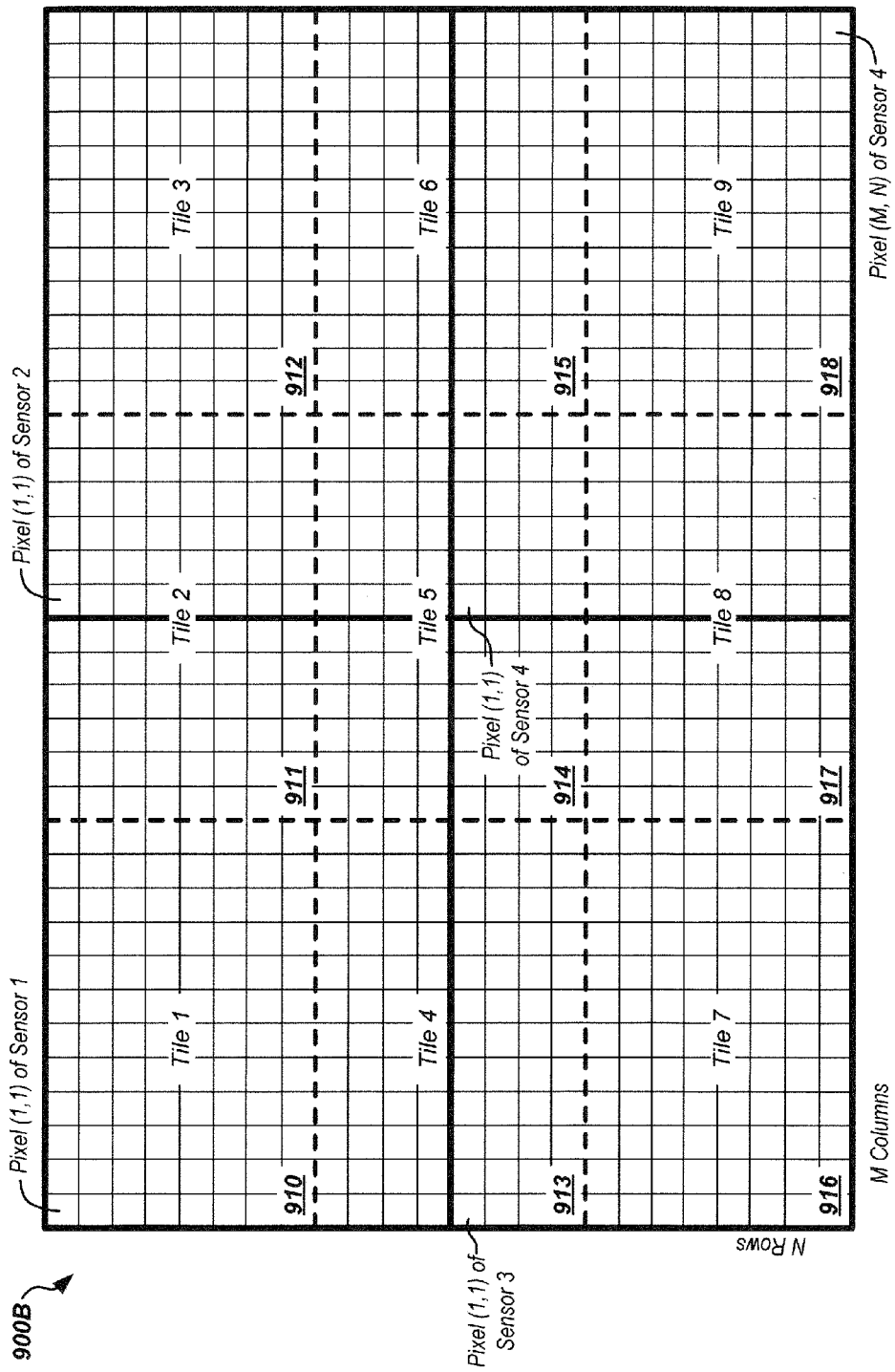
FIG. 9B illustrates details of a multi sensor array subdivided into nine tiles.

In various embodiments, the full field of the image sensor (or image sensor array), or, in some implementations, a portion of the full field of the image sensor, may be sub-divided into one or more tiles. This may be done in implementations using a single image sensor (such as shown in FIG. 9A) or, in some embodiments, implementations using multiple image sensors in an image sensor array (such as shown in FIG. 9B). Each tile can be viewed as a collection of pixels of the image sensor (or image sensor array). In implementations using a multi-sensor array, reference markers, such as light markers in the form of dots or symbols, may be projected on the area being observed to allow combination of data from multiple sensors.

For example, as shown in FIG. 9A, the field of a single image sensor 600 may be divided into four tiles, denoted as tiles 902, 904, 906, and 908 (with example pixels shown as squares—the size and number of pixels in FIG. 9A are shown larger than they would typically be for clarity. Further, a real image sensor would typically have many more pixels than the number of squares shown). In other embodiments, different numbers of tiles may be used depending on the resolution of the image sensor and/or the desired output resolution. For example, the image sensor field may be divided into 9 tiles, 16 tiles, or other tiled configurations in various embodiments. In some cases the tiling may be non-symmetric, e.g., the field may be divided into 2 tiles, 6 tiles, etc., depending on the image sensor type and/or desired output resolution in either the horizontal dimension, vertical dimension, or both, as well as the desired aspect ratio. While square pixels are shown, in some embodiments other pixel shapes may be used depending on the configuration of the image sensor. For purposes of explanation, a four tile configuration will be described subsequently, however, it is not intended that the tiling configurations be limited to four tiles—other configurations can also be used in various embodiments.

In some embodiments, image sensors may be grouped into an array of two or more sensors (also denoted herein as an image sensor array or multi-sensor array). These arrays may be in various configurations including pluralities of image sensors. For example, FIG. 9B illustrates details of a multi-sensor array 900B including 4 image sensors, shown as image sensors 1 through 4, with the array having M×N pixels. In this image sensor array, the center of the array is located adjacent to pixel (1,1) of sensor 4 (where the pixel coordinates begin at the upper left of each image sensor). The image sensor array may be subdivided into multiple tiles, such as, for example, the nine tile configuration of FIG. 9B, where the tiles are denoted as tiles 910 through 918.

Image and video capture and processing methods as described herein may also be implemented in a camera head using an image sensor array having a plurality of image sensors. In addition, output images and video may be generated based on pixels from multiple image sensors, which may be stitched together in a processing element of the camera head and/or a coupled CCU or other computing device or system. The stitching may be aided with references, such as unique characteristics or features of the area being imaged and/or using projected light markers or other references. In addition, panning, zooming, rotation, and/or other operations may be implemented across image sensors in an image sensor array. This may be done either by combining pixels from multiple sensors or dynamically switching, such as on a detected sensor area transition or overlap area, from pixels on one sensors to pixels on other sensors.

Figure 9C:
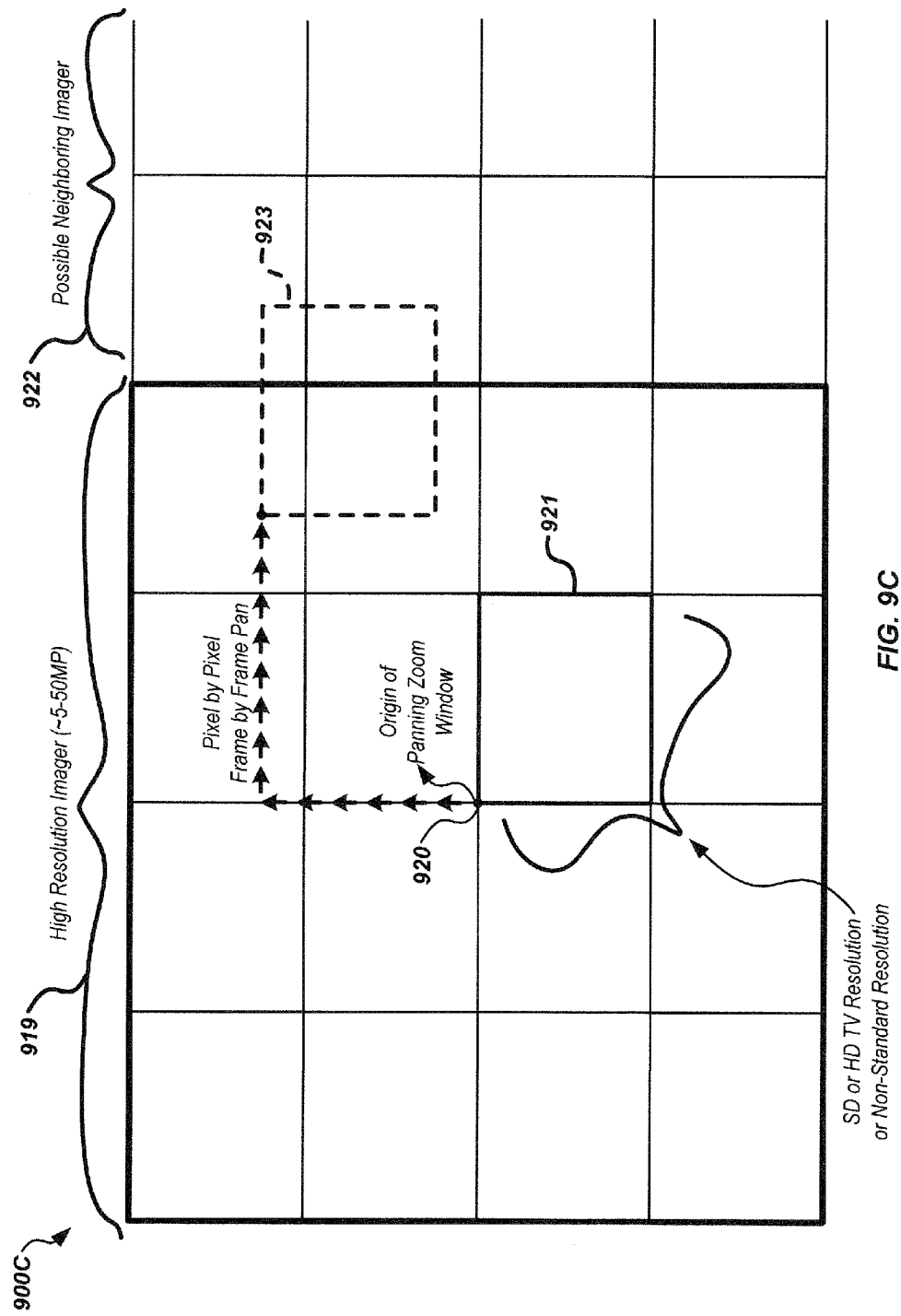
FIG. 9C illustrates details of an exemplary 4× zoom/pan video using one or more imagers.

For example, FIG. 9C illustrates details of a zoom operation and the corresponding initial tile viewport 921 and final tile viewport 923 (the viewports may be viewed as the area of view from which output images and/or video are taken at a particular time). Two image sensors of image sensor array 900C are shown in FIG. 9C (i.e., imager 919 and 922), and tiles may be defined as a subset of the image sensor (or image sensor array) to form an output viewport (e.g., an area of the imager that will be provided as an output, such as on a CCU display or other video display device, stored in memory as images or video, and the like).

In a typical configuration, output date from the pixels of the image sensors may be stored in a memory, such as in a mapped memory in the imager or in a separate processing element or other module of the camera head and/or CCU. Output signals may be generated by extracting appropriate pixels from the memory and then processing them to provide the desired output signals. During image processing operations, such as based on positioning, location, or orientation information provided by sensors on the camera head (e.g., leveling outputs, etc.) and/or based on control signals provided from the CCU or other coupled control device, the viewport position and corresponding viewed area within the pipe or other area being inspected may be changed. With the imaging sensor array fixed in position (relative to the pipe or other object under inspection), digital articulation of the camera head may be implemented by moving the viewport around (i.e., by changing the pixels used to generate the output and/or interpolating between pixels or discarding pixels) the pixels of the imaging sensor array. Similar articulation operations may also be done while the camera head is being moved, such as while the camera head is being moved into or out of a pipe under inspection.

For example, as shown in FIG. 9C, the viewport area may be moved from the initial area 921 to area 923 by using the pixels on the path shown, which may be incremented pixel by pixel or by other increments (e.g., by multiple pixels for faster panning, etc.), to move from position 921 to position 923. In this example, output pixels from multiple image sensors (e.g., sensor 919 and sensor 922) may be used to generate the resultant output image from viewport 923. The pixels of the multiple sensors may be registered to determine boundaries using light markers (not shown in FIG. 9C), such as laser projected dots or other markers.

In addition to the X and Y translations around the image sensor array shown in FIG. 9C, zoom operations (i.e. in or out) as well as rotate operations may be done on the output viewport. The output viewport may be set at a standard format, such as a standard SD or HD resolution, or, in some embodiments, in a non-standard format. Movements of the viewport may be done in response to camera head movement, such as movements sensed by orientation, position, and/or location sensors, and/or in response to control commands from a CCU or other coupled control system.

In configurations with a single image sensor, the translation, zoom, rotation, and other operations may be done within image sensor boundaries. Alternately, in configurations with multiple image sensors such as shown in FIG. 9C, the translation, zoom, rotation, and other operations may be done across image sensor boundaries. For example, the final output image viewport of tile 923 may be a combination of pixels from image sensor 919 and image sensor 922. Alternately, when multiple imagers are used, the output may be selectively switched from pixels from one imager to those of another imager (such as by extracting corresponding data values from the pixel array memory) upon transition from one image sensor to another image sensor. As noted previously, the sensors may be registered based on features of the area being inspected, and/or based on projected light markers such as dots, or other registration mechanisms. The data corresponding with the viewport may be stored in a frame buffer, such as frame buffer 158 and may be output using frame buffer 158 and a video standard frame generator 162, such as through a transmit data multiplexor 168, line driver 118, and transmission medium 122 to CCU 124 (as shown in FIG. 1A through 1C).

In some embodiments, multiple images, either from a single image sensor or, in some implementations, multiple image sensors, may be combined either in the camera head or CCU to create a high-dynamic range (HDR) image. This may be done by combining images from overlapping viewed areas of the image sensor or from multiple exposures taken from a single image sensor. These HDR images may then be used to generate an HDR data stream, such as in the form of video based on the HDR processing.

HDR images are typically created by capturing multiple images of a particular area at different exposures, and intelligently combining the exposures to retain detail in both the highlight and shadow areas. This may be done by adjusting the luminance and chrominance of the multiple images to approximate how the image is seen by the human eye. The multiple images, of limited dynamic range, may be additively combined into a single image that yields a high contrast, computationally created with detail in both the highlight and shadow areas, and tone mapping may be applied. Example methods and apparatus for capturing and processing HDR images and video are described in, for example, U.S. Pat. No. 8,072,503, entitled METHODS, APPARATUS, SYSTEMS, AND COMPUTER PROGRAM PRODUCTS FOR REAL-TIME HIGH DYNAMIC RANGE IMAGING, U.S. Pat. No. 8,159,579, entitled HIGH DYNAMIC RANGE VIDEO, U.S. Pat. No. 7,680,359, entitled METHODS FOR MERGING DIGITAL IMAGES TO OBTAIN A HIGH DYNAMIC RANGE DIGITAL IMAGE, as well as a number of other patents and patent publications. The content of each of the above-described patents are incorporated by reference herein.

FIG. 9D illustrates an embodiment of an image sensor array 900D and associated processing that may be used to generate HDR images and corresponding video streams (based on the images). In the example array 900D, the four image sensors (imagers 0 through 3) are oriented and include optics such that they image an overlapping area of the scene being viewed (denoted as the overlapping field of view in FIG. 9D). to generate an HDR image, the scene may be simultaneously imaged by each of the sensors, with the exposure of each adjusted to different values to capture different areas of light and dark in the scene being viewed. For example, as shown, imager 0 is set at a low gain value, image 3 is set at a high gain value, and imagers 1 and 2 are set at in-between values. The output data from each of the imagers may then be combined in a processing module 928, such as through use of image processing detailed in the above-described incorporated applications, to generate a series of output HDR images and/or HDR video comprising a sequence of the images. Other methods may also be used, such as sequentially sampling the scene by cycling through the imagers (assuming the area being viewed is not changing significantly) to generate the output image. It is noted that the multi-imager method may best be used where the area being viewed is relatively distant from the image sensors, since each will see a slightly different view of the area being imaged. Alternately, in embodiments with a single image sensor, multiple exposures may be captured sequentially, and then subsequently combined to generate a single HDR image, or series of images that may be combined in a video stream. In some embodiments, the imager gain or exposure can be changed on a frame by frame basis by imager control 144 or imager control 148 (as shown in FIG. 1B), to generate a series of different exposures of an image only slightly delayed in time. For example, a series of three exposures can be taken repeatedly at 90 frames per second, stored in the frame buffer 158, and extracted so that the optimal exposure of each region of the three frame segments are represented in the video stream at 30 frames per second, or the three frames may be combined in a weighted average to generate a video stream at 30 frames per second.

Figure 21:
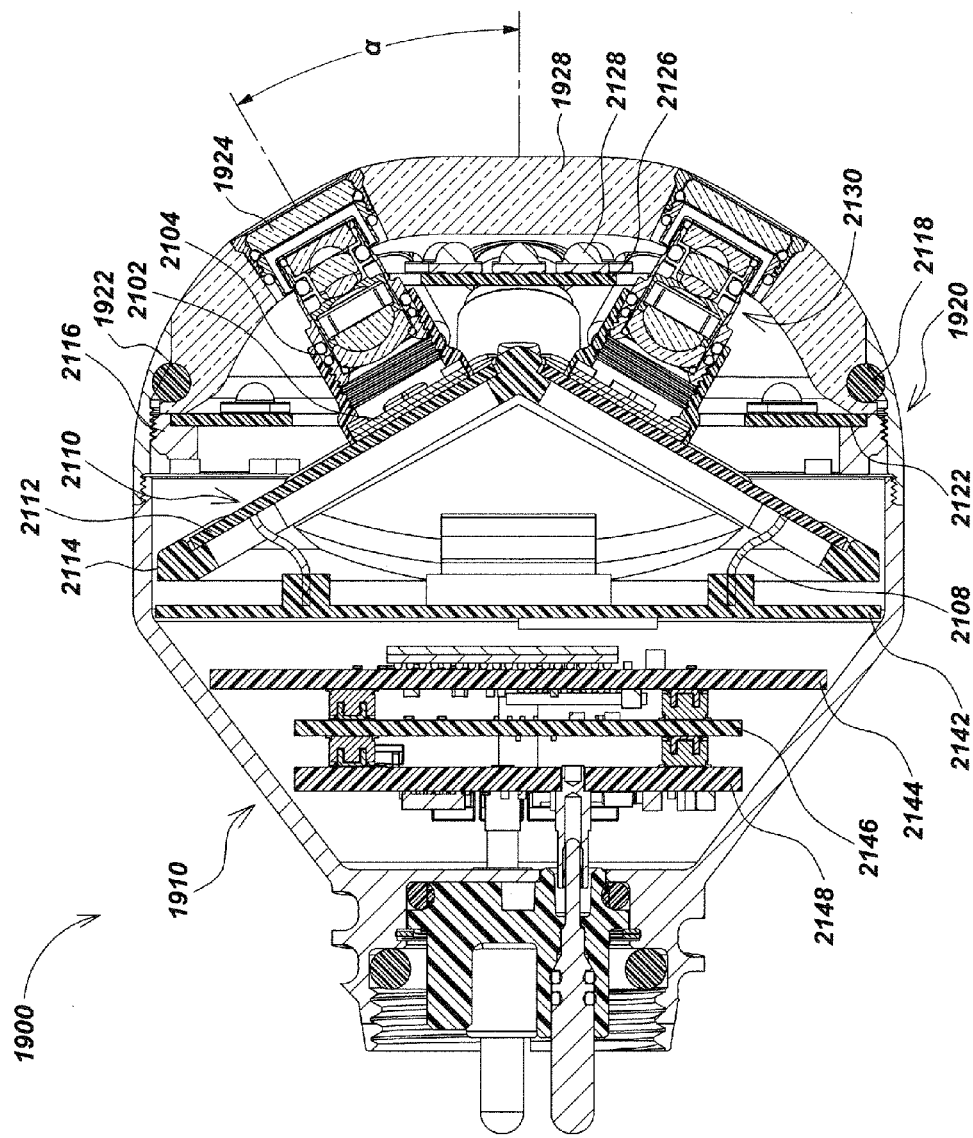
FIG. 21 is a section view of the camera head embodiment of FIG. 20, taken from line 21-21 (through imagers)
Figure 22:
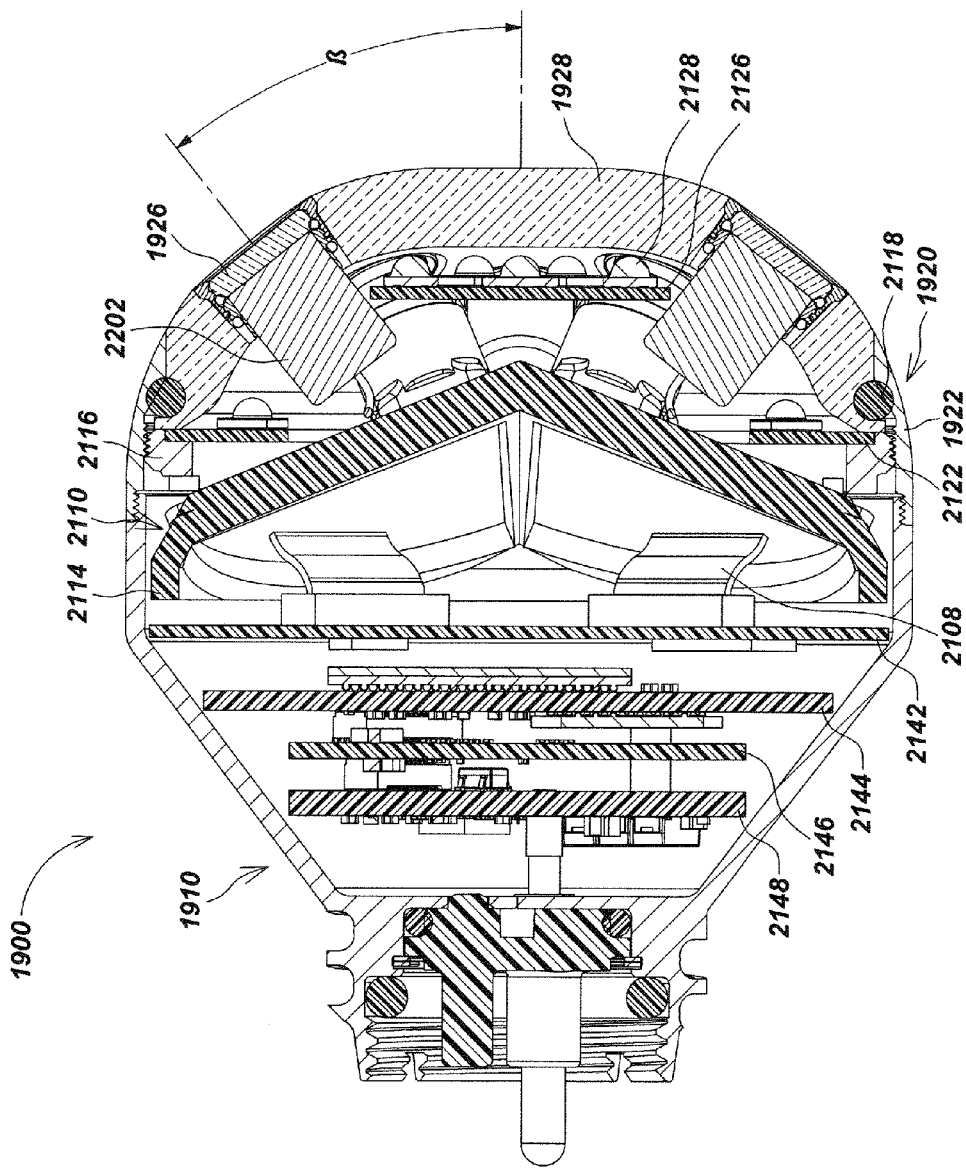
FIG. 22 is a section view of the camera head embodiment of FIG. 20, taken from line 22-22 (through lasers)
Figure 23:
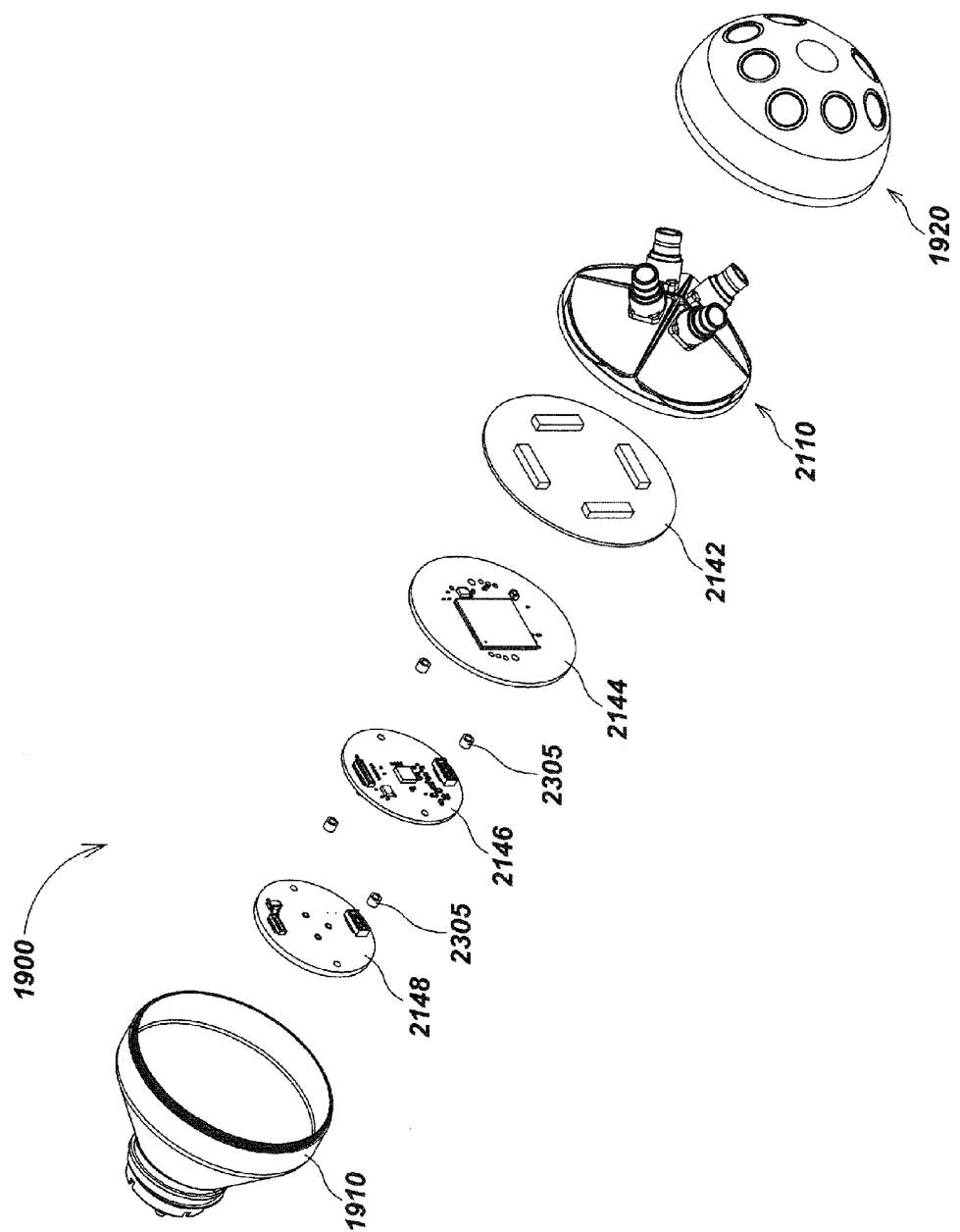
FIG. 23 is an exploded view of the camera head embodiment of FIG. 20.

In addition to HDR image processing, in some embodiments, images from two or more image sensors of an image sensor array may be captured and processed to generate stereoscopic output data, such as in the form of stereoscopic pairs that are viewable on traditional stereoscopic viewing displays as two separate images, and/or on newer stereoscopic viewing displays that are configured to simultaneously or switchedly provide separate left and right images or video frames from a single display. In this operating mode, images may be captured from two different image sensors and, since the image sensors are offset in position from each other, the images can be combined to generate stereo pairs and/or stereoscopic video streams. In some embodiments, the image sensors may be oriented such that their optical axis is parallel, however, in an exemplary embodiment the optical axes of the image sensors and associated optics, which may be denoted as an imaging element, are non-parallel. For example, FIGS. 21-23 illustrate an exemplary embodiment wherein the image sensors and optics are oriented with divergent optical axes. In this configuration, stereo pairs and/or stereo video streams may be generated in the camera head using a plurality of imaging elements having non-parallel optical axes.

In addition, captured stereo pairs and/or video can be used to generate a 3D model or reconstruction of the pipe under inspection, such as by capturing sequences of pairs while moving through a pipe and combining these captured pairs to generate a model, such as a wireframe or other computer aided design (CAD) model representative of the interior of the pipe. Methods and apparatus for generating 3D models from stereoscopic images are described in, for example, United States Patent Application Publication 20100284607, entitled METHOD AND SYSTEM FOR GENERATING A 3D MODEL FROM IMAGES, United States Patent Application Publication 20080112610, entitled SYSTEM AND METHOD FOR 3D MODEL GENERATION, U.S. Pat. No. 5,633,995, entitled CAMERA SYSTEM & METHODS FOR EXTRACTING 3D MODEL OF VIEWED OBJECT, U.S. Pat. No. 8,031,909, entitled METHOD AND APPARATUS FOR PRODUCING 3D MODEL OF AN UNDERGROUND ENVIRONMENT, as well as various other references in the art. The content of the above-described patents and patent publications are incorporated by reference herein. Modeled information may include, for example, shapes of interior pipe (or other object) features, dimensions, textures, and the like. Acoustic or other sensing may also be combined with optical information to generate the models.

In some embodiments, images may be captured from multiple sensors and either processed directly in the camera head (as processing power improves) and/or transferred to a CCU. If NTSC video formatting is used, standard frame rates would allow transmission of one tile or viewport area data in 1/30 of a second. A 5 MP image could be sent as tiles in approximately half a second, and with four imagers all four images could be sent in about two seconds. If 64 tiles are sent at 30 frames per second, based on indexing of tiles and laser dots or other markers in the images, the tiles can be processed to generate a 3D model. In some implementations, a low resolution context image may be initially sent, and then tiled images may subsequently be sent. Alternately, if tiles are sent, they may be binned together at the CCU and then tiled down, depending on available processing power in the camera head and CCU. Further, a standardized video format, such as NTSC, PAL, etc., can be used as a video pipe (e.g., image data may be sent by using the analog video channel to create a digital pipe within the video portions of the signal (as opposed to schemes that use the blanking area of the video signal for data transmission). Further, raw Bayer sensor data or other data or information may be sent via such a pipeline (e.g., sending raw image sensor data through the NTSC or other standard analog video channel). Details of this concept are further illustrated in the example embodiment illustrated in FIG. 9F.

In some implementations where features of the area being viewed are known, such as within a pipe where the pipe is cylindrical and has a circular or oval cross-section, light markers, such as laser dots or other projected markers, can be used as a predictive model to provide size, centerline orientation and pointing direction, and/or other information to contribute to the model and/or selectively transition the output from one image sensor of an image sensor array to another image sensor.

Likewise, when camera heads with optical elements using wide angle lenses and diverging optical axes are used, images can be generated by stitching together pixels from multiple image sensors to generate an extreme wide angle field of view, such as a field of view of greater than 180 degrees. The stitching may be aided by light markers projected onto the area being viewed, such as laser dots or other light markings, and/or by recognizing common features seen from multiple imagers and combining the pixels to overlap in the areas of these features. Further, projected dots or markers may then be processed out of the resultant images or video based on location and/or distinguishing characteristics, such as color (e.g., bright red laser dots), shape, size, etc.

Alternately, or in addition, strobed light markers may be used, such as in synchronization with the image sensor frame rate or other imaging parameters, so that only some frames are captured when the dots or other markers are projected. For example, laser dots or other markers may be strobed such that they are imaged only in alternating frames or in other specific frames (e.g., every $4^{th}$ frame, $30^{th}$ frame, etc.). This may be used to allow capture of frames both with the markers (e.g., with red or other dots, grids, or other marker shapes) and without the markers so as to facilitate presenting output and/or storing images or video that do not include the markers. This may further allow removal of dots or other markers by combining images having markers in them with previous or subsequent images without the markers during image processing in the camera head, CCU, or other electronic computing device or system.

Figure 9E:
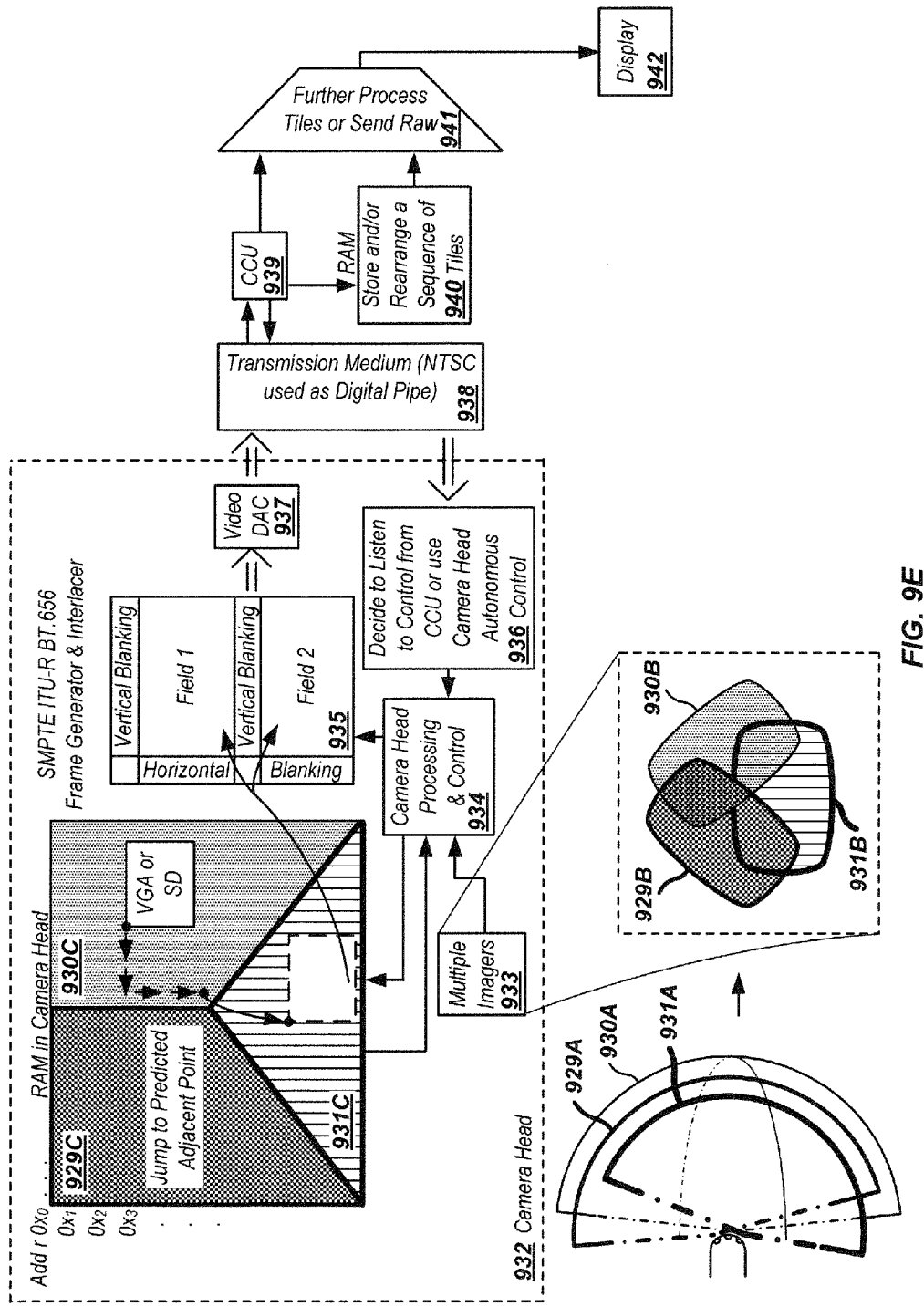
FIG. 9E is a block diagram illustrating details of an embodiment of digital articulation of a multiple image sensor data combined to generate a single image or string of images of greater field of view or detail than can be provided by a single imager.

FIG. 9E illustrated details of another aspect, wherein multiple imagers 929A, 930A, and 931A are disposed in an imaging sensor array in a camera head 932. Each of the image sensors may have a fairly wide angle field of view, but less than 180 degrees. When combined, the image sensor array may have a field of view that is greater than 180 degrees. In operation, a processing element 934 in camera head 932 may intelligently combine data sets 929B through 931B (generated from corresponding image sensors 929A-931A) to corresponding mapped memory 929C-931C. The memory map contents may then be selectively extracted, such as by scanning with a pointer that specifies which windowed viewport or tile (e.g., as VGA, SD, HD, non-standard, etc.) as a video frame for output at a given time. The window may be scanned around the image data, and a camera head processing element 934 or CCU processing element 936 may select when to switch from image data from one image sensor to the next based on what location provides the smoothest transition. This may be based on a known or determined overlap area of view of the imaging sensors of the sensor array. In an exemplary embodiment, there may be some or even substantial overlap between sensor imaging area. Alternately, in some embodiments the sensors may be oriented to provide approximately unique coverage areas that may form adjacent boundaries. A predefined distortion correction map of the lens/optics coupled to each image sensor of the sensor array may be stored in memory and used to correct distortion of the images generated by the sensors (e.g., to correct fisheye, pincushion, chromatic distortion, or other wide-angle lens distortions or other optical distortions) to provide better cross-sensor transitions, stitched combinations, or other image processing.

Processing methods in the camera head 934 or CCU 936 may decide which imager's data to send for viewing that particular area in order to provide a desired transition, such as based on known or determined overlay areas, or other inputs, such as orientation, location, or positioning sensor data. Viewing of tiles at viewing angles with no overlap may not require a decision since only one imager may provide information from that viewing area.

The selected image region may then be inserted into a standardized frame generator 935 that can provide a video DAC 937 with digital video for analog conversion and transmission 938. The CCU 939 can then display 942 the tile as video, or send it to memory 940 for construction into a higher resolution image/video 900B for display.

Figure 9F:
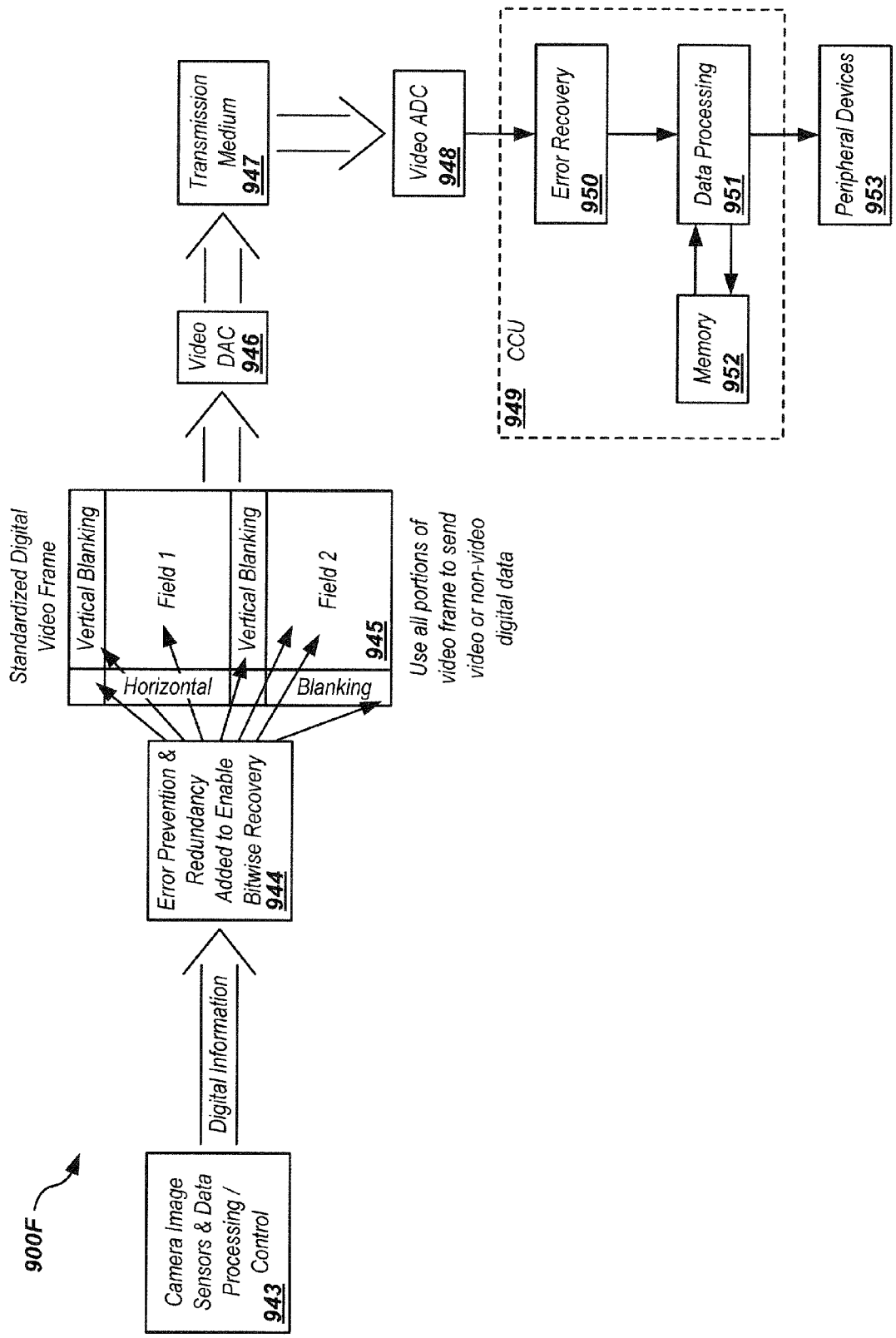
FIG. 9F is a block diagram illustrating details of an embodiment of standardized analog video being used as a general purpose digital transmission scheme.

In another aspect, standardized analog video may be used to transmit data. For example, FIG. 9F is a block diagram illustrating details of one embodiment of standardized analog video being used as a general purpose digital transmission mechanism. Information collected by sensors in the camera head 943, and/or other data or information, may be sent to a processing module that adds redundancy and error detection/correction data, such as in error encoding module 944. The digital data may then be inserted into the active and non-active video portions of a standardized video frame generator in module 945. The video frames containing the general purpose digital data may be converted to an analog video signal by a video DAC 946, and sent over a transmission media 947 to a video ADC 948. The resulting digital video may received at a CCU 949 and error detected and corrected by utilizing the overhead/redundancy information inserted in the camera head, in error recovery module 950, data processing module 951, and memory 952. The resultant data may then be stored in the CCU and/or provided to peripheral devices 953. Using this configuration, a standardized ITU-R BT.656 and/or NTSC/PAL analog video signal may be used as a general purpose digital information pipe, such as in inspection systems between a camera head and CCU.

Figure 9G:
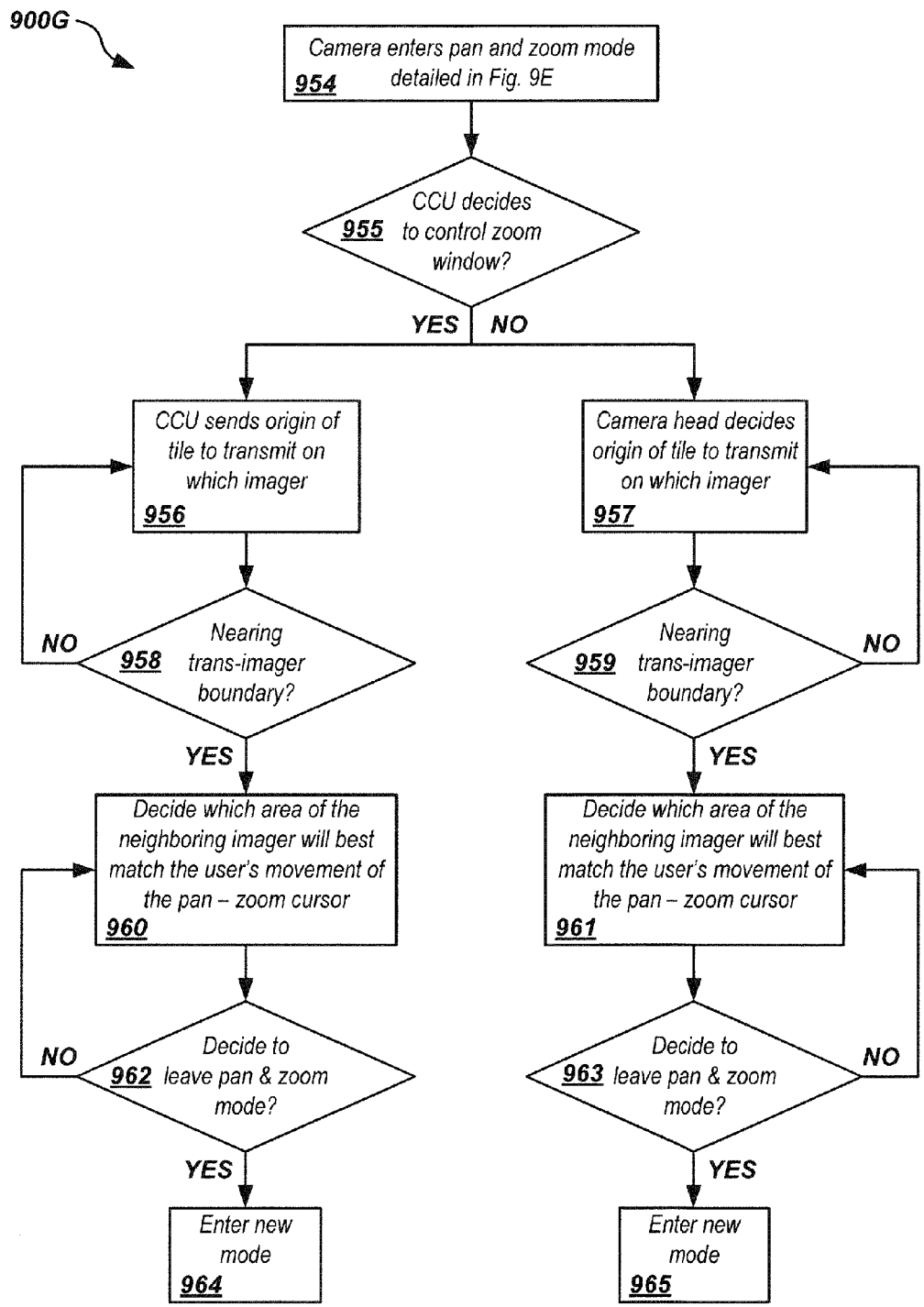
FIG. 9G illustrates details of an embodiment of a process for providing output image data across image sensor boundaries in an image sensor array.

FIG. 9G illustrates details of an embodiment of a process 900G for controlling panning or zooming in an image sensor array including a plurality of imaging elements (each of which includes an image sensor and associated optics). At stage 954, the camera head may enter a pan/zoom mode, such as shown in FIG. 9E. This may be initiated automatically, such as based on an operating condition of a corresponding inspection system, and/or based on a user control input. If a user input is provided, the CCU may send a control signal to the camera head (e.g., camera head 932) to digitally articulate the output viewport and corresponding displayed area of the area being inspected. At decision stage 955, a decision may be made as to whether to control the imaged window or viewport from the CCU (YES) or from the camera head itself (NO), such as based on sensor or other information, such as orientation, position, location, and/or other sensor data.

Assuming the camera head is controlled by the CCU, at stage 956, a reference position, such as the origin coordinates or other position information of the starting tile may be sent. This may include an overall coordinate reference and/or a specific image sensor references (of the plurality of image sensors in the image sensor array). Image sensor data may then be sent for one or more frames. At stage 958, a determination may be made as to whether the tile/viewport is approaching a boundary. This may be determined by reference optical marks, sensor data, image array reference data (e.g., sensor movement and direction and location within an overlap zone or boundary area) and/or other data or information. If no image boundary is sensed, processing may return to stage 956 and either the previous tile/viewport reference used to generate a subsequent image or a new controlled reference position may be received from the CCU to allow transition to that new reference position. In some embodiments, transitions may be effected in a slow, continuous matter, such as by moving sequentially through intermediate pixels between the initial and final viewport positions. Alternately, in some embodiments, the output viewport may be switched rapidly to a newly received viewport position (from the CCU).

At stage 960, a determination may be made as to what area of an adjacent image sensor should be transitioned to (i.e., what area of the adjacent image sensor best aligns with the current or most recent viewport area). The output viewport may then be transferred from pixels of the first image sensor to the closest matching pixels of the adjacent image sensor. This may be done as a hard switch between image sensors and/or may be done as a merge or combined pixel transition, where pixels of both image sensors are used to generate image and video data during a transition period. At stage 962, a decision may be made as to whether to continue in pan/zoom mode or enter a new mode. If pan/zoom mode is to be continued, processing may return to stage 960 and/or to stage 956 to continue sending image data.

If camera head control is determined at stage 955 (i.e., NO state), processing may continue to stage 957, where the camera head may decide the origin or reference of the tile to be transmitted. This may include an overall coordinate reference and/or a specific image sensor references (of the plurality of image sensors in the image sensor array). Image sensor data may then be sent for one or more frames. At stage 959, a determination may be made as to whether the tile/viewport is approaching a boundary. This may be determined by reference optical marks, sensor data, image array reference data (e.g., sensor movement and direction and location within an overlap zone or boundary area) and/or other data or information. If no image boundary is sensed, processing may return to stage 957 and either the previous tile/viewport reference used to generate a subsequent image or a new controlled reference position may be received from the CCU to allow transition to that new reference position. In some embodiments, transitions may be effected in a slow, continuous matter, such as by moving sequentially through intermediate pixels between the initial and final viewport positions. Alternately, in some embodiments, the output viewport may be switched rapidly to a newly received viewport position (from the CCU).

At stage 961, a determination may be made as to what area of an adjacent image sensor should be transitioned to (i.e., what area of the adjacent image sensor best aligns with the current or most recent viewport area). The output viewport may then be transferred from pixels of the first image sensor to the closest matching pixels of the adjacent image sensor. This may be done as a hard switch between image sensors and/or may be done as a merge or combined pixel transition, where pixels of both image sensors are used to generate image and video data during a transition period. At stage 963, a decision may be made as to whether to continue in pan/zoom mode or enter a new mode. If pan/zoom mode is to be continued, processing may return to stage 961 and/or to stage 957 to continue sending image data.

Figure 10:
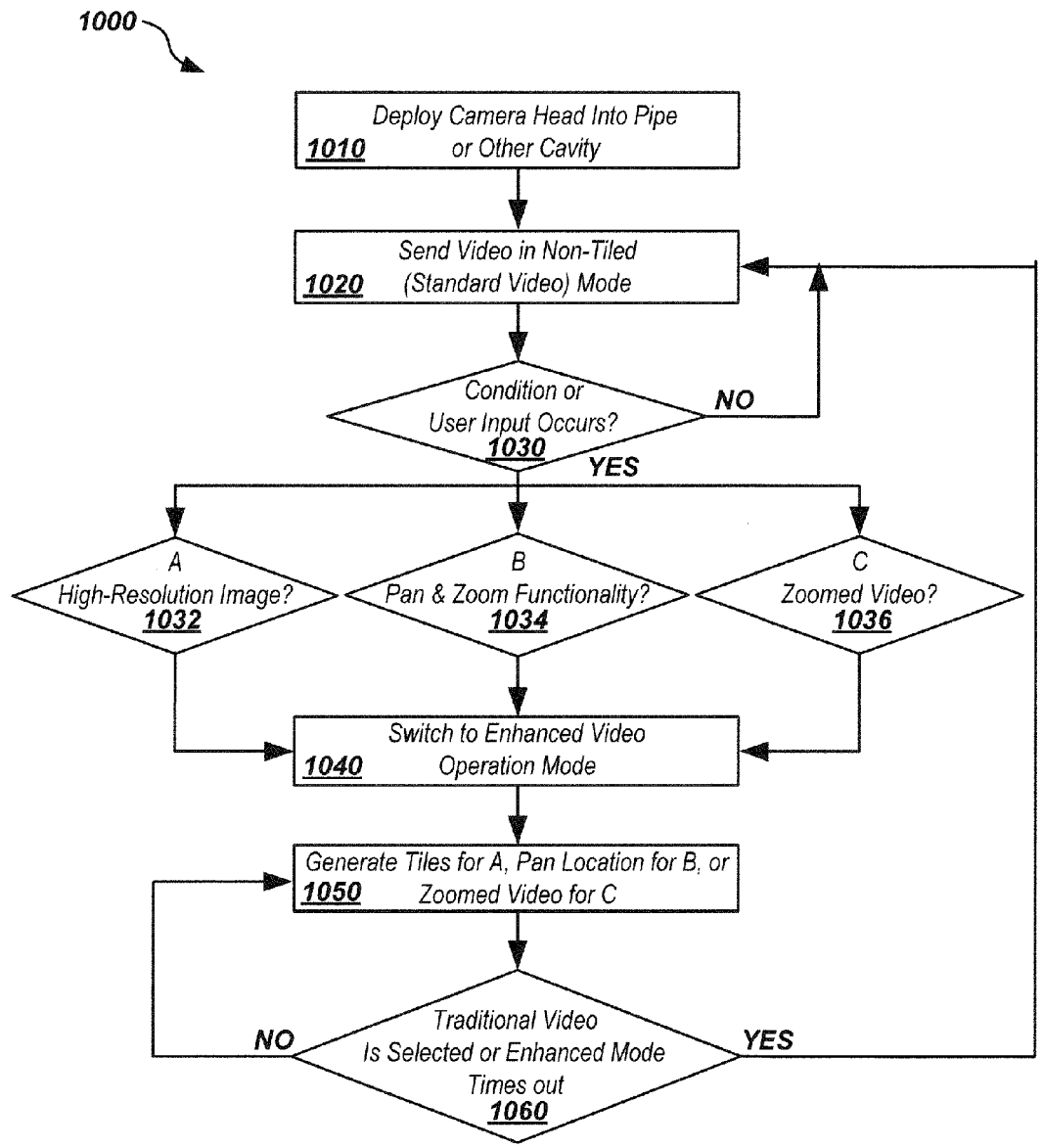
FIG. 10 illustrates details of an embodiment of tiled video processing.

Turning to FIG. 10, a generalized process embodiment 1000 for processing tiled images in a camera head of a pipe inspection system is illustrated. Process 1000 may begin at stage 1010 where the camera head and associated inspection system components, such as a push-cable, etc., are deployed into a pipe or other cavity being inspected. This may be done by a powered cable reel system and/or by an operator manually feeding the camera system into the pipe or other cavity.

At stage 1020, during a non-tiled or standard operating mode, data from the camera head image sensor may be generated and converted to an analog video signal in a standard mode, such as, for example, NTSC or PAL mode, and sent to a display system device such as a camera control unit via a wired or wireless connection. Although analog video is typically used in existing systems and is likely to remain in use for some time, in some embodiments the video signal may be in a standard mode, such as, for example, NTSC or PAL mode, and sent to a display system device such as a camera control unit via a wired or wireless connection. Although analog video is typically used in existing systems and is likely to remain in use for some time, in some embodiments the video output signal from the camera head may be a digital video signal or other digital data signaling.

At stage 1030, a sensing element, such as an accelerometer or other motion, position, optical, audio, or other sensor output, may generate a condition signal associated with the camera head and/or a condition or state within the pipe or other cavity. In an exemplary embodiment, the condition is stoppage of movement of the camera head within the pipe, such as when an operator stops pushing or otherwise deploying the camera head into the pipe. In other cases, the condition may be a speed state, such as a speed of movement of the camera head within the pipe dropping below a predefined threshold. In other cases, the condition may be a user input provided from the CCU or other display system, such as an operator input provided to the camera head to change from standard operating mode to an enhanced video mode (referring to 1032, 1034 or 1036), such as the tiled, pan and zoom, or zoomed video modes described subsequently herein. The condition may also be sensed by, for example, sensing a vibrational output of an accelerometer or other inertial navigation sensor disposed in the camera head. In operation, when a camera head is deployed at the end of a push cable, vibrations sensed by the accelerometer during deployment of the cable typically decrease or stop, thereby providing an indication of motion stoppage. Motion sensors and associated processing elements may be configured and calibrated based on particular motions or related signals, such as vibration signals, audio signals, etc. Predefined thresholds for these sensor signals may be used to determine motions. Gyroscopic or compass sensors can similarly be used. Other sensing mechanisms may include distance measurement elements, such as a cable counter in a cable reel on which the push cable may be stored, or other motion or position measurement sensors or devices.

Assuming the condition occurs or an operator input is provided, at stage 1040 the camera head and/or CCU may switch to an enhanced video mode. In the camera head, tiled image and/or zoomed video and/or pan and zoom video may be generated, such as described subsequently herein, and then converted to an analog signal and provided to the CCU or other display system device. Images and/or enhanced video may be sent in this way at stage 1050 until the condition changes (e.g., the camera head starts moving again or other conditions change) or a subsequent operator input is provided at stage 1060. If no change occurs at stage 1060, enhanced video mode (labeled A, B, and C) operation may continue, such as, for example, providing ongoing tiled mode analog video output from the camera head. Alternately, if the condition changes at stage 1060, operation may return to standard mode operation at stage 1020.

In an exemplary embodiment, frame stacking and high dynamic range techniques and methods may be used when the camera head from stage 1010 is stopped. For example, the exposure may be varied frame to frame.

Figure 11:
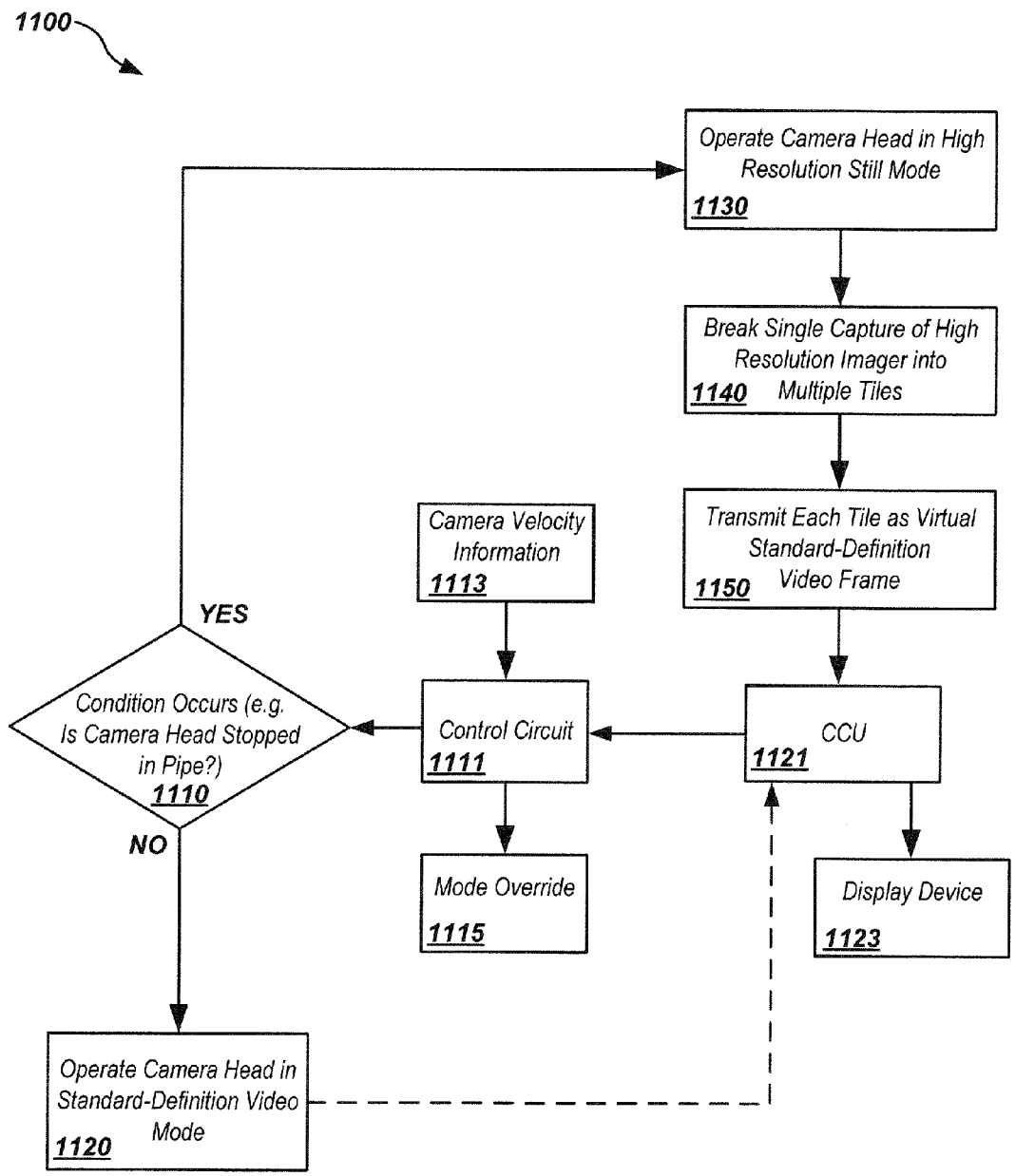
FIG. 11 illustrates details of an embodiment of a high-resolution still mode of tiled video processing.

FIG. 11 illustrates additional details of one embodiment 1100 of tiled mode operation for providing high resolution still mode images. Process 1100 may begin at stage 1110, where a condition is checked for. Stage 1110 may correspond with stage 1030 of FIG. 10. If the condition has occurred, such as, for example, the camera head has stopped moving as may be determined at a control circuit 1111 based on velocity information 1113, which may be provided from an accelerometer or other motion or position sensing device, high resolution still operating mode may be entered at the camera head and/or CCU. A mode override input 1115, such as may be provided from an operator, may also be used to override automatic sensing and allow direct operator control of the control circuit 1111.

During operation in the high resolution still mode, the image sensor may generate pixel data at stage 1130 which may then be processed at stage 1140, such as in a processing element as described herein, to divide the sensed pixels into multiple tiles, such as the four tiles shown in FIG. 9A or into fewer or typically more tiles. At stage 1150, each tile may be converted to an analog (or, in some implementations, digital) standard definition video frame or sub-frame. The analog video signal may then be sent to the camera control unit (CCU) 1121, where it may then be stored, sent to other devices or system, and/or displayed on a display device 1123. In an exemplary embodiment, multiple tiles may be extracted from the analog video signal and recombined in the CCU to generate a high-resolution image that may then be presented to a user on the display device 1123.

Figure 12:
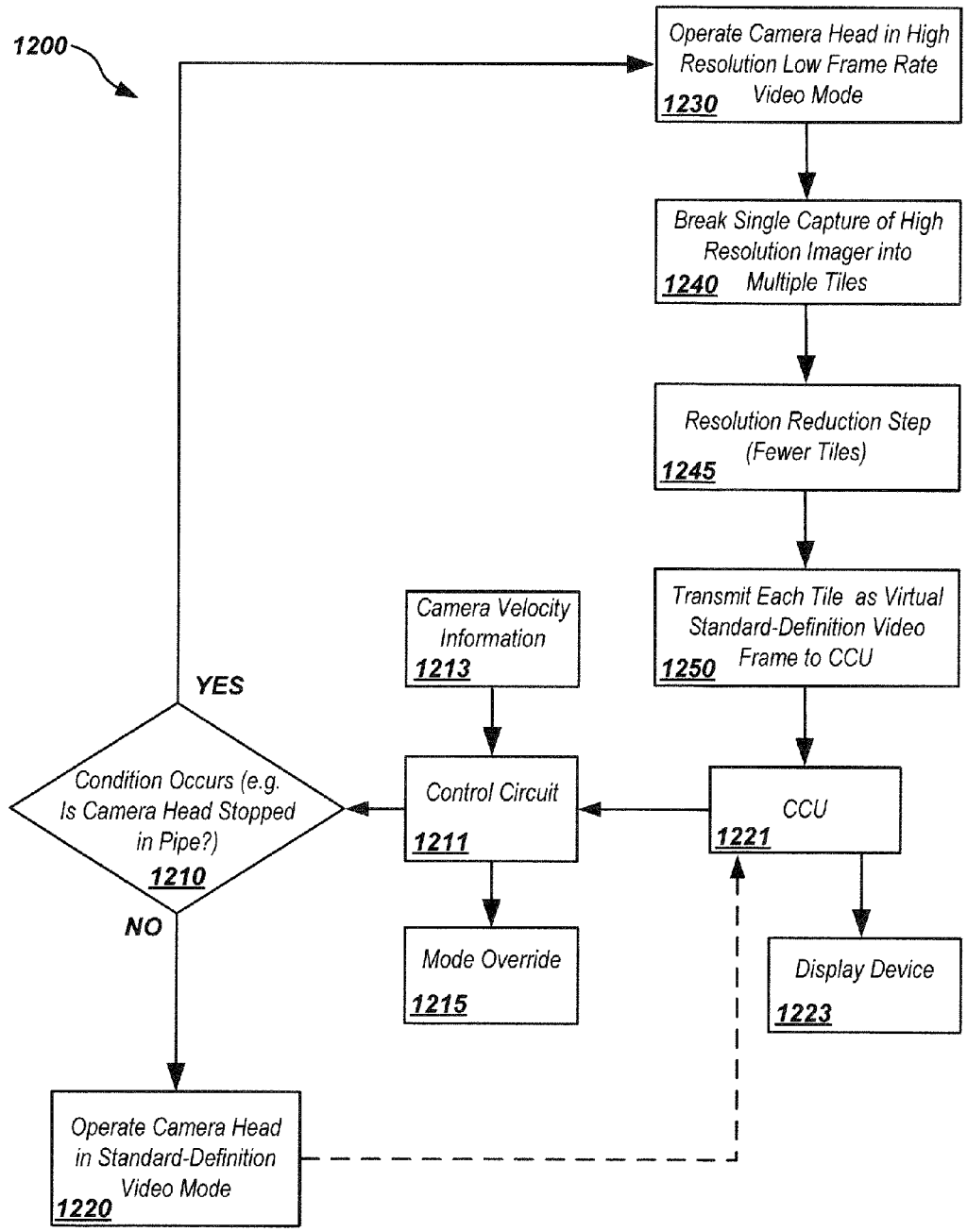
FIG. 12 illustrates details of an embodiment of an intermediate-resolution still mode of tiled video processing.

FIG. 12 illustrates additional details of another embodiment 1200 of tiled mode operation for providing intermediate resolution still mode images. Components of inspection systems as illustrated in FIG. 12 may correspond with analogous components as described in FIG. 11, such as, for example, control circuit 1111 corresponding with control circuit 1211, CCU 1121 corresponding with CCU 1221, display 1123 corresponding with display 1223, etc.

Process 1200 may begin at stage 1210, where a condition is checked for. Stage 1210 may correspond with stage 1030 of FIG. 10. If the condition has occurred, such as, for example, the camera head has stopped moving as may be determined at a control circuit 1211 based on velocity information 1213, which may be provided from an accelerometer or other motion or position sensing device, intermediate resolution still operating mode may be entered at the camera head and/or CCU. A mode override input 1215, such as may be provided from an operator, may also be used to override automatic sensing and allow direct operator control of the control circuit 1211.

During operation in the intermediate resolution still mode, the image sensor may generate pixel data at stage 1230 which may then be broken into multiple tiles at stage 1240, The tiles may be then be reduced in resolution at stage 1245, by, for example, reducing the resolution of the tiles, reducing the number of tiles, etc. Stages 1240 and 1245 may be implemented in a processing element as described herein. At stage 1250, each tile may be converted to an analog (or, in some implementations, digital) standard definition video frame or sub-frame. The analog video signal may then be sent to the camera control unit (CCU) 1221, where it may then be stored, sent to other devices or system, and/or displayed on a display device 1223. In an exemplary embodiment, multiple tiles may be extracted from the analog video signal and recombined in the CCU to generate an intermediate resolution image that may then be presented to a user on the display device 1223.

Figure 13:
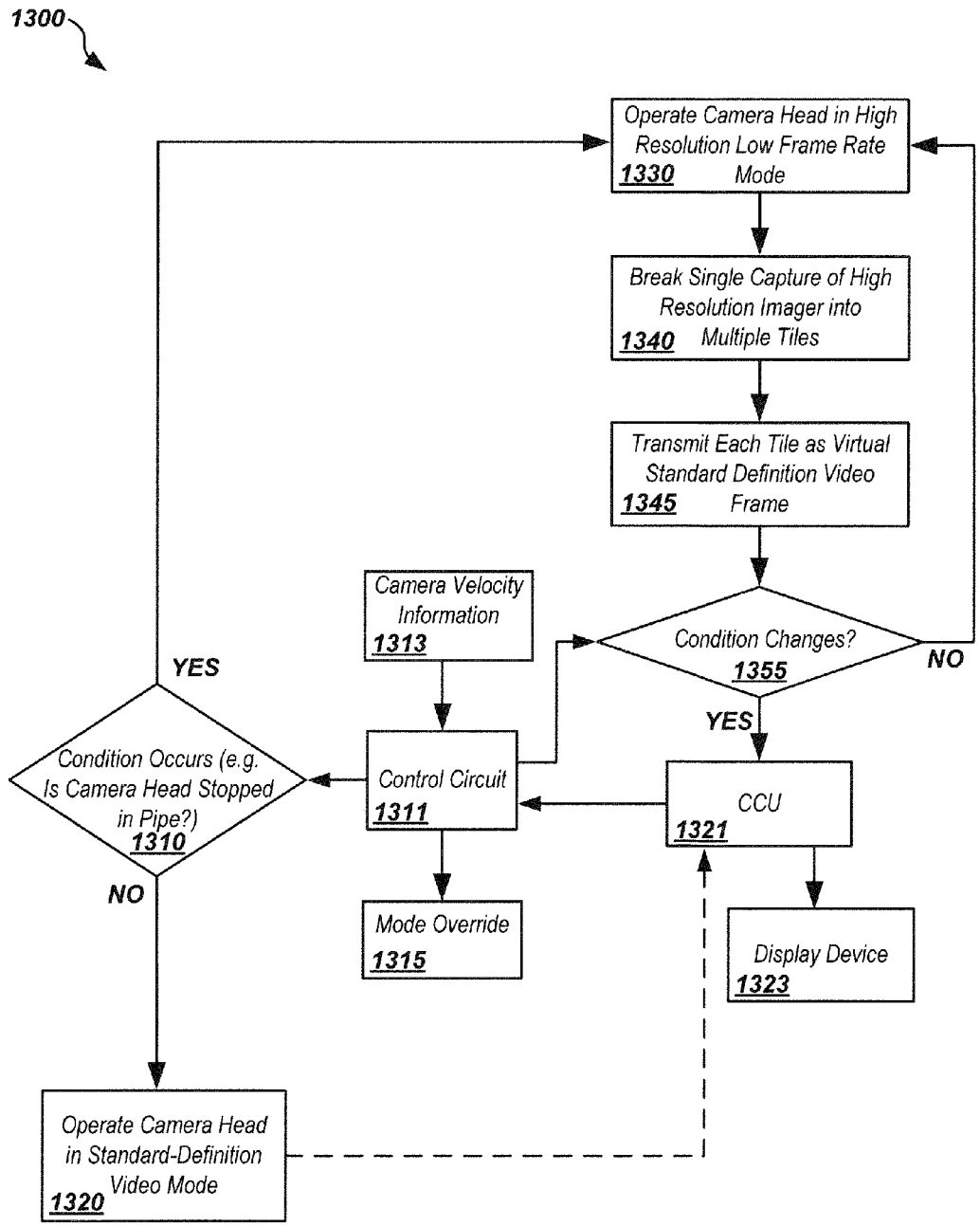
FIG. 13 illustrates details of an embodiment of a high resolution low frame rate video mode of tiled video processing.

FIG. 13 illustrates additional details of another embodiment 1300 of tiled mode operation for providing higher resolution video. In a bandwidth constrained system operating at or near the bandwidth capacity, the frame rate may be reduced corresponding to the increase in video resolution. Components of inspection systems as illustrated in FIG. 13 may correspond with analogous components as described in FIG. 11, such as, for example, control circuit 1111 corresponding with control circuit 1311, CCU 1121 corresponding with CCU 1321, display 1123 corresponding with display 1323, etc.

Process 1300 may begin at stage 1310, where a condition is checked for, which may be similar to that described with respect to FIGS. 11 and 12. Stage 1310 may correspond with stage 1030 of FIG. 10. If the condition has occurred, such as, for example, the camera head has stopped moving as may be determined at a control circuit 1311 based on velocity information 1313, which may be provided from an accelerometer or other motion or position sensing device, intermediate resolution still operating mode may be entered at the camera head and/or CCU. A mode override input 1315, such as may be provided from an operator, may also be used to override automatic sensing and allow direct operator control of the control circuit 1311.

During operation in the high resolution video mode, the image sensor may generate pixel data at stage 1330 which may then be broken into multiple tiles at stage 1340, thereby resulting in a sequence of tiles, which may each be sent as a frame of a standard analog video signal (or, in some embodiments, a digital signal). Stages 1340 and 1345 may be implemented in a processing element as described herein. Once all the tiles from a single frame have been transmitted, such as for example, at stage 1345, then the camera may acquire another frame and repeat 1330, 1340, and 1345, or may alternately change modes, resolution, tile sizes, and/or number of tiles, etc. at a stage 1355.

For example, in the sensor configuration as shown in FIG. 9A, four tiles would be sent for each subsequent frame of high resolution video. In the CCU 1321, the tiled information may then be stored, sent to other devices or system, and/or displayed on a display device 1323. In an exemplary embodiment, multiple tiles may be extracted from the analog video signal and recombined (e.g., at four tiles/video frame) in the CCU to generate a high resolution video signal that may then be presented to a user on the display device 1323. As noted previously, the video output resolution will typically be inversely related to the frame rate due to the transmission of multiple tiles per output video frame.

Figure 14:
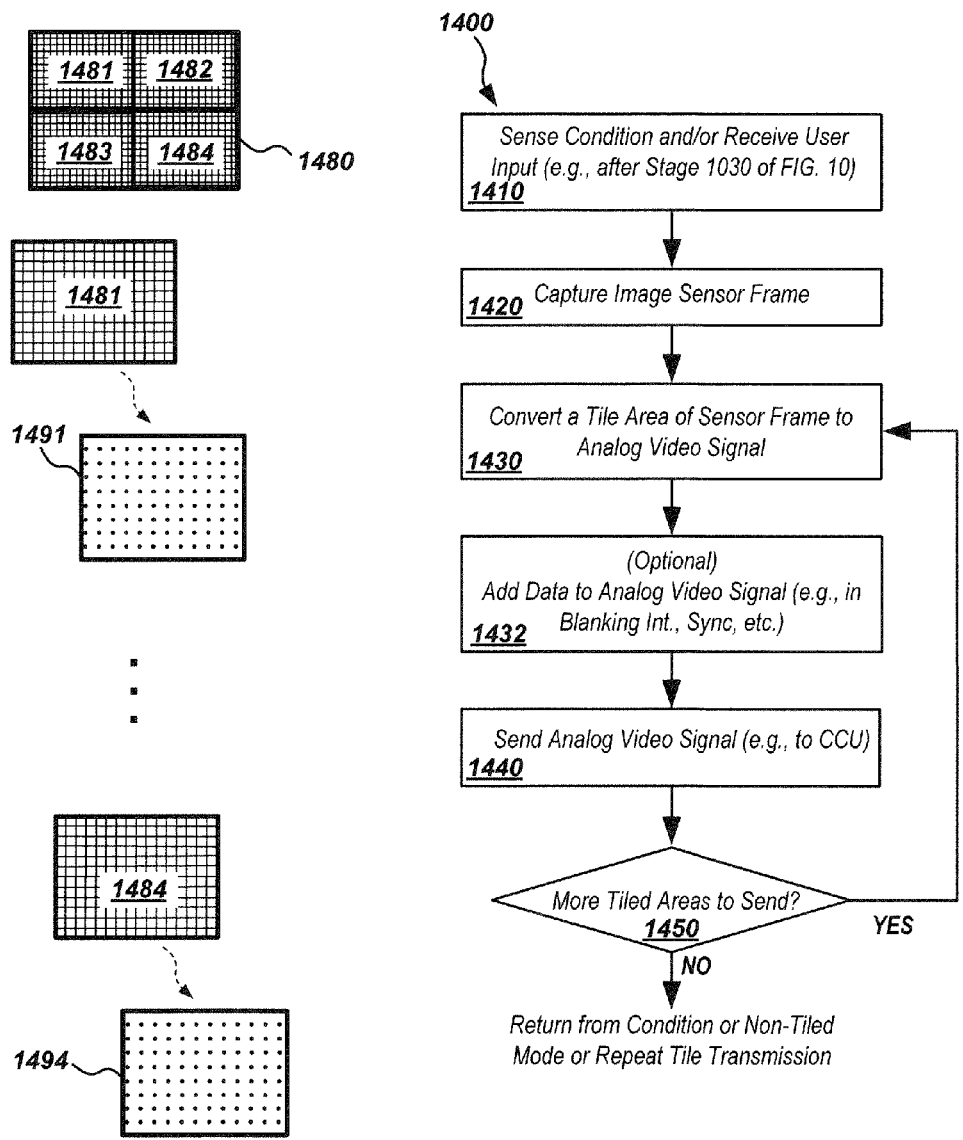
FIG. 14 illustrates details of an embodiment of tile generation and processing to provide high resolution video or images.

FIG. 14 illustrates additional details of an embodiment 1400 of tiled image sensor data processing as may be done in a camera head of an inspection system. Image frame 1480 may correspond with a sensed or captured image of a sensor element, such as sensor 600 of FIG. 6. As shown, the image may be subdivided into a plurality of tiles that each covers a subset of the image field of view. In some cases the aggregate image field of view may be less than that of the sensor, however, the field of view will typically be selected to cover substantially all the field of view of the sensor and associated optics so as to provide the widest angle of coverage available.

In the example of FIG. 14, four tiles, 1481, 1482, 1483, and 1484 are shown, however, as noted previously other numbers and/or positions of tiles may be used in other embodiments.

Process 1400 may be begin at stage 1410 in response to the sensing of a condition or user input, such as the motion-related conditions described previously herein. This may be, for example, after stage 1030 of FIG. 10. At stage 1420, a full image frame may be captured or, in some cases, a smaller field of view that may then be further tiled. At stage 1430, a first tile of the plurality of tiles may be converted to an analog video frame or sub-frame. For example, as shown in FIG. 14, tile 1481 may be converted to a corresponding analog frame 1491, which may be sent as an analog video signal from the camera head to a CCU. At optional stage 1432, data may be added to the video signal, such as in the blanking or sync intervals, or at other places in the video signal.

In some embodiments, additional data or information may be added to the analog video signal and/or may be sent as a separate analog or digital signal to the CCU. For example, data may be added to blanking intervals of the video, sync intervals, or during other available data transmission intervals of the analog signal. The data may be, for example, information representing the position, size, shape, of the tile or other information related to the tile. Other information, such as additional sensor data, timing information, re-assembly information, or other information may also be included in the data.

At stage 1440 the analog video signal including the first tile may be sent. At stage 1450, a test may be made regarding whether all of the tiles have been sent. If not, additional tiles (e.g., tiles 1482, 1483, and 1484) may also be converted and sent to the CCU in a similar fashion. If all the tiles have been sent, processing may then return to the pre-condition state or the transmission of the next frame of high resolution video may be started.

Figure 15:
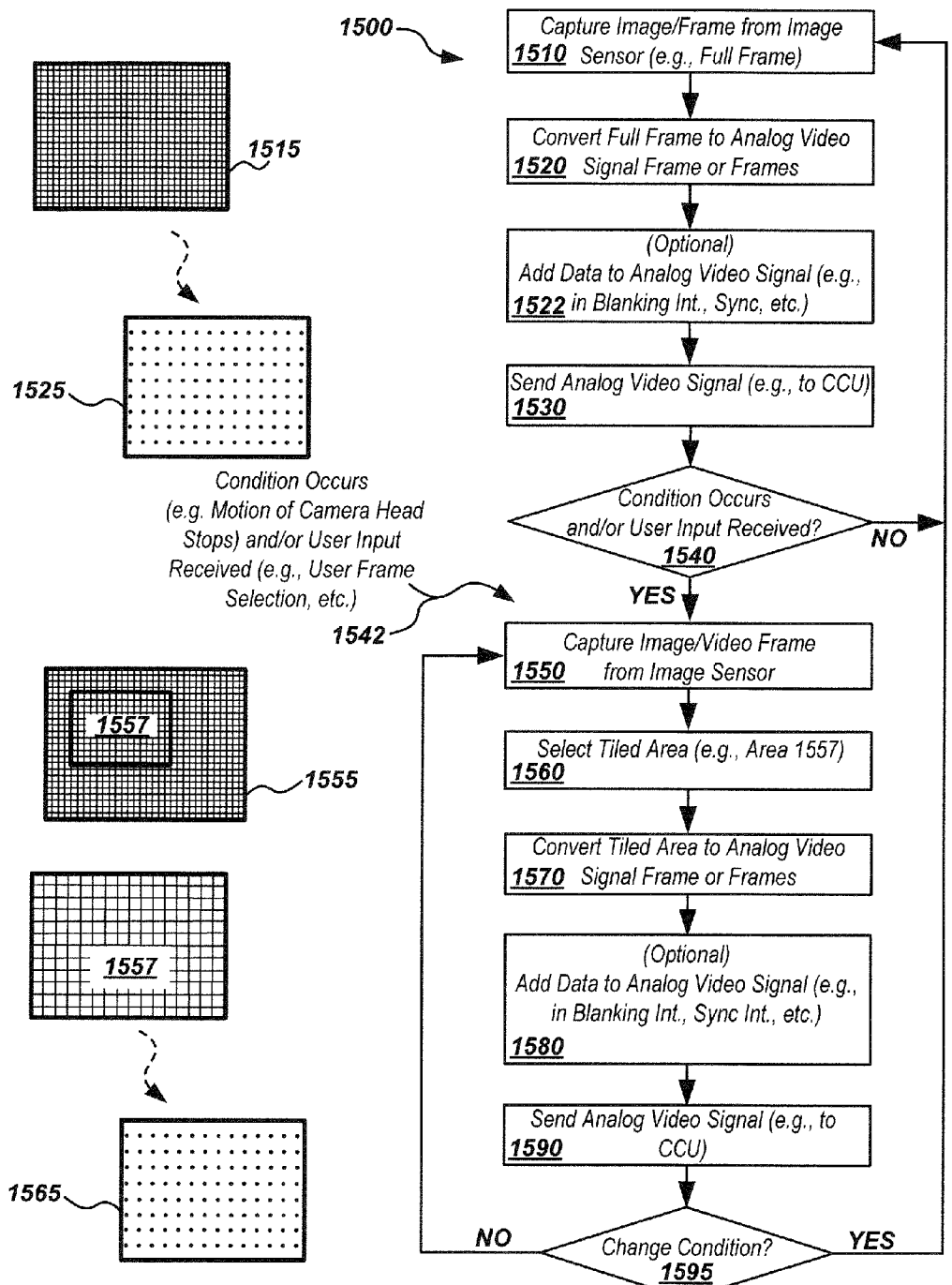
FIG. 15 illustrates details of an embodiment of tile generation and processing to provide a selected tile or tiles.

FIG. 15 illustrates additional details of an embodiment 1500 of selective tile data processing as may be done in a camera head of an inspection system. Process 1500 may be used in combination with process 1400 as illustrated in FIG. 14 to provide both multiple tiled and position-specific tiled image processing. Image frame 1515 may correspond with a sensed or captured image of a sensor element, such as sensor 600 of FIG. 6. An initial output analog video frame or frames 1525 may be generated from data received from the image sensor, with subsequent position-specific tiled areas, such as areas 1557 of image frame 1555 as shown, converted to an analog video signal or signals.

Process 1500 may begin at stage 1510 with capture of an image frame from an electronic image sensor in a camera head, such as sensor 600 of FIG. 6. At stage 1520, a full frame image (or, in some implementations, a subset of the full frame image) may be converted to an analog video signal frame or frames, such as scanned analog video frame 1525 as shown. Optionally, at stage 1522, data may be added to an analog video signal (e.g., in blanking interval, sync, etc.) At stage 1530, the analog frame or frames may then be sent from the camera head to a CCU or other system display device.

At stage 1540, in response to the sensing of a condition or user input, such as the motion-related conditions described previously herein or based on a user input, such as a user selection of a zoomed-in area and/or position of the image frame, a tiled area, such as area 1557, may be processed. For example, at stage 1550, a full frame of image data may be sensed and, at stage 1560, a tiled sub-area, such as area 1557, may be further processed at stage 1570 to generate an analog signal (or, in some implementations as described elsewhere herein, a digital data signal). Additional data or information may optionally be added at stage 1580, such as described previously with respect to stage 1432 of process 1400. At stage 1590, the analog video signal corresponding to the selected tile may then be sent to the CCU or other system display device. In some embodiments, the tiled image generation may be repeated, such as for a predetermined time interval or based on a condition or further user input. For example, at stage 1595, the steps may repeat starting from the beginning at stage 1510, or alternatively, repeat from stage 1550.

Figure 16:
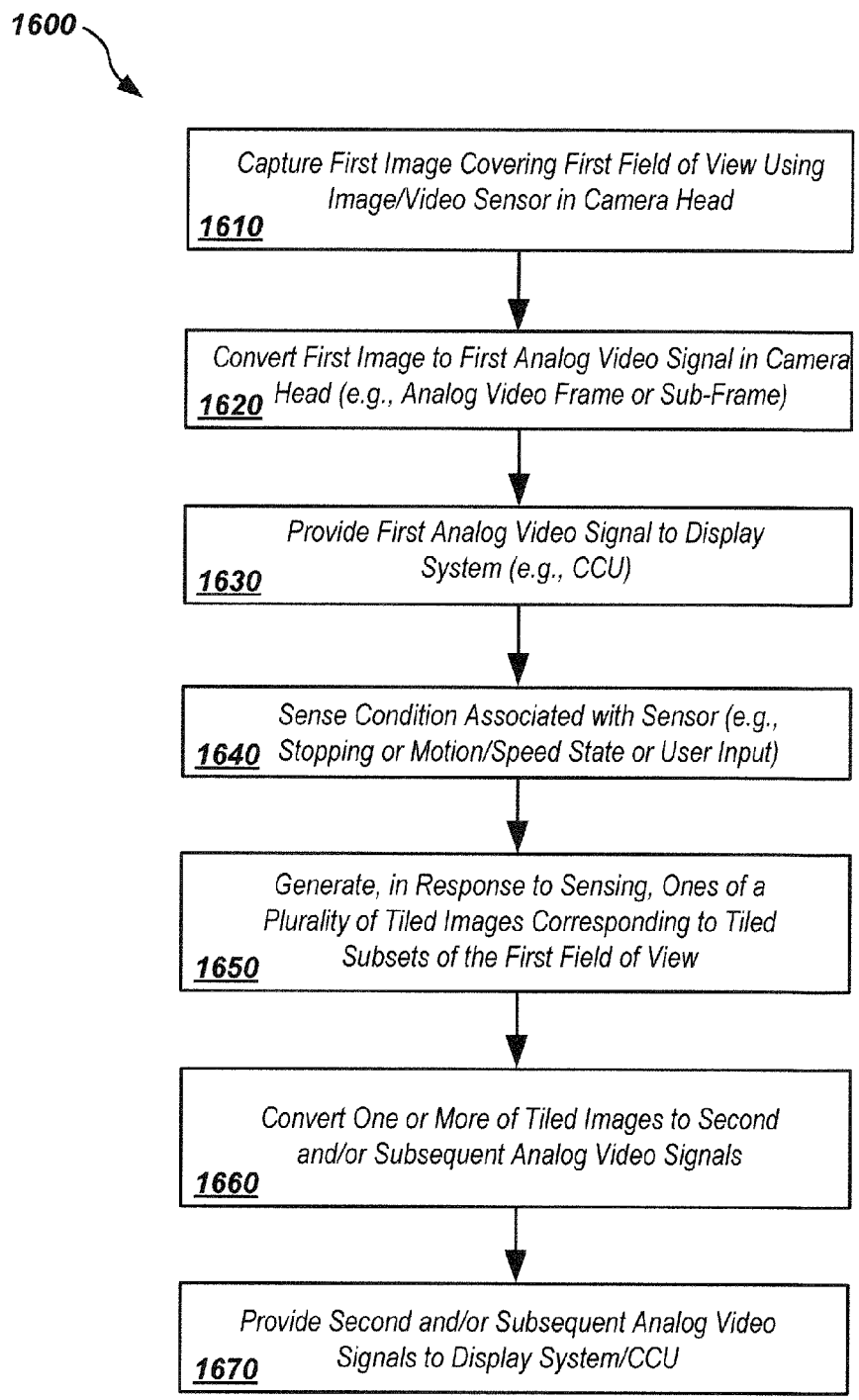
FIG. 16 illustrates details of an embodiment of a process for providing a variable resolution display in an inspection system.

FIG. 16 illustrates details of an embodiment of a process 1600 for providing a variable-resolution visual display in an inspection system, such as a pipe inspection system. Process 1600 may begin at stage 1610 where a first image may be captured in an electronic image sensor of a camera head, with the first image covering a first field of view. At stage 1620, the first image may be converted to a first analog signal, and providing to a camera control unit (CCU) at stage 1630. Process 1600 may further include sensing a condition associated with the image sensor at stage 1640, such as a motion condition or a user provided input. At stage 1650, responsive to the sensing or user input, ones of a plurality of tiled images corresponding to tiled subsets of the first field of view may be generated, such as in a processing element of the camera head. At stage 1660, the plurality of tiled images may be converted to a second analog signal. The second analog video signal may be provided to the CCU or other display device at stage 1670.

The imaging sensor may be a high resolution sensor and the first image may be captured at a high resolution. In some embodiments the first image and/or plurality of tiled images may be provided as a digital signal rather than an analog video signal.

The process 1600 may further include, for example, receiving the first analog signal at a system display device, such as a camera control unit (CCU), and providing a first visual output corresponding to the first analog signal on a display device at a first resolution. The method may further include receiving the second analog signal and combining, such as in a processing element of the CCU or other system display device, the plurality of tiled images of the second analog signal to provide a second visual output on the display device. The second visual output may be provided at a second resolution that is higher than the first resolution.

The process 1600 may further include, for example, generating a second plurality of tiled images corresponding to tiled subsets of the first field of view, converting the second plurality of tiled images to a third analog signal, providing the third analog signal to the CCU, and combining the second plurality of tiled images of the third analog signal to provide a third visual output on the display device at a third resolution different than the first and the second resolutions.

The second and/or third visual outputs may, for example, be provided as a zoomed-in field of view relative to the first visual output. The first image and/or second image may be provided as frames of a video signal. The first image and the aggregate of the tiled subsets may correspond to the same field of view. The aggregate of the tiled subsets may correspond to a narrower field of view than the first image. Alternately, the aggregate of the tiled subsets corresponds to a wider field of view than the first image. The first image and the aggregate of the tiled subsets may approximately correspond to the field covered by the full frame of the image sensor. A subset of tiles may be used to create zoomed and/or panned out images. The camera head may be configured to send a sub-set of the tile grid if the CCU does not require all tiles to generate the zoomed in display.

The CCU may be configured to communicate information to the camera head to coordinate configuration and information transfer, in either one or both directions. For example, the CCU may send a configuration signal to the camera head to send only the tiles needed at the CCU or switching operating modes, while other operating modes only require the camera head to communicate with the CCU.

The plurality of tiled images may include, for example, four tiled images. Each of the four tiled images may correspond to approximately one quarter of the first field of view. Alternately, the plurality of tiled images includes may include nine tiled images and each of the nine tiled images corresponds to approximately one ninth of the first field of view. In other embodiments, different numbers of tiles, such as 2 tiles, 6 tiles, 12 tiles, or other numbers of tiles may be used.

The condition at stage 1640 may, for example, correspond to a motion of the image sensor. The motion may be a stop motion, such as the stoppage of movement of the camera head within the pipe or other cavity. Alternately, or in addition, the motion condition may be a speed threshold, such as a predefined maximum or minimum speed of the camera head within the pipe or other cavity. Alternately, or in addition, the motion may be a start motion, such as a start of movement of the camera head within the pipe or other cavity. The motion may be determined based on signals such as vibration signals, audio signals, image signals, or other signals related to motion or position. Motion or vibrational signals may be sensed by devices such as accelerometers, compass sensors, counters, image sensors, or other sensing elements in the camera head, push cable, or associated components such as cable reels. Alternately, or in addition, the condition may be a rotation of the image sensor relative to a reference orientation. The reference orientation may be, for example, an up-down gravitational orientation. The motion may be determined based on signals such as vibration signals, audio signals, image signals, or other signals related to motion or position. For example, motion may be ascertained from image data/signals.

The process 1600 may further include, for example, providing data associated with the plurality of tiled images. The data may relate to a position and/or size of the ones of the plurality of tiled images. Alternately, or in addition, the data may relate to a transmission mode in use in the pipe inspection system, such as a high resolution or medium resolution still mode or a high resolution reduced frame rate video mode. Alternately, or in addition, the data may relate to one or more sensing conditions associated with the images being transmitted, such as information generated by motion sensors, position sensors, pressure or temperature sensors, audio or optical sensors, image sensors, other sensors. The data may be sent in every video frame or may be sent in only certain frames. The data may be sent in another communication channel from the video signals, such as a second wired or wireless transmission medium.

The first image and/or the ones of a plurality of tiled images and/or the corresponding higher resolution images or video may be stored on a digital storage medium, such as a flash memory or drive, a disc, removable storage media, Blu-Ray, DVD media, and the like. Alternately, or in addition, the first image and/or the ones of a plurality of tiled images may be provided as a hard copy output.

The subset of the plurality of tiled images may, for example, be used to generate the zoomed-in field of view of the second visual output. The data may relate to electronic image sensor status information and/or camera head information at the time of image capture.

In an exemplary embodiment, images may be stored in the camera head for later retrieval.

Figure 17:
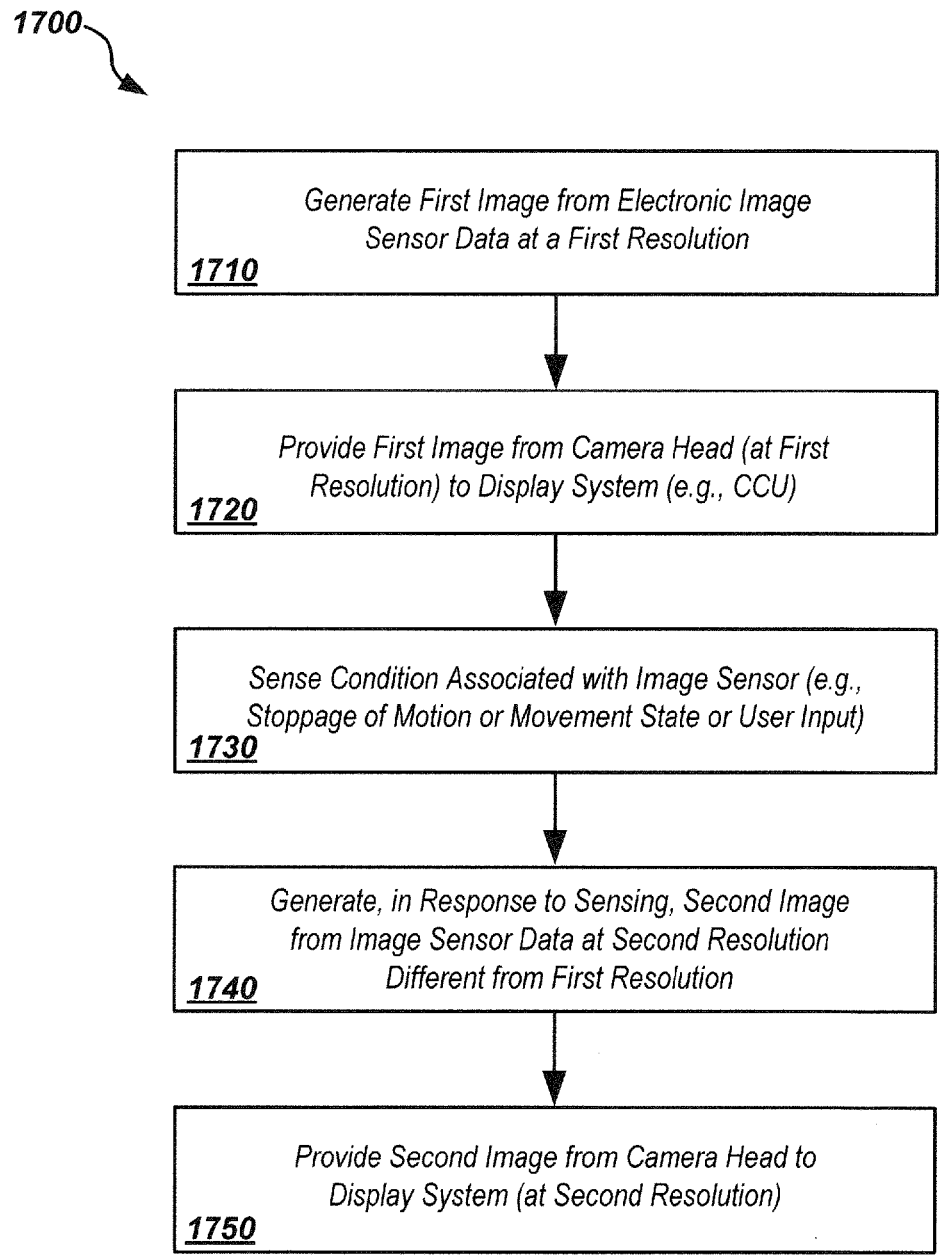
FIG. 17 illustrates details of an embodiment of a process for providing a selectable tiled display in an inspection system.

FIG. 17 illustrates details of an embodiment of a process 1700 for providing a visual display in an inspection system, such as a pipe inspection system. Process 1700 may begin at stage 1710 where a first image from an electronic image sensor at a first resolution may be provided to a camera control unit (CCU). At stage 1720, a first image may be provided from the camera head, at a first resolution, to the CCU or other electronic computing system. At stage 1730, a condition associated with the image sensor may be sensed. At stage 1740, responsive to the sensing, a second image may be generated from data provided from the image sensor at a second resolution different from the first resolution. At stage 1750, the second image may be provided to the CCU.

The process 1700 may further include, for example, providing a first visual output corresponding to the first image on a display device, and providing a second visual output corresponding to the second image on the display device.

The first image and the second image may, for example, be provided as frames of a video signal. The second resolution may be lower than the first resolution. The first image may correspond with approximately the field covered by the full frame of the image sensor and the second image corresponds with a subset of the field covered by the full frame. The subset may be a the of the full frame. The may be approximately one quarter of the full frame. Alternately, the may be approximately one ninth of the full frame. The may be approximately centered within the field of view of the image sensor.

The process 1700 may further include, for example, receiving a the selection signal from the CCU. The position may be based at least in part on the selection signal. The process 1700 may further include receiving a tile selection signal from the CCU. The tile size may be based at least in part on the tile selection signal. The tile selection signal may be a zoom-in signal. The tile selection signal may be a zoom-out signal. The tile selection signal may be a position translation signal. The tile selection signal may be a rotation signal. The tile selection signal may be a combination of one or more of the above-described signals. The process 1700 may further include receiving a tile selection signal at the camera head from the CCU. The tile size and/or tile position may be based at least in part on the tile selection signal.

In an exemplary embodiment, the tile position may be set and/or shifted to any position on a pixel by pixel basis (e.g., panning). For example, a multi-axis user interface device, such as the user interface device described in U.S. patent application Ser. No. 13/110,910, entitled USER INTERFACE DEVICES, APPARATUS, AND METHODS, may be used to control pan position.

The condition may correspond, for example, to a motion of the image sensor. The motion may be a stop motion. The motion may be a speed threshold. The motion may be a start motion. Motion or vibrational signals may be sensed by devices such as accelerometers, compass sensors, counters, or other sensing elements in the camera head, push cable, or associated components such as cable reels. The condition may be a rotation of the image sensor relative to a reference orientation. The reference orientation may be an up-down gravitational orientation. The condition may be related to one or more of the above-described motions or rotations.

The first image may correspond, for example, with approximately the full frame of the image sensor, and the second image corresponds with a subset of the full frame. The subset of the full frame may be selected based at least in part on the motion of the image sensor. The process 1700 may further include providing data associated with the second image to the CCU. The second image may correspond to a tiled subset of the full frame and the data corresponds to a position and/or size of the tiled subset.

Figure 18:
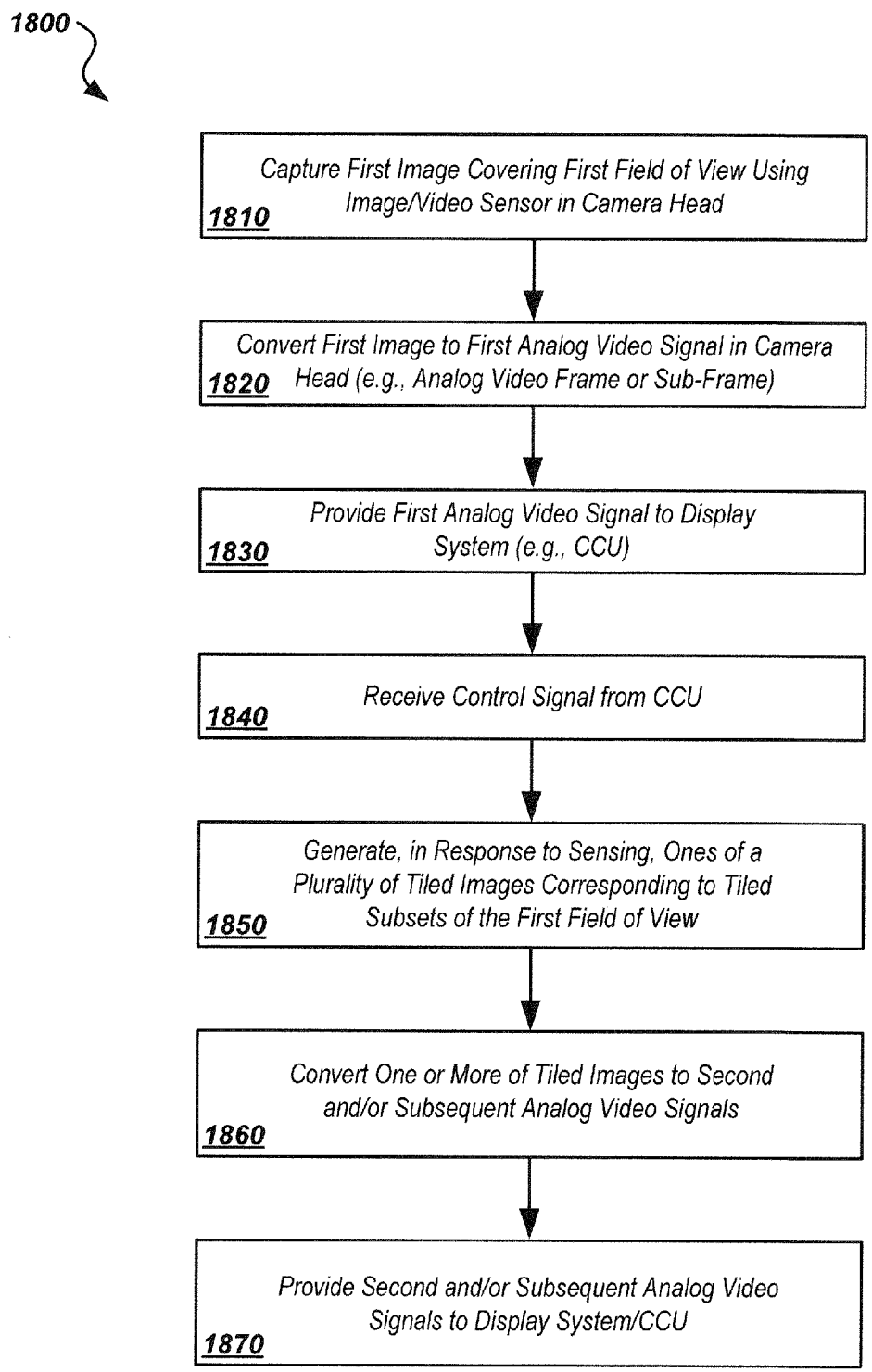
FIG. 18 illustrates details of an embodiment of a process for providing a CCU automatically generated variable resolution display in an inspection system.

FIG. 18 illustrates details of an embodiment of a process 1800 for providing a variable-resolution visual display in an inspection system, such as a pipe inspection system, based on an automatically generated CCU control signal. Process 1800 may begin at stage 1810 where a first image may be captured in an electronic image sensor of a camera head, with the first image covering a first field of view. At stage 1820, the first image may be converted to a first analog signal, and providing to a camera control unit (CCU) at stage 1830. Process 1800 may further include receiving a control signal from the CCU at stage 1840. At stage 1850, at least partially in response to the sensing or user input, ones of a plurality of tiled images corresponding to tiled subsets of the first field of view may be generated, such as in a processing element of the camera head. At stage 1860, the plurality of tiled images may be converted to a second analog signal. The second analog video signal may be provided to the CCU or other display device at stage 1870.

The process 1800 may further include, for example, receiving the first analog signal at the CCU, providing a first visual output corresponding to the first analog signal on a display device at a first resolution, receiving the second analog signal at the CCU, and combining the plurality of tiled images of the second analog signal to provide a second visual output on the display device at a second resolution higher than the first resolution.

The process 1800 may further include, for example, generating the control signal at the camera control unit. The control signal may be generated based on a user input received at the CCU. Alternately, or in addition, the control signal may be generated at the CCU using an electronic analysis of motion based on previously received images or video frames from the camera head. The analysis may include a determination of lack of motion in the previously received images. The lack of motion may be determined based on changes in one or more features of the previously received images or video frames.

The imaging sensor may be a high resolution sensor and the first image may be captured at a high resolution. In some embodiments the first image and/or plurality of tiled images may be provided as a digital signal rather than an analog video signal.

The process 1800 may further include, for example, receiving the first analog signal at a system display device, such as a camera control unit (CCU), and providing a first visual output corresponding to the first analog signal on a display device at a first resolution. The method may further include receiving the second analog signal and combining, such as in a processing element of the CCU or other system display device, the plurality of tiled images of the second analog signal to provide a second visual output on the display device. The second visual output may be provided at a second resolution that is higher than the first resolution.

The process 1800 may further include, for example, generating a second plurality of tiled images corresponding to tiled subsets of the first field of view, converting the second plurality of tiled images to a third analog signal, providing the third analog signal to the CCU, and combining the second plurality of tiled images of the third analog signal to provide a third visual output on the display device at a third resolution different than the first and the second resolutions.

The second and/or third visual outputs may, for example, be provided as a zoomed-in field of view relative to the first visual output. The first image and/or second image may be provided as frames of a video signal. The first image and the aggregate of the tiled subsets may correspond to the same field of view. The aggregate of the tiled subsets may correspond to a narrower field of view than the first image. Alternately, the aggregate of the tiled subsets corresponds to a wider field of view than the first image. The first image and the aggregate of the tiled subsets may approximately correspond to the field covered by the full frame of the image sensor. A subset of tiles may be used to create zoomed and/or panned out images. The camera head may be configured to send a sub-set of the tile grid if the CCU does not require all tiles to generate the zoomed in display.

The CCU may be configured to communicate information to the camera head to coordinate configuration and information transfer, in either one or both directions. For example, the CCU may send a configuration signal to the camera head to send only the tiles needed at the CCU or switching operating modes, while other operating modes only require the camera head to communicate with the CCU.

The plurality of tiled images may include, for example, four tiled images. Each of the four tiled images may correspond to approximately one quarter of the first field of view. Alternately, the plurality of tiled images may include nine tiled images and each of the nine tiled images corresponds to approximately one ninth of the first field of view. In other embodiments, different numbers of tiles, such as 2 tiles, 6 tiles, 12 tiles, or other numbers of tiles may be used. In an exemplary embodiment, some tile sizes may use binned pixels for improved security.

The process 1800 may further include, for example, providing data associated with the plurality of tiled images. The data may relate to a position and/or size of the ones of the plurality of tiled images. Alternately, or in addition, the data may relate to a transmission mode in use in the pipe inspection system, such as a high resolution or medium resolution still mode or a high resolution reduced frame rate video mode. Alternately, or in addition, the data may relate to one or more sensing conditions associated with the images being transmitted, such as information generated by motion sensors, position sensors, pressure or temperature sensors, audio or optical sensors, or other sensors. The data may be sent in every video frame or may be sent in only certain frames. The data may be sent in another communication channel from the video signals, such as a second wired or wireless transmission medium.

The first image and/or the ones of a plurality of tiled images and/or the corresponding higher resolution images or video may be stored on a digital storage medium, such as a flash memory or drive, a disc, removable storage media, Blu-Ray, DVD media, and the like. Alternately, or in addition, the first image and/or the ones of a plurality of tiled images may be provided as a hard copy output.

The subset of the plurality of tiled images may, for example, be used to generate the zoomed-in field of view of the second visual output. The data may relate to electronic image sensor status information and/or camera head information at the time of image capture.

In another aspect, a camera head may include an imager including a plurality of imaging elements, each of which include an image sensors and associated optics. Lighting elements, such as LEDs or lasers, may also be included in the camera head to provide lighting markers on areas being inspected (e.g., inside pipes, conduits, cavities, or other voids) that may be used to process images/video generated by the imaging elements to provide alignment between pixel outputs from multiple sensors and the like. Such a camera head may be used to implement additional functionally in various of the process embodiments described previously herein (e.g., as described with respect to the processes of FIGS. 4, 9A-9G, and 10-18).

For example, the processes may further include capturing a subsequent image in a second electronic imaging element of the camera head, and generating a third analog signal. The third analog signal may be based at least in part on the subsequent image. The third analog signal may be based entirely on the subsequent image. The third analog signal may be generated based on a combination of the subsequent image captured by the second image sensor and one or more pixels of a previous image captured by the image sensor. The subsequent image may be captured during or subsequent to a transition of a viewport or tile across an overlap area between the first image sensor and the second image sensor.

The processes may further include generating an output image sequence or video stream from two or more imaging elements in the camera head. The output image sequence or video stream may be switched from pixel data of a first imaging element of the two or more imaging elements to pixel data from a second imaging element of the plurality of imaging elements, such as during transition of a viewport through an overlap region of the field of view or coverage area of the imaging elements. The process may include projecting, from the camera head, a light marker on an area being inspected. The light marker may be a laser dot or plurality of laser dots. The light marker may be a target graphic generated by a grating or other optical element. The target, such a laser dot or plurality of laser dots or other graphic, may be strobed in synchronization with a video frame rate associated with the imaging elements or a processing element of the camera head. The strobing may provide the target during only certain image captures or video frames.

The processes may further include registering images from a first image sensor of a plurality of image sensors with one or more other image sensors of the plurality of image sensor using the projected target. The registering images may be done with images generated during transition of the viewport through the overlap region. The processes may further include capturing a subsequent plurality of images in the camera head at different exposures and generating, based on the subsequent plurality of images, a high dynamic range (HDR) image. The processes may further include generating a plurality of HDR images and generating a video stream based on the plurality of HDR images. The processes may further include projecting, from the camera head, a light marker or target on an area being inspected. The processes may further include generating the HDR image based in part on registration of the images at different exposures using the projected light marker or target.

The processes may further include capturing a subsequent image in a second electronic image sensor of the camera head and generating a stereoscopic image pair or stereoscopic video stream based on the subsequent image and an additional image captured by the image sensor. The processes may further include projecting, from the camera head, a light marker or target on an area being inspected. The processes may further include generating the stereo pair based in part on registration of the subsequent image and additional image using the projected light marker or target.

The processes may further include capturing a subsequent image in a second electronic image sensor of the camera head and generating a stitched composite image or video stream based on the subsequent image and an additional image captured by the image sensor. The processes may further include projecting, from the camera head, a light marker or target on an area being inspected. The processes may further include generating the stitched composite image based in part on registration of the subsequent image and additional image using the projected light marker or target.

Figure 19:
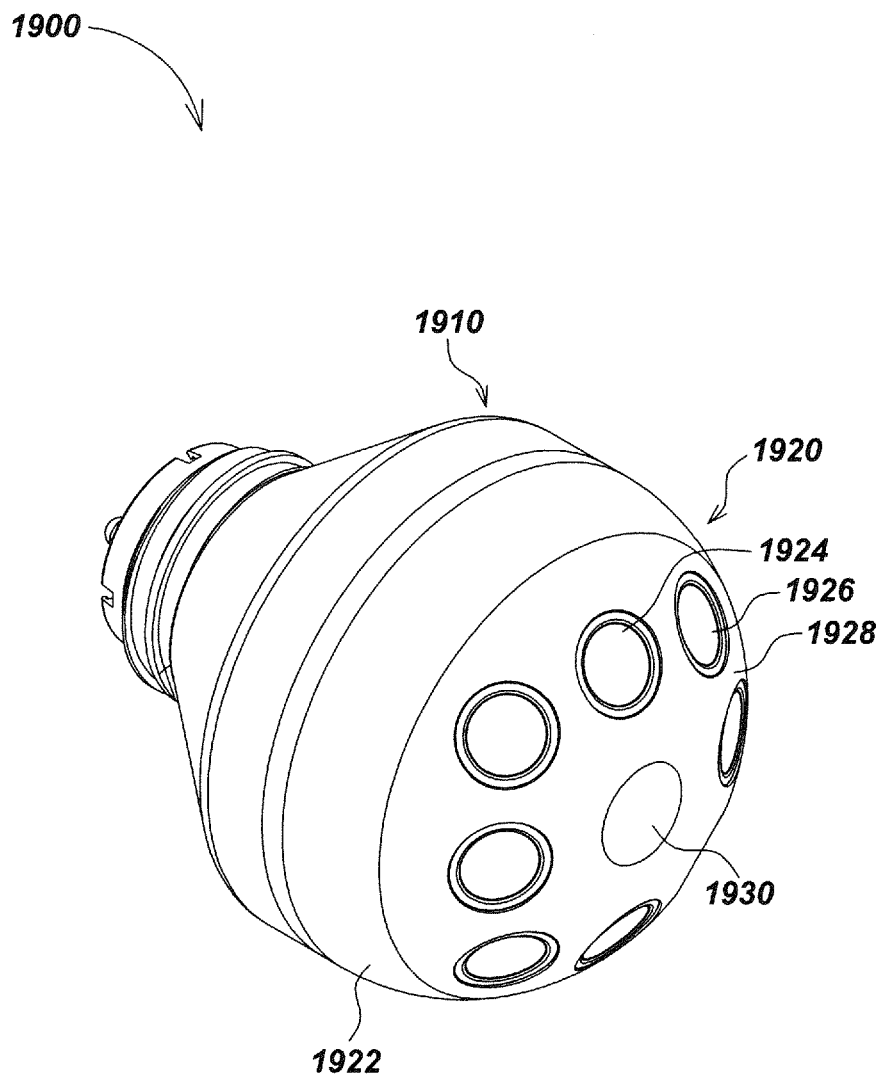
FIG. 19 illustrates details of a camera head embodiment to provide digital articulation.

Turning to FIG. 19, camera head embodiment 1900 illustrates an example camera head having multiple imaging elements, which may be used to provide digital articulation functionality based on image components provided from multiple imaging elements. Such as camera head may be used in inspection systems to provide functionality including generation of output image sequences or video streams based on images captured using two or more imaging elements, such as or subsequent to a transition of a viewport or tile across an overlap area between the first image sensor and the second image sensor. The output image sequence or video stream may be based on switching of pixel data of a first imaging element of the two or more imaging elements to pixel data from a second imaging element of the plurality of imaging elements, such as during transition of a viewport through an overlap region of the field of view or coverage area of the imaging elements.

A camera head such as shown in FIG. 19 may further be configured to project a light marker or target on an area being inspected. The light marker may be a laser dot or plurality of laser dots. The light marker may be a target graphic generated by a grating or other optical element. The target, such a laser dot or plurality of laser dots or other graphic, may be strobed in synchronization with a video frame rate associated with the imaging elements or a processing element of the camera head. The strobing may provide the target during only certain image captures or video frames. Images from a first image sensor of a plurality of image sensors may be registered with one or more other image sensors of the plurality of image sensor using the projected target in a camera head such as camera head 1900 of FIG. 19. The registering images may be done with images generated during transition of the viewport through the overlap region.

Further, a multi-sensor camera head such as camera head embodiment 1900 may be configured to capture a plurality of images in the camera head at different exposures and generate, based on the subsequent plurality of images, a high dynamic range (HDR) image. The camera head may further generate a plurality of HDR images and generate an output video stream based on the plurality of HDR images. A light marker or target may be projected from the camera head on an area being inspected. The HDR images may be based in part on registration of the images at different exposures using the projected light marker or target.

Further, a multi-sensor camera head such as camera head embodiment 1900 may be configured to capture images on a first image sensor of the camera head and a second image sensor of the camera head and generating a stereoscopic image pair or stereoscopic video stream based on the pair of images. A light marker or target may be projected from the camera head on an area being inspected. The stereo pair or stereo video stream may be based in part on registration of the images using the projected light marker or target.

Further, a multi-sensor camera head such as camera head embodiment 1900 may be configured to capture images from multiple image sensors of the camera head and generating a stitched composite image or video stream based on the multiple images. A light marker or target may be projected from the camera head on an area being inspected or viewed. The stitched composite image or video may be generated based in part on registration of the multiple images using the projected light marker or target.

Returning to FIG. 19, in an exemplary embodiment, camera head 1900 may include a rear housing assembly 1910, which may be mated with a front bezel assembly 1920 to form the housing. The front bezel assembly 1920 may include a front bezel 1922, which may be fitted with one or more windows or ports, such as one or more imager windows 1924, which may be flat sapphire windows or other transparent windows, one or more laser windows 1926, which may likewise be sapphire windows or other transparent windows, and one or more LED windows, such as LED window 1928, which may be similarly configured. In operation, the imager windows form part of an optics assembly of the imaging elements to direct light to the imaging sensors for capture of images of the area being inspected. The laser windows and/or LED windows may be used to generate light to be projected onto the area being inspected, such as illuminating lighting from the LEDs, and targets or markers from the lasers, which may be LED lasers or other lasers. For example, the light may be to illuminate the area being inspected in a flood or spotlight fashion (e.g., from the LED windows) as well as to generate targets or markers, such as light dots, crosses, or other reference symbols, which may be generated by lasers and optionally associated optics, such as gratings, etc. Multiple image sensors in camera head 1900 may be used to implement the multi-sensor processing functions described previously herein. In some embodiments, a forward oriented imaging element or elements may be disposed in the camera head to capture images through one or more forward-looking windows or ports, such as window 1930 of FIG. 19.

Figure 20:
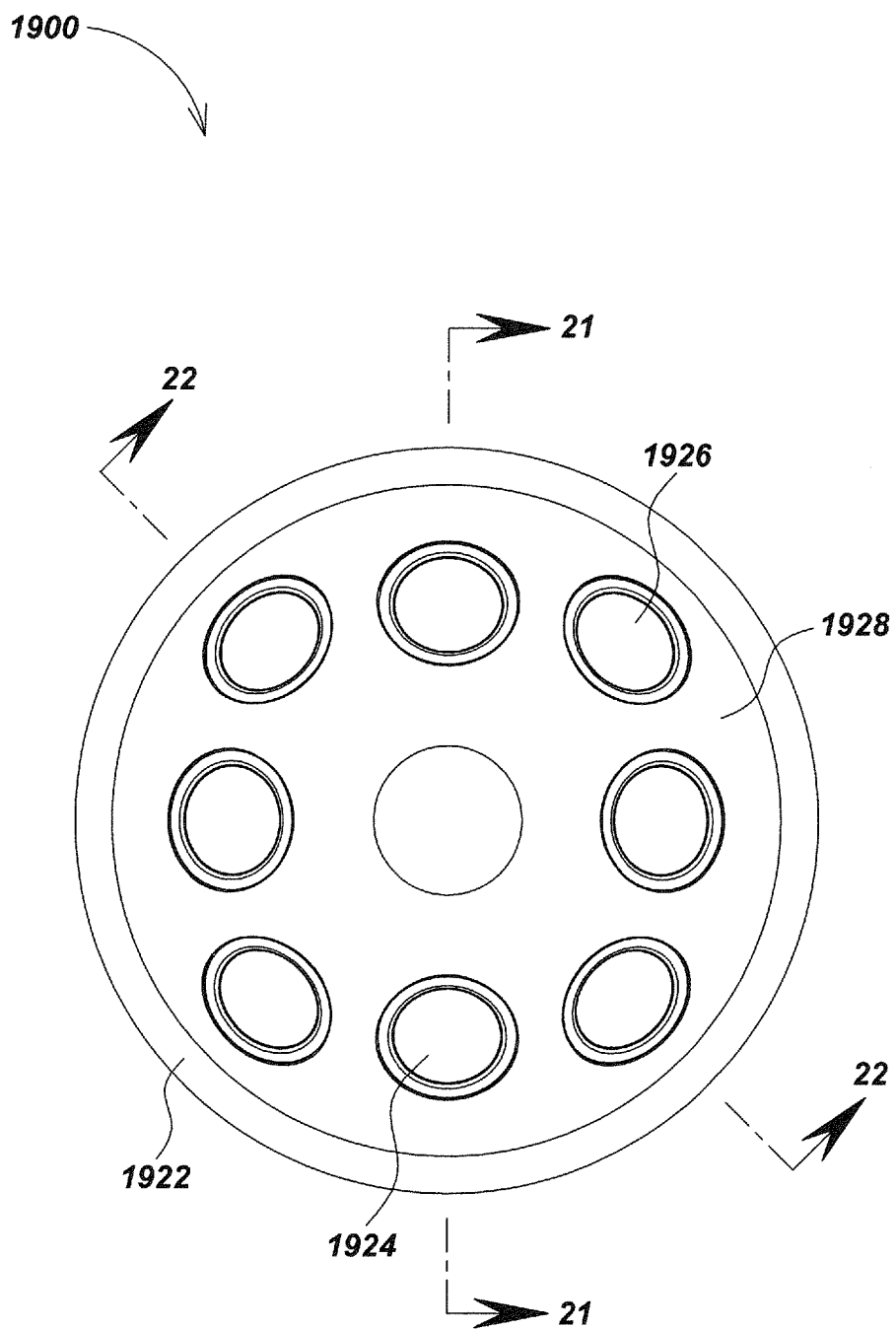
FIG. 20 illustrates details of the camera head embodiment of FIG. 19, taken from the front.

FIG. 20 is an enlarged detail view of the camera head embodiment 1900 of FIG. 19, taken from the front view.

FIG. 21 is a section view of the camera head embodiment 1900 of FIG. 20, taken from line 21-21 (through imager window 1924). It is noted that the embodiment illustrated in FIG. 21 does not include details of the forward-looking imaging element as described with respect to FIG. 19, however, such an imaging element may be disposed in the camera head by, for example, changing the size or position of the other imaging sensors shown, and/or rearranging their topology, etc. In an exemplary embodiment, camera head 1900 may include one or more image sensors (imager) 2102, such as four imaging sensors in an exemplary embodiment (or 5 with a forward-looking imaging sensor window as shown in FIG. 19) which may be mounted to an imager PCBA assembly 2110. Imager PCBA assembly 2110 may be supported an imager PCBA carrier 2114. A lens assembly, such as lens assembly 2130, may be fitted with a lens mount 2104. One or more LEDs, such as LED 2128, may be disposed on an inner LED PCBA 2126. LED window O-ring 2118 may be used to seal out moisture, particulate matter, and the like. Front bezel assembly 1920 may include a PCB capture ring 2116 and an outer LED ring PCBA 2122.

One or more PCBs, such as an imager processing PCBA 2142, a processing PCBA 2144, an encoder PCBA 2146, and a power PCBA 2148, may be disposed in the rear housing assembly 1910 and may include processing elements to perform the image processing described previously herein. One or more conductive wires, such as ribbon cable 2108, may be used to electrically connect one or more PCBs, such as imager PCBA 2112 and imager processing PCBA 2142. Lens assembly 2130 and image sensor 2102 form an instance of an imaging element and, as shown in FIG. 21, multiple imaging elements are oriented in the camera heads to have non-parallel (in this example diverging) optical axes (i.e., the optical axes diverge from a straight ahead central axis or centerline of the camera head by an angle α (alpha), as shown).

FIG. 22 is a section view of the camera head embodiment 1900 of FIG. 20, taken from line 22-22 (through laser window 1926), further illustrating a laser module 2202, which may be used to generate target light dots or markers for projection on areas being inspected to facilitate registration of images from multiple image sensors and/or to provide other image processing functions as described herein.

FIG. 23 illustrates additional details of camera head embodiment 1900 in an exploded view. As shown in FIG. 23, spacers 2305 may be used to offset the PCBs 2144, 2146 and 2148.

Figure 24:
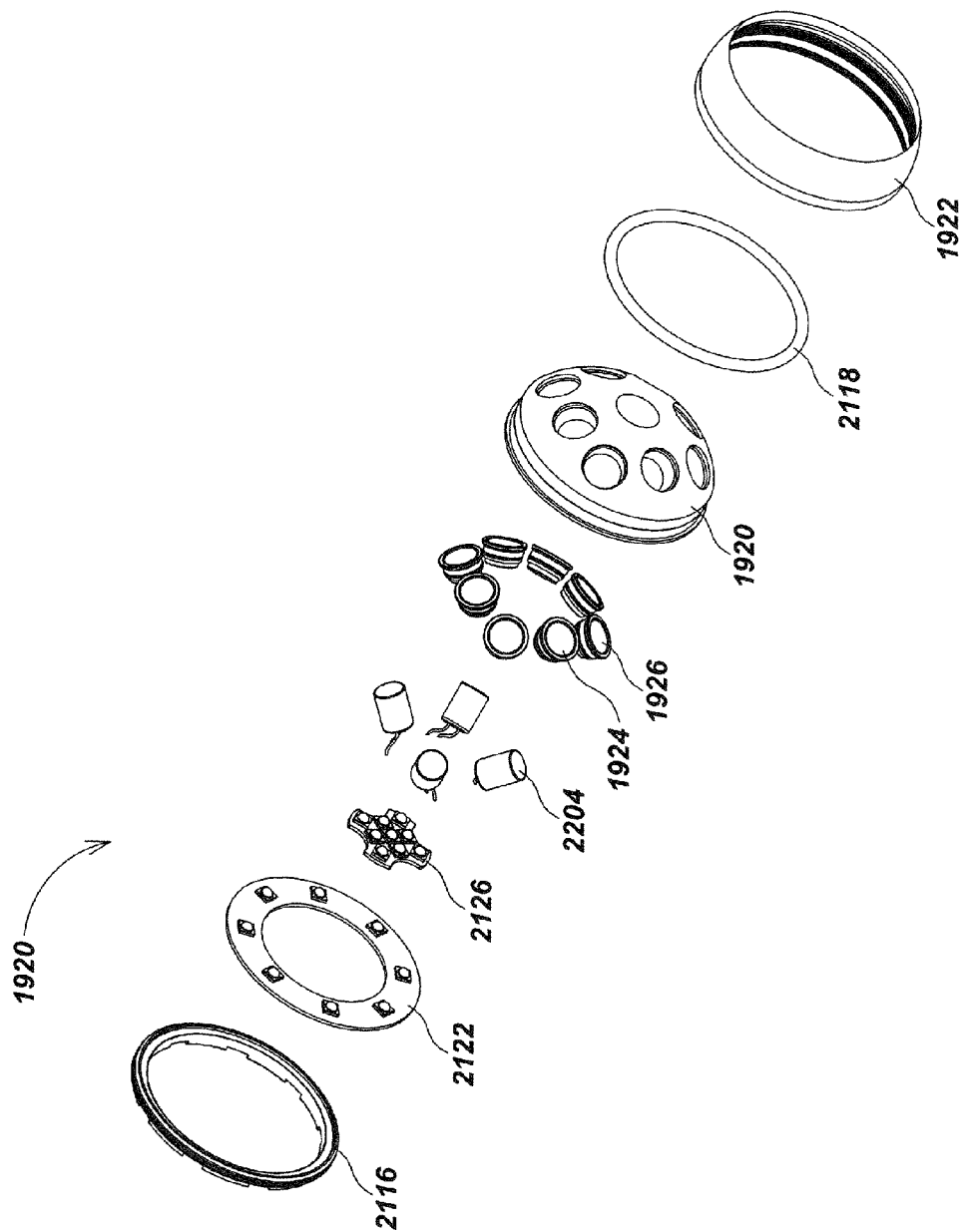
FIG. 24 is an exploded view of a front bezel assembly as illustrated in FIGS. 19-23.

FIG. 24 illustrates an exploded view of front bezel assembly 1900 of FIGS. 19-23.

Figure 25:
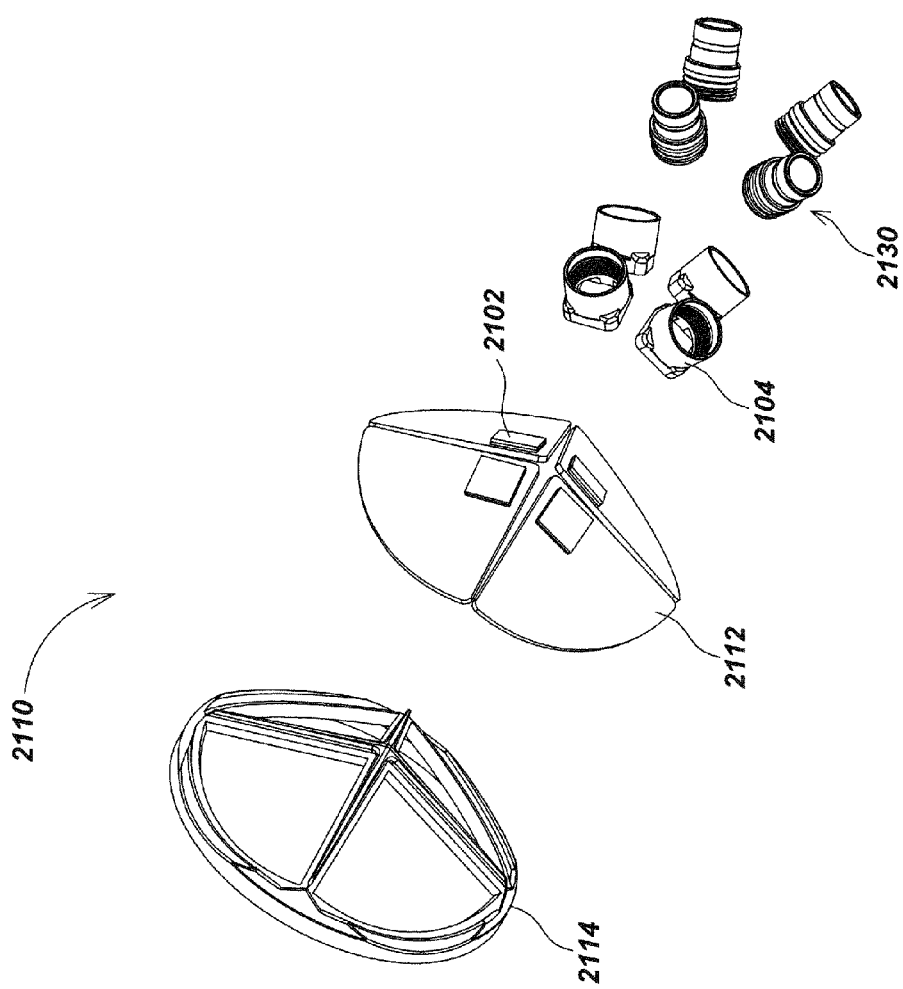
FIG. 25 is an exploded view of an imager PCB assembly as illustrated in FIGS. 21-23.

FIG. 25 illustrates an exploded view of image sensor PCB assembly embodiment 2110 as shown in FIGS. 21-23.

Figure 26:
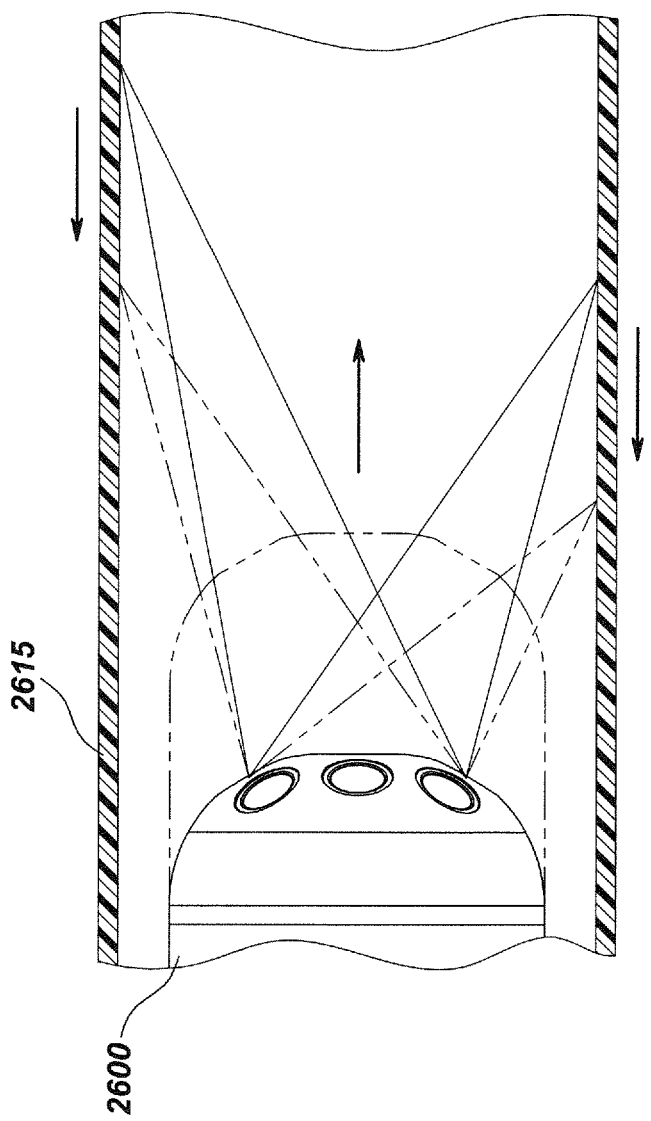
FIG. 26 illustrates how multiple lasers originate at the camera head are used to create markers on a pipe for detecting shape, orientation, or other image processing reference information.

FIG. 26 illustrates how output light dots or other markers or targets, such as from lasers in a camera head 2600, which may correspond with camera head 1900 as described previously herein, may be used to create markers on a pipe 2615 for detecting shape, orientation, or other image processing reference information. Markers or targets may be one or more laser dots, or other shapes that may be generated by a grating, such as crosses, bars or lines, rectangles, circles, or other reference shapes or graphics.

Figure 27:
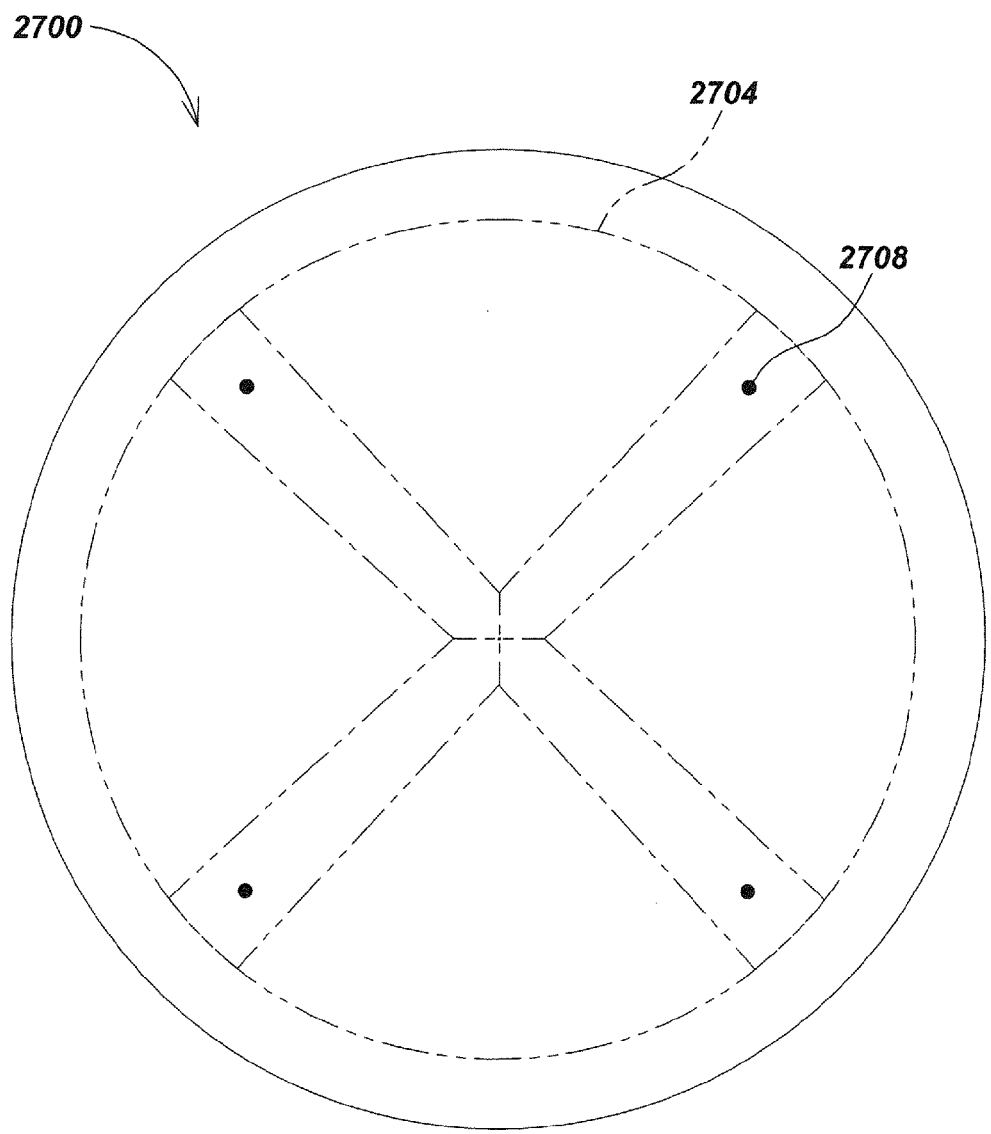
FIG. 27 illustrates how the laser dot location can be processed and correlated between the multiple imagers to the dimensions and/or shape of the inside of a pipe.

FIG. 27 illustrates an example cylindrical pipe 2700 cross section in which a camera head of an inspection system may be deployed. In this example, lasers are disposed on or within the camera head in a leveled orientation or aimed with the axis of the camera head parallel and centered on the pipe. In this example, the camera includes an image sensor array with four image sensors having overlapping fields of view (FOVs). Projected laser dots 2708, along with accelerometer and the location of each of the dots in the four image sensors can be used to estimate the shape 2704 of the pipe 2700.

Figure 28:
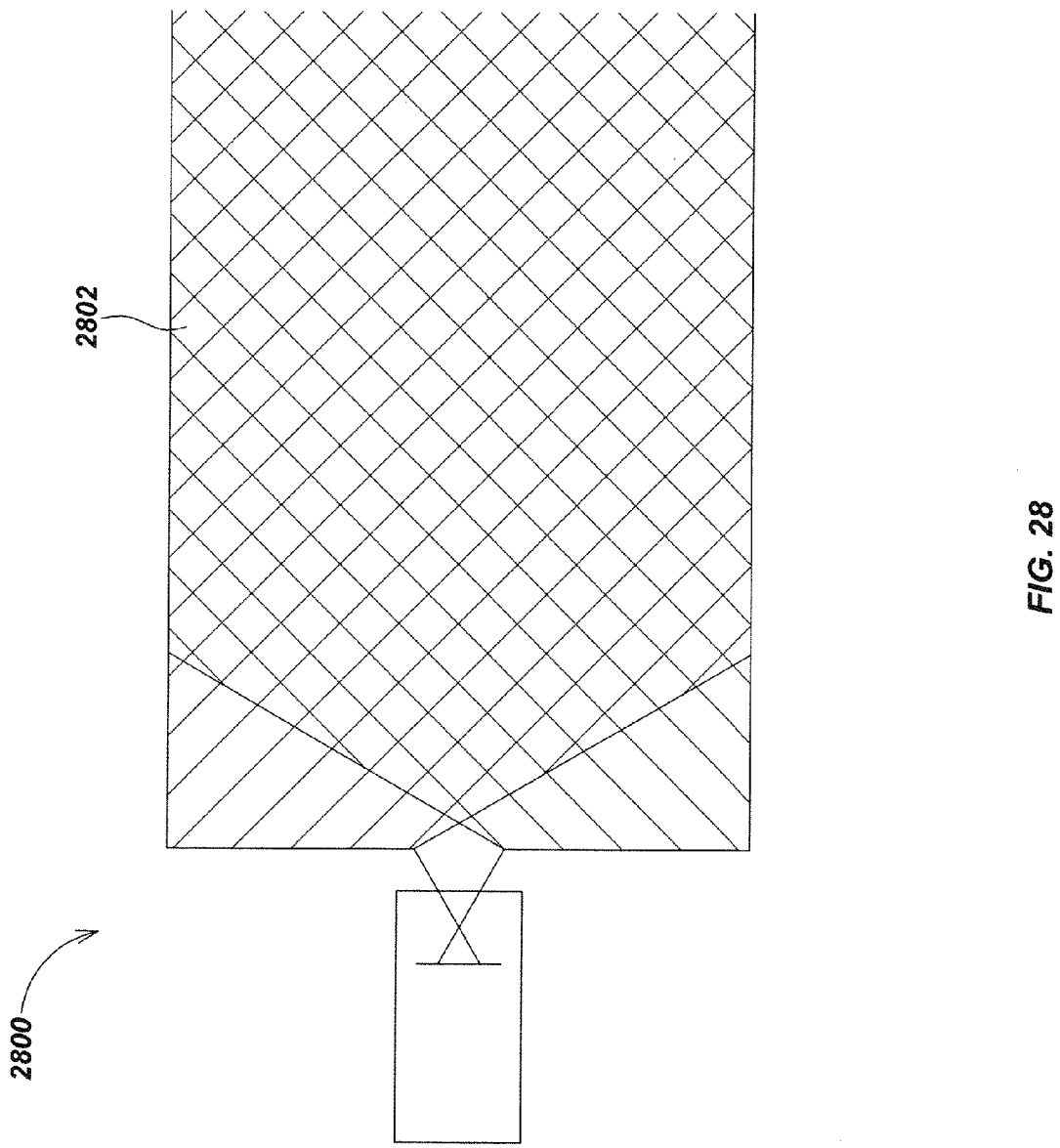
FIG. 28 illustrates how certain areas within the entire FOV of the composite (multiple integrated imagers) camera will have overlap between imagers, and some areas within the entire FOV will only be visible to a sub-set of the imagers.

FIG. 28 illustrates an example inspection camera operation showing how certain areas within the entire FOV of the image sensor array (composite image) will have overlapping areas of view 2802 between the image sensors. Some areas within the entire FOV will only be visible to a sub-set of the image sensors, whereas some areas will be within the FOV of multiple or all image sensors. Areas with overlap can be used for various processing functions described herein, such as transitioning the viewport during pan/zoom operations or rotational operations, HDR processing, stereoscopic processing 3D model generation, and the like.

FIGS. 29-31H illustrate additional details of image processing in a multi image sensor array including a plurality of imaging elements (image sensors, along with corresponding optics). The example configurations shown may be used to generate output image sequences or video streams from multiple image sensors as described previously herein, such as during translation movements of viewports across fields of view of different sensors.

Figure 29:
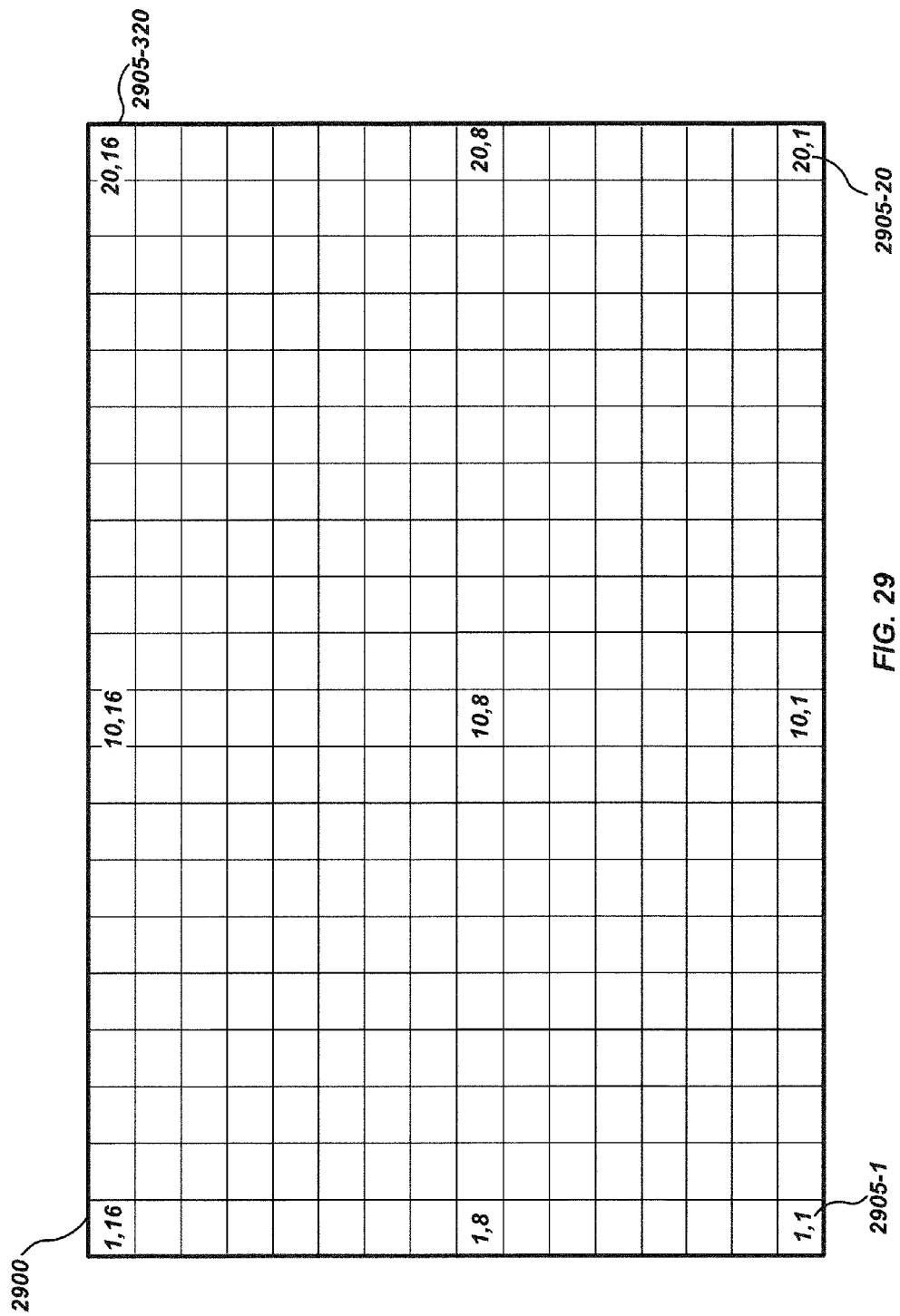
FIG. 29 illustrates an example image sensor as may be used in image sensor array embodiments.

FIG. 29 illustrates one example image sensor 2900 having an array of pixels 2905 (shown as square boxes within the sensor). In this example sensor, there are 20 columns by 16 rows of pixels, forming a 320 pixel array (denoted as pixels 2905-1 through 2905-320). Pixel array coordinates are shown, with the ordering starting at the lower left of the image sensor (i.e., coordinates 1,1 to 20, 16 in the upper right). A limited pixel array size is shown in FIG. 29 for purposes of illustration, however, in an actual image sensor, the number of pixels will typically be substantially larger, such as, for example, sensors with pixel arrays including five million or more pixels. In addition, the aspect ratio and/or shape of the pixels may vary in different image sensors, and the pixel array configuration need not necessarily be square or rectangular, but rather may have circular, oval, or other shapes.

As described previously herein, in an image sensor array with wide angle optics, the viewed areas of each imaging element may generally overlap (in some embodiments, the sensor coverage areas may abut or only slightly overlap, or in some implementations be non-overlapping, such as to cover a wider area of view with less detail, but they will generally be overlapping to facilitate smooth transitions and/or registration of images across sensors). An example of this is shown in the sensor array embodiment 3000 of FIG. 30, where four instances of image sensor 2900 are shown (denoted as image sensors 3010, 3020, 3030, and 3040, which may, for example, correspond to the four image sensor illustrated in the camera head of FIG. 23), along with their respective areas of coverage, which overlap in overlap regions 3070 and 3080.

Figure 30:
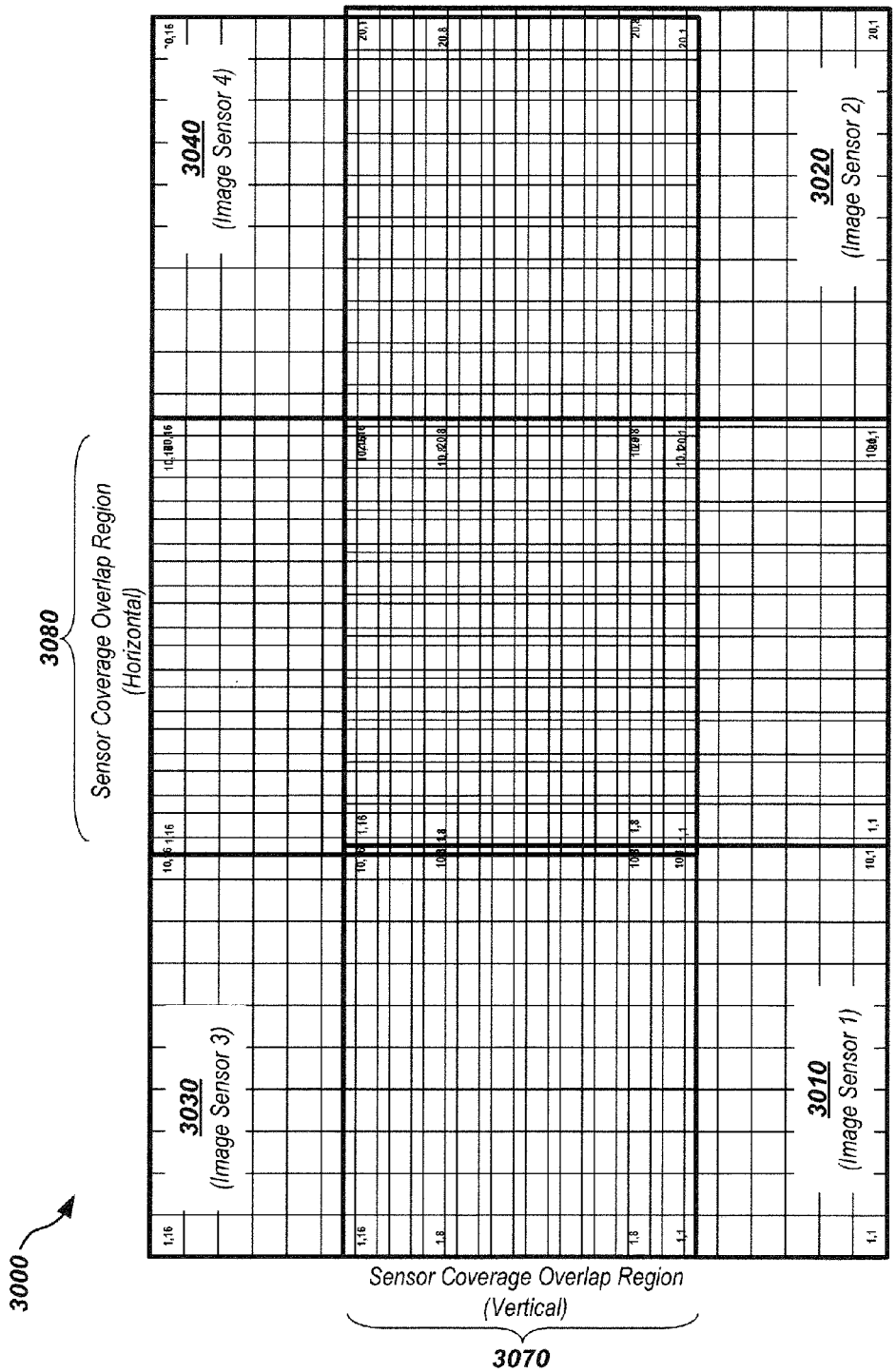
FIG. 30 illustrates an image sensor array embodiments with overlapping fields of view.

It is noted that, while the example embodiment of FIG. 30 includes four instances of the image sensors 2900 (and associated optics), in other embodiments other numbers and arrangements of image sensors and associated optics may alternately be used. For example, in some embodiments, the camera head may include a series of two or more concentric rings of imaging elements (not shown in FIG. 30). In some embodiments a single centered, forward facing imaging element (not shown in FIG. 30) may be included for a total of five imaging elements. In some embodiments, two forward facing imaging elements may be used to provide further stereoscopic imaging capability (e.g., the two forward facing imaging elements may capture a reference forward-looking stereoscopic pair, which may be used in signal processing in conjunction with the images from the other sensors). The forward facing imaging elements may be aligned on parallel optical axes oriented along the camera head centerline, or on divergent optical axes diverging about the camera head centerline. In some embodiments, forward facing imaging elements may be oriented along convergent, rather than divergent, optical axes. In addition the image sensors may be rotated in other orientations relative to each other (compared to the orientations shown in FIG. 30), such as centered along a circle about the camera head forward axes, or grouped in pairs on opposite sides of the camera head.

An optical distortion map for the optics/lenses associated with each image sensor may be predetermined, and stored in a memory of the camera head and/or CCU or other electronic computing system to be applied to captured images during image processing and mapping of the outputs of the multiple imagers for generating the output images or video, such as described previously with respect to FIGS. 9B-9G. For example, a distortion map may be applied to the image outputs of each of the image sensors as part of the image processing performed to generate a 3D surface model of the inside of a pipe or other area being inspected, or to generate tiled images or video. Application of a correction map based on predetermined distortion characteristics may also be used to correct for lens distortions (e.g., fisheye effects or other wide angle lens distortions) and/or to aid in registration of pixels from adjacent sensors when stitched together to form output images or videos based on pixels from two or more sensors.

As described previously, various image processing functions may be implemented using pixels in the overlap region, such as stereoscopic processing, 3D model generation, HDR processing, and the like. In addition, as described previously, a sensor array such as array 3000 can be used to generate output images having an extreme wide angle field of view (e.g., 180 degrees or more in camera heads using a flat port, such as a flat sapphire or other transparent port) by combining output pixels from multiple sensors into a stitched composite image or video. Further, the output viewport or tile provided from the sensor array can implement pan and zoom operations across sensor boundaries. This is further illustrated with respect to FIGS. 31A-31H, which illustrates an example panning or translational digital articulation operation.

Figure 31A:
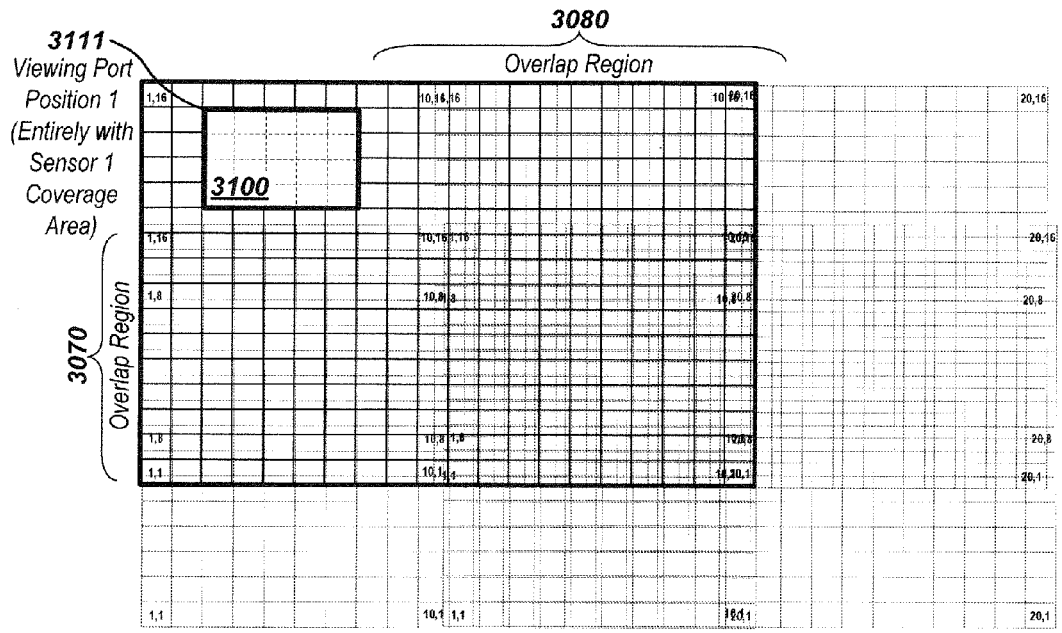
FIGS. 31A-31H illustrate example viewport or tile transitions across image sensor boundaries in the image sensor array of FIG. 30.
Figure 31B:
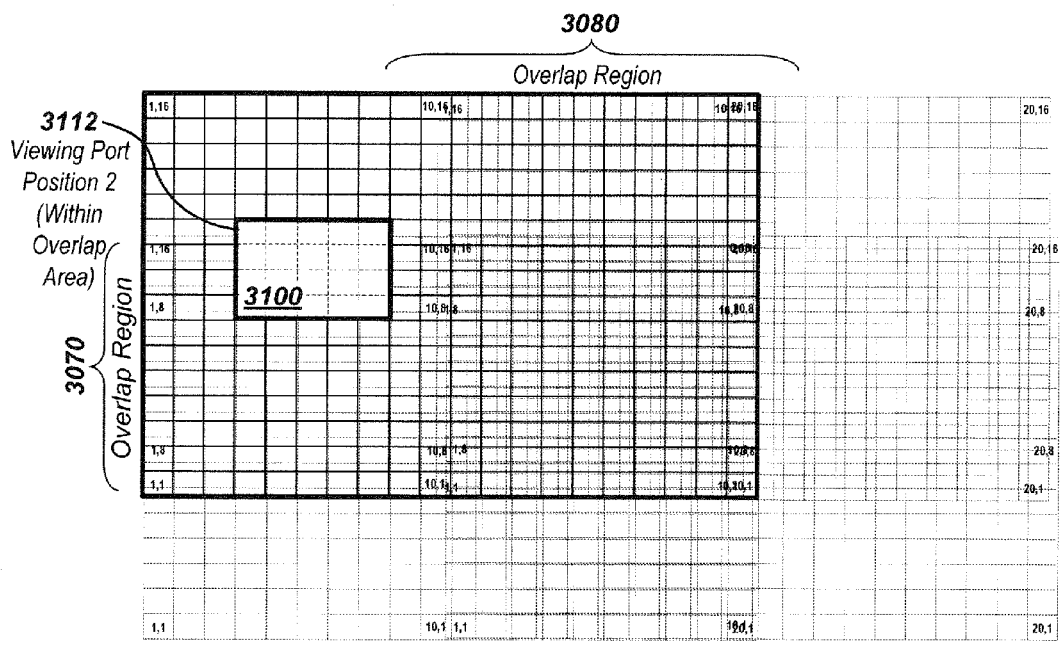

FIG. 31A illustrates an initial position 3111 of output viewport 3100, which in this case is in the upper left corner of image sensor 3. Based either on an automatic control signal or a CCU or other operator provided control signal (such as described in the process of FIG. 9G) the viewport may be moved to a different position in the image sensor array coverage area, such as position 3112 as shown in FIG. 31B. If the viewport is moved within the boundaries of a single image sensor, the output pixels for each image and/or corresponding video stream may be provided from the memory associated with the single sensor. Conversely, when the viewport is within an overlap region, such as overlap region 3070, a decision may be made as to whether to transition the output to pixels from another image sensor. As described previously herein, this may be done by either switching (hard transition) the output entirely to the pixels of the second sensor, or by soft transitioning, such as by combining pixels from each sensor or merging the pixels together to form the output images within the transition zone.

Figure 31C:
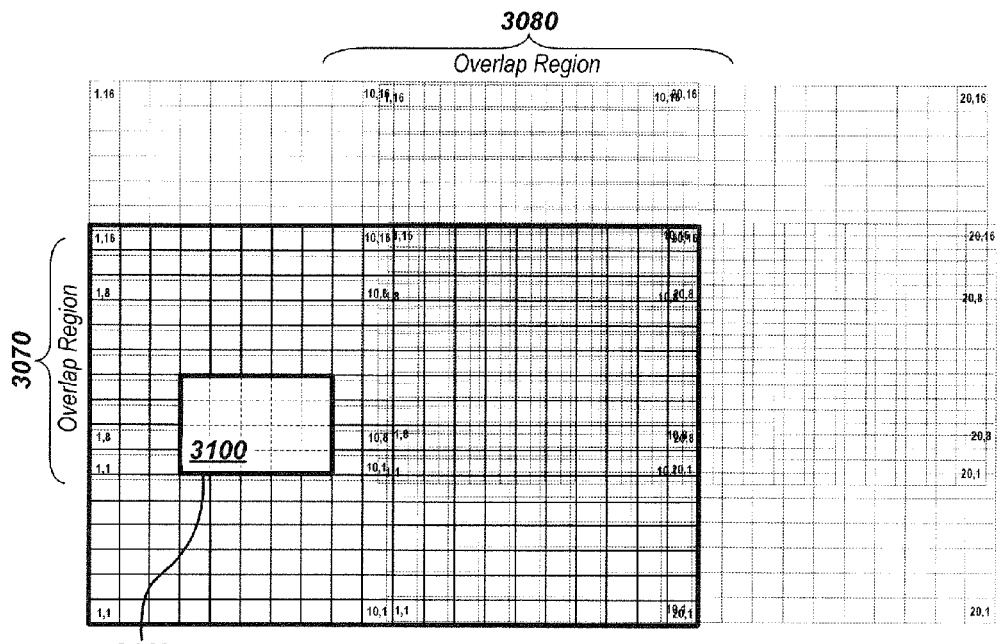
Figure 31D:
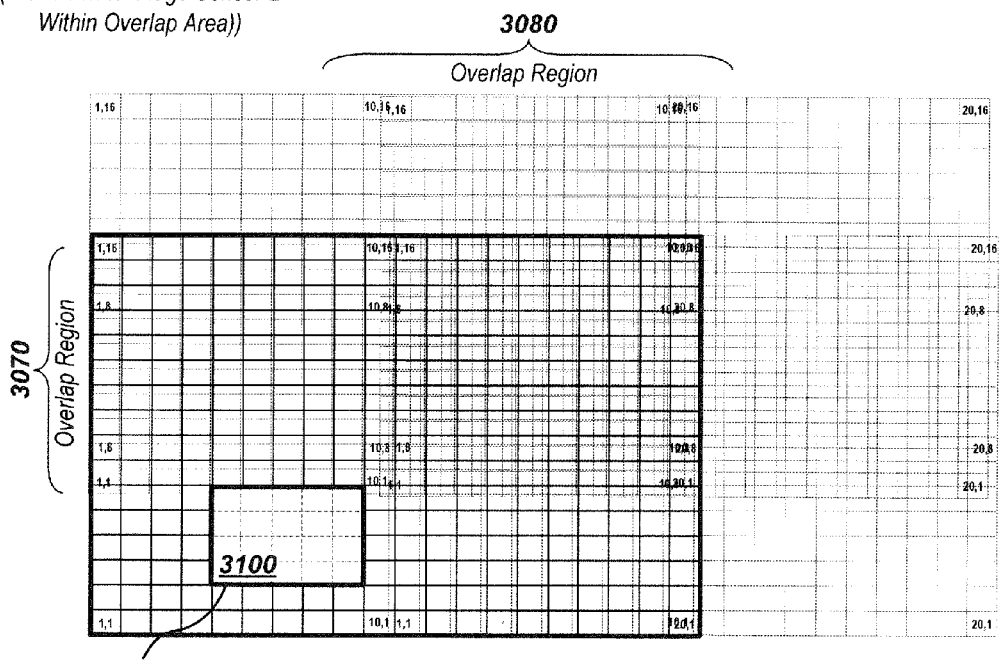
Figure 31E:
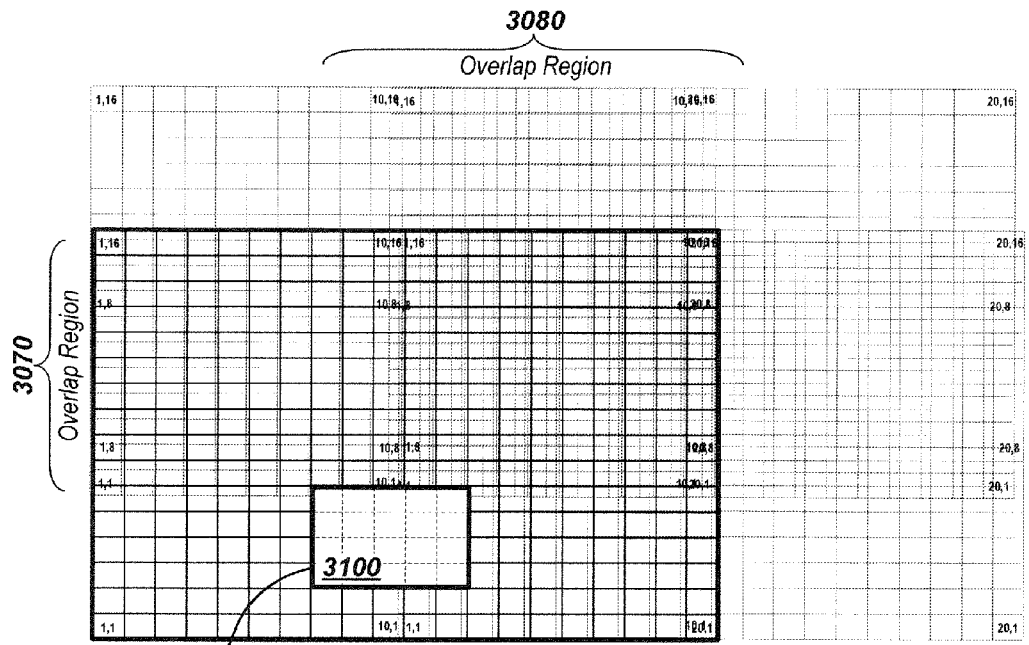
Figure 31F:
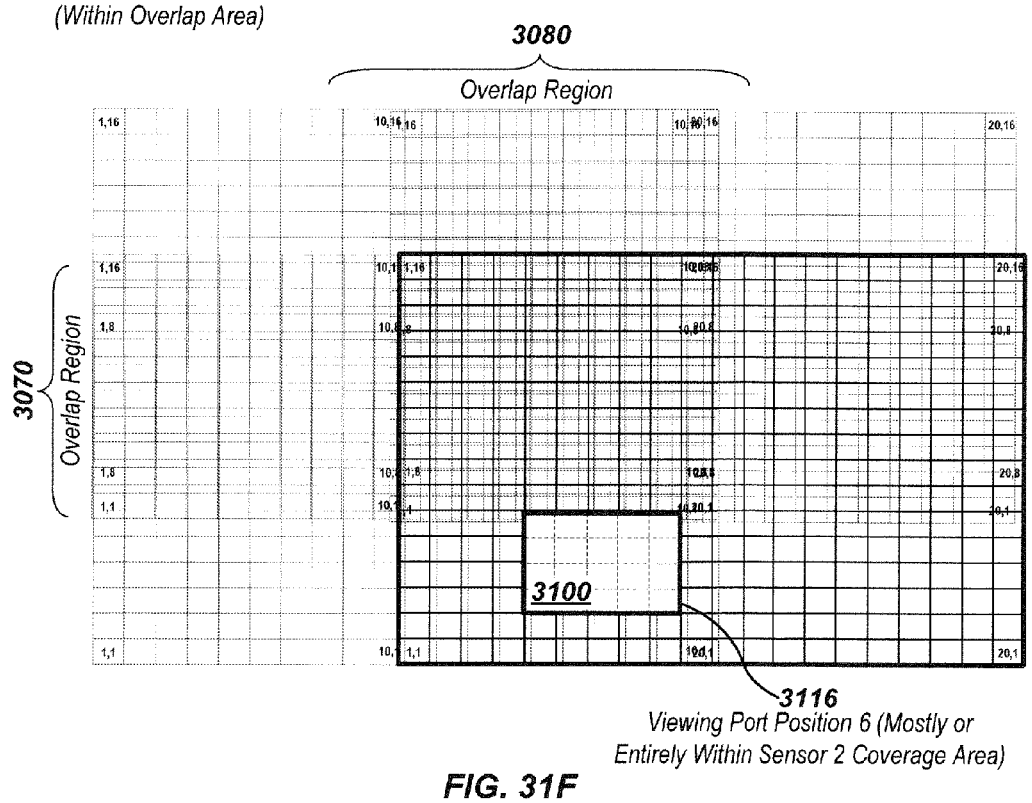
Figure 31G:
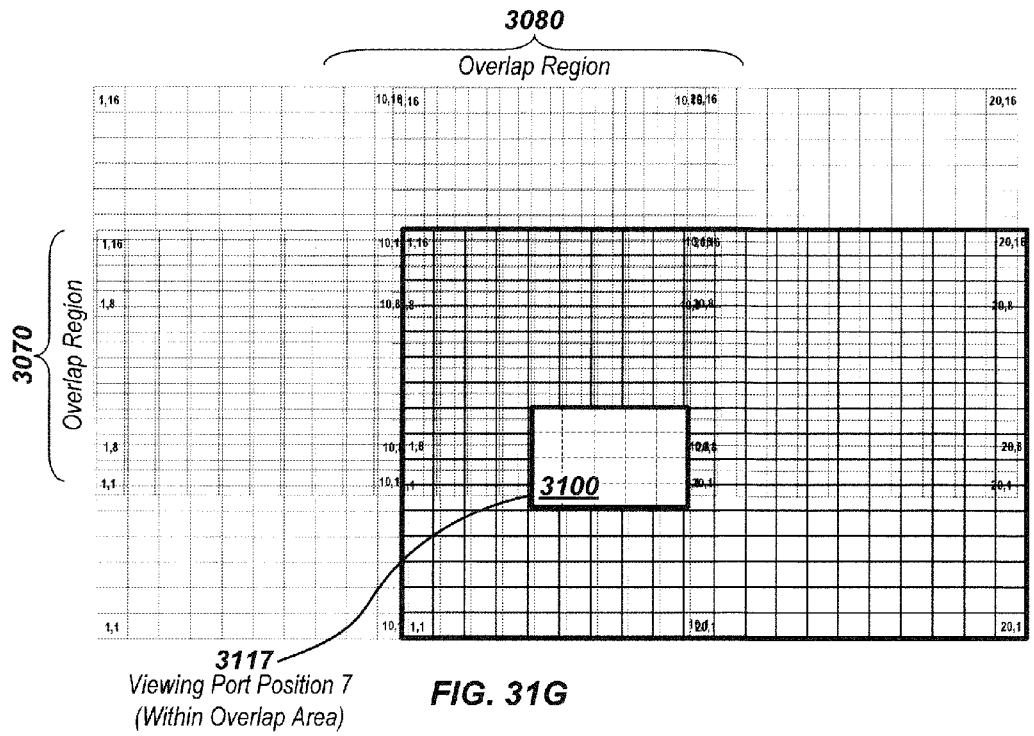
Figure 31H:
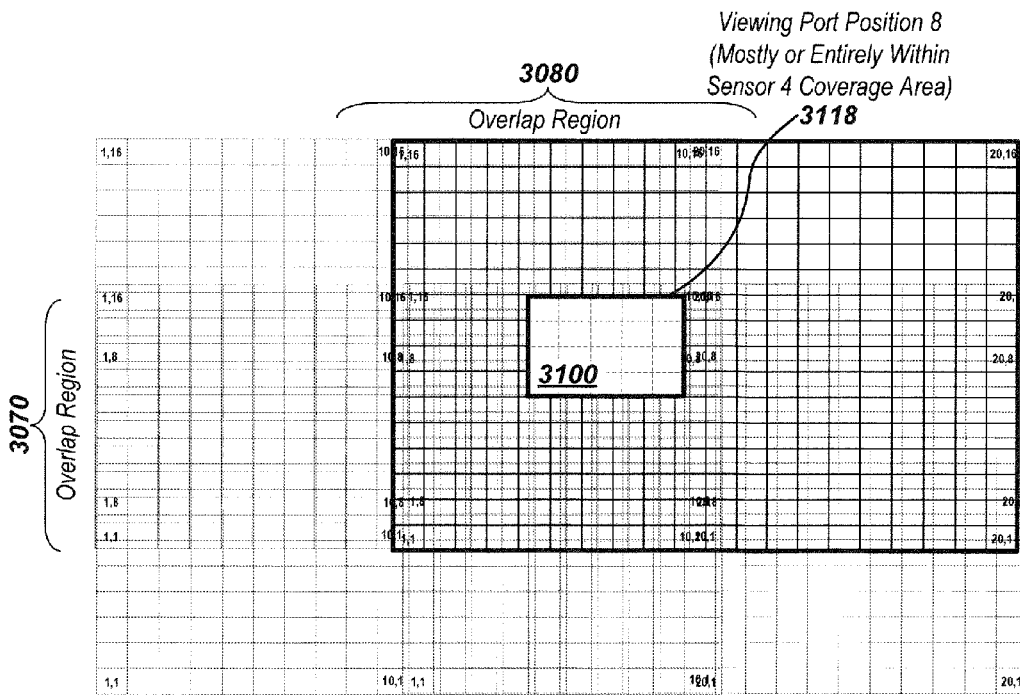

FIG. 31C illustrates a subsequent viewport position 3113, where the output is either switched entirely to the pixels of image sensor 1 or combined or merged while the viewport is still within the overlap region. FIG. 31D illustrates additional movement of the viewport to position 3114, in this case where the viewport is entirely within the coverage area of sensor 1, and the output pixels are taken entirely from image sensor 1.

FIGS. 31E-31H illustrate additional example translations of the viewport 3100 to positions 3115 through 3118, while outputs are transitioned through image sensor 2 and image sensor 4.

The term "level" or "leveled" may be used herein to describe a condition in which an object is substantially parallel relative to a horizontal plane and perpendicular to a gravitational force. For example, a flat surface on the earth normal to gravity may be a level surface.

The term "leveling" may be used in the sense of bringing an object to a position substantially parallel to a reference plane, that is, to make an object level, typically with respect to the ground and a gravitational reference.

The term "rotated" may be used herein to describe a condition in which an object is substantially parallel relative to a horizontal plane and perpendicular to gravity.

The term "camera head" may be used interchangeably with "camera," or "camera module." The terms "camera head" may be used herein to describe a device or module comprising an imaging element with an image sensor operably coupled to a lens, and may further include related or supporting electrical, optical, and/or mechanical components, such as a body or other structure and related components. The term "camera head" or "camera" may further be used herein to describe a composition comprising an image sensor operably coupled to a lens, an orientation sensor, a programmable device, such as a microprocessor, Field-Programmable Gate Array (FPGA), or DSP, as well a digital-to-analog converter and a line driver.

The term "high resolution image sensor" may be used herein to describe the resolution of the image sensor relative to the resolution of the remote monitoring system and/or display device. The term "high resolution image sensor" may be used herein to describe a semiconductor device that detects energy in the near infrared, infrared, visible, and/or ultraviolet spectrums to be used for the formation of a displayed image based on the detected energy. The detected energy may be used to form a single static image or a series of images (such as from a video camera) that may provide a moving image. Detection within the image sensor may be deployed in a planar arrangement in a two-dimensional orientation, where the detection devices (e.g. detection pixels) may be in rows and columns for digital video, or in horizontal lines slanted slightly downward for analog video. The term "high resolution image sensor" may refer to a complementary metal oxide semiconductor (CMOS), a charge-coupled detector (CCD), and/or other suitable high resolution image sensors or other detection devices.

The high resolution image sensor may be, for example, a complementary metal oxide semiconductor (CMOS). The complementary metal oxide semiconductor (CMOS) may have an element array of n rows of pixels by m columns of pixels (n×m) where n×m is at least 1600×1200.

The complementary metal oxide semiconductor (CMOS) may further have an element array configuration such as, but not in any way limited to: 1600×1200, 2048×1536, 2240×1680, 2560×1920, 3032×2008, 3072×2304, 3264×2448, 3488×2616, 4368×2912, 5616×3744, and/or 13280×9184 pixels. In one exemplary embodiment the complementary metal oxide semiconductor (CMOS) has an element array of 3488×2616. The complementary metal oxide semiconductor (CMOS) may be, for example, an OV9810 9-Megapixel 1080 HD Video Image Sensor, manufactured by the Omnivision® Company.

The term "accelerometer" is used to refer to a device that is capable of providing data related to a physical orientation and/or a position of an image sensor with respect to gravitational forces ("gravity"). Other suitable examples of orientation sensing devices that may be used are, for example, an inclinometer, a gyroscope, a magnetometer, a tilt sensor, and/or other orientation and/or position sensing devices known or developed in the art. An "accelerometer" may refer, for example, to a three-axis accelerometer, a two-axis accelerometer, and/or a one-axis accelerometer. The term "three-axis accelerometer" may be a single orientation sensor capable of measuring three perpendicular axes or acceleration and is interchangeable with three separate accelerometers arranged on three perpendicular axes.

The term "angular orientation" refers to the angle to which the image sensor is oriented with respect to gravity, g, the image recorded by the image sensor with respect to gravity, g, and/or the image to be displayed on a remote monitoring system with respect to gravity, g. Display orientation is generally independent of the physical orientation of the image sensor as might be sensed by an orientation sensor.

The term "field programmable gate array" or ("FPGA") may be used herein to describe a semiconductor device containing an array of programmable logic components, such as logic blocks, and programmable interconnects there between. Logic blocks can be programmed to perform the function of basic logic gates and/or relatively more complex combinational functions. The FPGA logic blocks may also include volatile and/or non-volatile memory elements. A hierarchy of programmable interconnects allows logic blocks to be interconnected and programmed after the FPGA is manufactured to implement any logical function.

The term "single memory array" may refer to an array of memory locations of one or more memory devices sufficiently large to hold a single n×m image or frame of video.

The term "composite video signal" may refer to a format or formats of analog video in which luminance data (brightness), chrominance data (color), and synchronization data (horizontal sync, vertical sync, and color reference bursts) are embedded in a single line-level signal. Analog video is discrete in the vertical dimension (there are distinct lines), but continuous in the horizontal dimension (every point blends into the next with no boundaries), hence there are no pixels in this format. The term "composite video signal" may refer to an analog encoding system or formatting standards for broadcast television systems. The term "composite video signal" may refer to a standard analog video format, such as Electronic Industry Association (EIA), National Television System Committee (NTSC), Committee Consultatif International Radiotelecommunique (CCIR), Phase Alternate Line (PAL), and/or Sequential Color with Memory (SECAM).

The composite video signal may be, for example, an NTSC signal, which is used in most of North America and South America. The NTSC standard most commonly employed is an interlaced system where each frame is scanned for two fields at 262.5 lines per field, and is combined to display a frame of video with 525 horizontal scan lines slanting slightly downward from left to right. NTSC scans at 29.97 frames per second, with 59.94 fields displayed per second.

The term "field" refers to a set of even lines and/or odd lines. One field contains all the odd lines of the image; and the other field contains all the even lines of the image. The odd and even lines are displayed sequentially, thus interlacing a full frame. One full frame is produced by two interlaced fields, and is displayed approximately every 1/30 of a second. Fields can be interlaced or progressively scanned depending on the video standard used.

In various embodiments, digital self-leveling pipe inspection camera systems consistent with the present invention are subject to a wide variety of modifications not described above. For example, the digital self-leveling pipe inspection camera system may be utilized in applications not associated with pipe inspection, such as assembly line monitoring, endoscopy, and/or other inspection or analysis applications.

The word "exemplary" is used herein to mean "serving as an example, instance, or illustration." Any aspect and/or embodiment described herein as "exemplary" is not necessarily to be construed as preferred or advantageous over other aspects and/or embodiments.

In some configurations, the various systems and modules include means for performing various functions as described herein. In one aspect, the aforementioned means may be a processor or processors and associated memory in which embodiments reside, and which are configured to perform the functions recited by the aforementioned means. The aforementioned means may be, for example, processors, logic devices, memory, and/or other elements residing in a camera head, camera control module, display module, and/or other modules or components as are described herein. In another aspect, the aforementioned means may be a module or apparatus configured to perform the functions recited by the aforementioned means.

In one or more exemplary embodiments, the functions, methods and processes described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented unless explicitly noted.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

The various illustrative logical blocks, modules, and circuits described in connection with the embodiments disclosed herein may be implemented or performed in a processing element with a general purpose processor, special purpose processor, digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine, which may be programmed to perform the specific functionality described herein, either directly or in conjunction with an external memory or memories. A processor may also be implemented as a combination of computing devices, e.g., a combination of a DSP and a microprocessor, a plurality of microprocessors, one or more microprocessors in conjunction with a DSP core, or any other such configuration.

As used herein, computer program products comprising computer-readable media including all forms of computer-readable medium except, to the extent that such media is deemed to be non-statutory, transitory propagating signals.

Various modifications to the aspects described herein will be readily apparent to those skilled in the art, and the generic principles defined herein may be applied to other aspects without departing from the spirit or scope of the invention. Accordingly, the scope of the invention is not intended to be limited to the aspects shown herein, but is to be accorded the widest scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

Thus, the present invention is not intended to be limited to the aspects and details shown herein but is to be accorded the widest scope consistent with the appended claims and their equivalents.

We claim:

1. A method of providing a variable-resolution visual display in an inspection system, comprising:
   capturing a first image, covering a first field of view, in an electronic imaging element of a camera head, the electronic imaging element including an image sensor and imaging optics;
   converting the first image to a first analog signal;
   providing the first analog signal to an electronic computing system;
   sensing a condition associated with the camera head;
   generating, responsive to the sensing, ones of a plurality of tiled images corresponding to tiled subsets of the first field of view;
   converting the plurality of tiled images to a second analog signal; and
   providing the second analog signal to the electronic computing system.

2. The method of claim 1, further comprising:
   receiving the first analog signal;
   providing a first visual output corresponding to the first analog signal on a display device at a first resolution;
   receiving the second analog signal; and
   combining the plurality of tiled images of the second analog signal to provide a second visual output on the display device at a second resolution higher than the first resolution.

3. The method of claim 2, further comprising;
   generating a second plurality of tiled images corresponding to tiled subsets of the first field of view;
   converting the second plurality of tiled images to a third analog signal;
   providing the third analog signal to the electronic computing system; and
   combining the second plurality of tiled images of the third analog signal to provide a third visual output on the display device at a third resolution different than the first and the second resolutions.

4. The method claim 2, wherein the second visual output is provided as a zoomed-in field of view relative to the first visual output.

5. The method of claim 2, wherein the first image and the second image are provided as frames of a video signal.

6. The method of claim 1, wherein the first image and the aggregate of the tiled subsets correspond to the same field of view.

7. The method of claim 1, wherein the aggregate of the tiled subsets corresponds to a narrower field of view than the first image.

8. The method of claim 1, wherein the aggregate of the tiled subsets corresponds to a wider field of view than the first image.

9. The method of claim 1, wherein the first image and the aggregate of the tiled subsets approximately correspond to the field covered by the full frame of the image sensor.

10. The method of claim 1, wherein the condition corresponds to a motion of the camera head.

11. The method of claim 10, wherein the motion is a stop motion.

12. The method of claim 10, wherein the motion is a speed threshold.

13. The method of claim 10, wherein the motion is a start motion.

14. The method of claim 10, wherein the condition is a rotation of the image sensor relative to a reference orientation.

15. The method of claim 14, wherein the reference orientation is an up-down gravitational orientation.

16. The method of claim 1, further comprising providing data associated with the plurality of tiled images, wherein the data relates to a position and/or size of the ones of the plurality of tiled images.

17. The method of claim 1, wherein the ones of the plurality of tiled images are at a lower resolution than the first image.

18. The method of claim 1, further comprising providing data associated with the plurality of tiled images, wherein the data relates to a transmission mode currently in use, wherein the transmission mode is one of a single frame-mode or a tiled mode.

19. The method of claim 1, further comprising providing data associated with the plurality of tiled images, wherein the data relates to one or more sensing conditions associated with the image being transmitted.

20. The method of claim 1, further comprising capturing a subsequent image in a second electronic imaging element of the camera head; and
generating a third analog signal based at least in part on the subsequent image.

21. The method of claim 20, wherein the third analog signal is based entirely on the subsequent image.

22. The method of claim 20, wherein the third analog signal is generated based on a combination of the subsequent image captured by the second image sensor and one or more pixels of a previous image captured by the image sensor.

23. The method of claim 20, wherein the subsequent image is captured during or subsequent to a transition of a viewport across an overlap area between the first image sensor and the second image sensor.

24. The method of claim 20, further including projecting, from the camera head, a light marker on an area being inspected.

25. The method of claim 24, wherein the third analog signal is based in part on registration of the subsequent image an image captured in the image sensor using using the light marker.

26. The method of claim 1, further comprising:
capturing a subsequent plurality of images at different exposures; and
generating, based on the subsequent plurality of images, a high dynamic range (HDR) image.

27. The method of claim 26, further comprising generating a plurality of HDR images and generating a video stream based on the plurality of HDR images.

28. The method of claim 1, further comprising capturing a subsequent image in a second electronic image sensor of the camera head; and
generating a stereoscopic image pair based on the subsequent image and an additional image captured by the image sensor.

29. The method of claim 1, further comprising capturing a subsequent image in a second electronic image sensor of the camera head; and
generating a stitched composite image based on the subsequent image and an additional image captured by the image sensor.

30. The method of claim 29, further comprising projecting, from the camera head, a light marker on an area being inspected, wherein the generating a stitched composite image is based in part on registration of the subsequent image and additional image using the projected marker.

31. The method of claim 20, further including projecting, from the camera head, a light marker on an area being inspected.

32. The method of claim 31, wherein the light marker is a laser dot or plurality of laser dots.

33. The method of claim 31, wherein the laser dot or plurality of laser dots are strobed in synchronization with a video frame rate associated with the imaging elements or a processing element of the camera head.

34. The method of claim 31, further comprising registering the subsequent image with an image generated by the image sensor based at least in part on the light marker.

35. The method of claim 1, wherein the electronic computing system is a camera control unit (CCU).

* * * * *